US012385928B2

(12) United States Patent
Lui et al.

(10) Patent No.: US 12,385,928 B2
(45) Date of Patent: Aug. 12, 2025

(54) AMYLOID PRECURSOR PROTEIN AS A DIAGNOSTIC MARKER FOR BILIARY ATRESIA

(71) Applicant: Versitech Limited, Hong Kong (CN)

(72) Inventors: Chi Hang Lui, Hong Kong (CN); Rosana Ottakandathil Babu, Hong Kong (CN); Paul Kwong Hang Tam, Hong Kong (CN)

(73) Assignee: Versitech Limited, Hong Kong (CN)

( * ) Notice: Subject to any disclaimer, the term of this patent is extended or adjusted under 35 U.S.C. 154(b) by 975 days.

(21) Appl. No.: 17/418,732

(22) PCT Filed: Jan. 13, 2020

(86) PCT No.: PCT/CN2020/071742

§ 371 (c)(1),
(2) Date: Jun. 25, 2021

(87) PCT Pub. No.: WO2020/156128

PCT Pub. Date: Aug. 6, 2020

(65) Prior Publication Data

US 2022/0065871 A1 Mar. 3, 2022

Related U.S. Application Data

(60) Provisional application No. 62/798,229, filed on Jan. 29, 2019.

(51) Int. Cl.
*G01N 33/68* (2006.01)
*C12Q 1/6883* (2018.01)

(52) U.S. Cl.
CPC ....... *G01N 33/6893* (2013.01); *C12Q 1/6883* (2013.01); *G01N 2333/705* (2013.01)

(58) Field of Classification Search
CPC ......... G01N 33/6893; G01N 2333/705; G01N 2333/4709; G01N 2800/085; C12Q 1/6883; C12Q 2600/158
See application file for complete search history.

(56) References Cited

FOREIGN PATENT DOCUMENTS

| | | |
|---|---|---|
| CN | 104774914 A | 7/2015 |
| CN | 107904303 A | 4/2018 |
| CN | 108267585 A | 7/2018 |

OTHER PUBLICATIONS

International Search Report in PCT/CN2020/071742, mailed Apr. 13, 2020, 5 pages.

Borroni et al., "Predicting cognitive decline in Alzheimer disease: Role of platelet amyloid precursor protein," Alzheimer Disease & Associated Disorders. Jan. 1, 2004;18(1):32-4.

Ning et al., "Research Advances of Blood Biomarkers for Biliary Atresia," Chin J Pedaitr Surg, vol. 38, No. 11, Nov. 30, 2017, pp. 869-873.

Padovani et al., "Amyloid precursor protein in platelets: a peripheral marker for the diagnosis of sporadic AD," Neurology. Dec. 26, 2001;57(12):2243-8.

Xu et al., β-amyloid Precusor Protein Exporession Level in Peripheral Platelets in Patients With Parkinson's Disease and Dementia, Chinese general Practice, vol. 18, No. 21, Jul. 31, 2015, pp. 2507-2510.

*Primary Examiner* — Iqbal H Chowdhury

(74) *Attorney, Agent, or Firm* — Kilpatrick Townsend & Stockton LLP

(57) ABSTRACT

Provided are novel diagnostic and prognostic methods for biliary atresia using amyloid precursor protein.

15 Claims, 2 Drawing Sheets

Specification includes a Sequence Listing.

Figure 1 PCA plot for liver biopsies RNA-seq analysis

AMYLOID PRECURSOR PROTEIN AS A DIAGNOSTIC MARKER FOR BILIARY ATRESIA

SEQUENCE LISTING

A Sequence Listing conforming to the rules of for Application filed prior to Jul. 1, 2022 is hereby incorporated by reference. Said Sequence Listing has been filed as an electronic document via the USPTO patent electronic filing system in ASCII formatted text. The electronic document, created on May 17, 2025 is entitled "104525-1253597-000310US_ST25", and is 82,065 bytes in size.

BACKGROUND

Biliary atresia is a disease of the liver and bile ducts that occurs in infants. Typically, symptoms of biliary atresia appear or develop about two to eight weeks after birth. Cells within the liver produce bile, a digestive liquid that helps digest fat. It also carries waste products from the liver to the intestines for excretion. This network of channels and ducts in which bile is produced, digests fat, and eventually moves to intestines is called the biliary system. Under the normal physiological conditions, the biliary system allows the bile to drain from the liver into the intestines. When a baby has biliary atresia, however, bile flow from the liver to the gallbladder is blocked. This causes the bile to be trapped inside the liver, which can quickly cause damage and scarring of the liver cells, resulting in liver cirrhosis and eventually liver failure.

While the exact cause of biliary atresia is yet to be fully illustrated, it is believed that some infants develop biliary atresia due to their bile ducts not formed properly during pregnancy. For most other children with biliary atresia, their bile ducts may be damaged by the body's immune system in response to a viral infection acquired after birth. Although biliary atresia is a rare disease, it affects the Asian population at a notably higher rate than other ethnicities. Diagnosis of biliary atresia relies on blood tests, ultrasound of the abdomen, liver biopsy, as well as diagnostic surgery (which may include an operative cholangiogram). Once diagnosed, biliary atresia is treated by Kasai procedure or hepatoportoenterostomy. With a 65-85% success rate routinely achieved by this procedure, failure still can result in a small percentage of infants, who will then likely require a liver transplant for long term survival. Because of this life-threatening potential of biliary atresia, there exists an urgent need for new and more reliable methods for the early diagnosis of infants suspected of having biliary atresia and for risk assessment among those who have undergone Kasai operation. This invention fulfills this and other related needs.

SUMMARY OF THE INVENTION

The present inventors observed increased expression of amyloid precursor protein in the liver tissue of an infant who is at risk of developing biliary atresia or is suffering from biliary atresia and has a poor outcome of biliary atresia treatment by Kasai operation. This discovery thus allows new methods to be devised for use in the diagnosis or prognosis of biliary atresia.

In the first aspect, the present invention provides a method for diagnosing or assessing the risk of biliary atresia (BA) in an infant by detecting in a liver sample taken from the infant the level of amyloid precursor protein (APP). The method includes these steps: (i) determining the expression level of APP in a liver sample taken from the infant; (ii) detecting an increase in the APP expression level in comparison to a standard control level; and (iii) determining the infant as having BA or at an increased risk of developing biliary atresia.

In some embodiments, the APP expression level is APP mRNA level or protein level. In some embodiments, step (i) comprises a reverse transcription polymerase chain reaction (RT-PCR) or an immunoassay. In some embodiments, the liver sample is a liver biopsy. In some embodiments, the method further includes after step (iii) a step of performing at least one additional diagnostic test for BA to confirm the diagnosis. In some embodiments, the method may further include after step (iii) a step of treating the infant with Kasai procedure.

In the second aspect, the present invention provides a method for assessing the likelihood of poor outcome (e.g., ineffective Kasai procedure) in an infant after the infant has been diagnosed with BA and has received Kasai operation. The method includes these steps: (i) determining the expression level of APP in a liver sample taken from the infant; (ii) detecting an increase in the APP expression level in comparison to a standard control level; and (iii) determining that the Kasai procedure is likely a failure.

In some embodiments, the APP expression level is APP mRNA level or protein level. In some embodiments, step (i) comprises a reverse transcription polymerase chain reaction (RT-PCR) or an immunoassay. In some embodiments, the liver sample is a liver biopsy. In some embodiments, the method further includes after step (iii) a step of performing at least one additional diagnostic test for BA to confirm the prognosis-if the additional test for BA indicates presence of BA, one may conclude the treatment has likely failed. In some embodiments, the method may further include after step (iii) a step of providing the infant with further treatment such as liver transplant.

In a third aspect, the present invention provides a kit for diagnosing BA, assessing risk of developing BA, or prognosing unsuccessful Kasai procedure in an infant. The kit comprises a first container containing at least one reagent for detecting the mRNA or protein level of APP and a second container containing a standard control sample having an average level of APP expression in healthy liver tissue.

In some embodiments, the APP expression level is APP mRNA level or APP protein level. In some embodiments, the first container contains one or more reagents for an RT-PCR. In some embodiments, the first container contains one or more reagents for an immunoassay. In some embodiments, one or more reagents contained in the first container include a set of primers for PCR. In some embodiments, one or more reagents contained in the first container include an antibody against APP. In some embodiments, the kit further includes user instructions for using the kit.

DEFINITIONS

Figure 1:
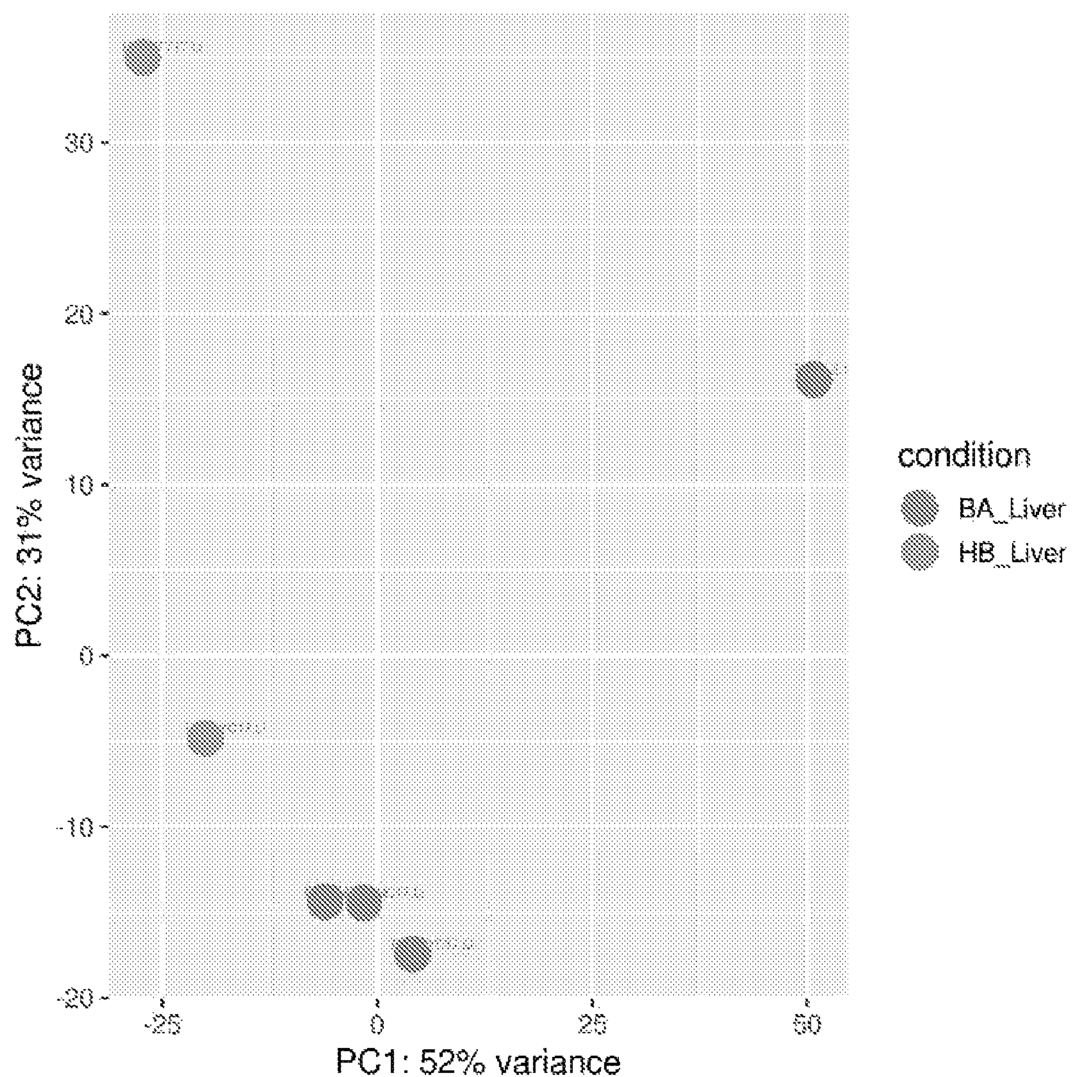
FIG. 1. Principal component analysis of control and BA liver.

As used herein, an "amyloid precursor protein (APP)" refers to a membrane protein encoded by a gene located on chromosome 21 (in human). A highly conserved protein found in many species, there are several known isoforms of human APP due to alternative splicing, ranging in length from 639 to 770 amino acids, with certain isoforms preferentially expressed in neurons. An integral membrane protein expressed in many tissues and concentrated in the synapses of neurons, APP has been implicated as a regulator of synapse formation, neural plasticity, and iron export, although its precise functions are yet to be fully understood. The term "amyloid precursor protein" or "APP" is used herein to broadly encompass any isoforms of the protein such as naturally occurring homologues or orthologues or mutants, including proteins or peptides derived from the full-length APP such as peptides generated by its proteolysis, for instance, beta amyloid (Aβ), a polypeptide containing about 37 to about 49 amino acid residues, whose amyloid fibrillar form is the primary component of amyloid plaques found in the brains of Alzheimer's disease patients. Preferably, an APP is specifically recognized by an antibody that specifically recognizes the full-length APP, e.g., a polypeptide encoded by any one of the polynucleotide sequences set forth in Table 3.

Biliary atresia (BA) is a disease of blocked biliary system in the liver and bile ducts that typically occurs in infants in the age range of 2 weeks to 2 months. Symptoms of biliary atresia include jaundice, dark urine, acholic stools (clay-colored stools), weight loss and irritability. The preferred treatment method for BA is the Kasai procedure or operation, a surgical bypass procedure that allows bile to drain from the liver thus avoiding permanent damage to the liver. As used herein, a subject suffering from BA is an infant (for examples, aged about 1 week or about 2 weeks or about 3 weeks to about 1 month or about 2 months or about 3 months) who has been diagnosed with BA but is yet to receive the Kasai operation, or who has been diagnosed with BA, received the Kasai operation, yet still has symptoms relevant to the disease despite having received the Kasai operation.

In this disclosure the term "biological sample" or "sample" includes sections of tissues such as biopsy and autopsy samples, and frozen sections taken for histologic purposes, or processed forms of any of such samples. Biological samples include blood and blood fractions or products (e.g., serum, plasma, platelets, red blood cells, and the like), sputum or saliva, lymph and tongue tissue, oral swab, cultured cells, e.g., primary cultures, explants, transformed cells, stool, urine, and biopsy taken from a pre-selected organ or tissue (such as liver cells or hepatic tissue sample) as well as cells or tissue derived from biopsy. A biological sample is typically obtained from a eukaryotic organism, which may be a mammal, may be a primate and may be a human subject.

The term "nucleic acid" or "polynucleotide" refers to deoxyribonucleotides or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.*, 19:5081 (1991); Ohtsuka et al., *J. Biol. Chem.*, 260:2605-2608 (1985); and Cassol et al., (1992); Rossolini et al., *Mol. Cell. Probes*, 8:91-98 (1994)). The terms nucleic acid and polynucleotide are used interchangeably with gene, cDNA, and mRNA encoded by a gene.

The terms "polypeptide," "peptide," and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full length proteins (i.e., antigens), wherein the amino acid residues are linked by covalent peptide bonds.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. "Amino acid mimetics" refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

A "polynucleotide hybridization method" as used herein refers to a method for detecting the presence and/or quantity of a pre-determined polynucleotide sequence based on its ability to form Watson-Crick base-pairing, under appropriate hybridization conditions, with a polynucleotide probe of a known sequence. Examples of such hybridization methods include Southern blot, Northern blot, and in situ hybridization.

"Primers" as used herein refer to oligonucleotides that can be used in an amplification method, such as a polymerase chain reaction (PCR), to amplify a nucleotide sequence based on the polynucleotide sequence corresponding to a gene of interest, e.g., the polynucleotide sequence encoding an APP or a derivative thereof. Typically at least one, possibly two, of the PCR primers for amplification of a polynucleotide sequence is sequence-specific for that polynucleotide sequence. The exact length of the primer will depend upon many factors, including temperature, source of the primer, and the method used. For example, for diagnostic and prognostic applications, depending on the complexity of the target sequence, the oligonucleotide primer typically contains at least 10, or 15, or 20, or 25 or more nucleotides, although it may contain fewer nucleotides or more nucleotides. The factors involved in determining the appropriate length of primer are readily known to one of ordinary skill in the art. The primers used in particular embodiments may be designed to specifically amplify a coding sequence for an APP or its variant or derivative. Also, the primers may be designed for specifically amplify only one segment of the APP coding sequence for a fragment of APP. In this disclosure the term "primer pair" means a pair of primers that hybridize to opposite strands a target DNA molecule or to regions of the target DNA which flank a nucleotide sequence to be amplified (e.g., encoding an APP for the purpose of detection such as for assessing BA risk or disease prospect, especially after Kasai operation). In this disclosure the term "primer site" means the area of the target DNA or other nucleic acid to which a primer hybridizes.

A "label," "detectable label," or "detectable moiety" is a composition detectable by spectroscopic, photochemical, biochemical, immunochemical, chemical, or other physical means. For example, useful labels include radioactive isotopes, fluorescent dyes, electron-dense reagents, enzymes (e.g., as commonly used in an ELISA), biotin, digoxigenin, or haptens and proteins that can be made detectable, e.g., by incorporating a radioactive component into the peptide or used to detect antibodies specifically reactive with the peptide. Typically a detectable label is attached to a probe or a molecule with defined binding characteristics (e.g., a polypeptide with a known binding specificity or a polynucleotide), so as to allow the presence of the probe (and therefore its binding target, e.g., a coding sequence for an APP or a fragment or variant thereof) to be readily detectable.

The term "treat" or "treating," as used in this application, describes to an act that leads to the elimination, reduction, alleviation, reversal, or prevention or delay of onset or recurrence of any symptom of a relevant condition (e.g., BA). In other words, "treating" a condition encompasses both therapeutic and prophylactic intervention against the condition: for example, upon testing positive to have elevated APP expression either at mRNA or protein level, an infant will be given additional diagnostic tests (such as blood tests, ultrasound of the abdomen, liver biopsy, as well as diagnostic surgery, which may include an operative cholangiogram) and, upon confirmation of the diagnosis of BA, undergoes therapeutic or prophylactic regimen under the supervision of a medical professional including Kasai operation. For an infant who has received treatment for BA by Kasai operation but still has BA symptoms without improvement or even with worsening symptoms, subsequent treatment will likely require liver transplant depending on physicians' decision upon careful monitoring of the infant. Administration of steroids and/or antibiotics may serve as additional/adjuvant treatment post-Kasai operation with an aim to slow down or halt further inflammation.

The term "effective amount" as used herein refers to an amount of a given substance that is sufficient in quantity to produce a desired effect. For example, when an effective amount of a therapeutic agent for treating BA by way of suppressing or eliminating the expression and/or activity of APP especially in an infant's liver is administered to the infant, the symptoms of BA are reduced, reversed, eliminated, prevented, or delayed of the onset in the infant. An amount adequate to accomplish this is defined as the "therapeutically effective dose" when administration takes place after BA symptoms have become detectable, or is defined as the "prophylactically effective dose" when administration takes place before any symptom has arisen. The dosing range varies with the nature of the therapeutic agent being administered and other factors such as the route of administration and the severity of a patient's BA and related condition.

The term "subject" or "subject in need of treatment," as used herein, includes individuals who seek medical attention due to risk of, or actual suffering from, biliary atresia. Subjects also include individuals currently undergoing therapy that seek manipulation of the therapeutic regimen. Subjects or individuals in need of treatment include those that demonstrate symptoms of biliary atresia, or those at are at risk of suffering from biliary atresia or its symptoms, or those have been tested positive for amyloid precursor protein expression but may not may not have any known risk and/or may or may not have any potentially relevant symptoms. For example, subjects in need of treatment include individuals with a genetic predisposition or family history for biliary atresia, those that are acutely suffering from relevant symptoms, those that have been exposed to a triggering substance or event, as well as those have received treatment for BA (e.g., Kasai operation) but are continuing to suffer from symptoms of the condition. A subject in need of treatment for BA may be any gender and typically an infant at the age of 3 months or younger, for example, between about 1 week to about 3 months, or between about 2 weeks to about 2 months.

The term "about" when used in reference to a predetermined value denotes a range encompassing ±10% of the value.

DETAILED DESCRIPTION

I. General

The present invention relates to the detection of APP expression in the liver cells or tissue of infants who are suffering from or at risk of suffering from biliary atresia, or who are at risk of suffering from undesirable clinical outcome after receiving the Kasai operation. This invention thus provides methods for diagnosis of biliary atresia and prognosis for clinical outcome post-Kasai operation in infants based on detection of APP expression in a liver sample obtained from infants suspected of suffering from biliary atresia or having undergone the Kasai procedure.

Basic texts disclosing general methods and techniques in the field of recombinant genetics include Sambrook and Russell, *Molecular Cloning, A Laboratory Manual* (3rd ed. 2001); Kriegler, *Gene Transfer and Expression: A Laboratory Manual* (1990); and Ausubel et al., eds., *Current Protocols in Molecular Biology* (1994).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from sequenced proteins, from derived amino acid sequences, or from published protein sequences.

Oligonucleotides that are not commercially available can be chemically synthesized, e.g., according to the solid phase phosphoramidite triester method first described by Beaucage & Caruthers, *Tetrahedron Lett.* 22:1859-1862 (1981), using an automated synthesizer, as described in Van Devanter et. al., *Nucleic Acids Res.* 12:6159-6168 (1984). Purification of oligonucleotides is performed using any art-recognized strategy, e.g., native acrylamide gel electrophoresis or anion-exchange HPLC as described in Pearson & Reanier, *J. Chrom.* 255:137-149 (1983).

The polynucleotide sequence encoding a polypeptide of interest, e.g., an amyloid precursor protein or a variant or derivative thereof, and synthetic oligonucleotides can be verified after cloning or subcloning using, e.g., the chain termination method for sequencing double-stranded templates of Wallace et al., *Gene* 16:21-26 (1981).

II. Acquisition of Samples and Analysis of mRNA

The present invention relates to detecting the expression level of APP, either at the mRNA or protein level, in the liver cells or tissue taken from an infant suspected of suffering from biliary atresia (BA) or an infant who has been diagnosed with BA and has received the Kasai operation, as a means to detect the presence of BA, to assess the risk of developing of BA, and/or to provide prognosis of BA treatment such as the Kasai operation in an infant, so as to allow the correct treatment and/or follow-up strategies after Kasai operation. Thus, the first steps of practicing this invention are to obtain an appropriate sample from a test subject and extract mRNA from the sample.

A. Acquisition and Preparation of Samples

An appropriate sample such as a liver cell or tissue sample obtained from an infant, who may or may not exhibit BA symptoms, to be tested or monitored for BA or treatment outcome using a method of the present invention. Collection of a liver biopsy sample from an individual is performed in accordance with the standard protocol hospitals or clinics generally follow. An appropriate amount of tissue sample, including biopsy samples, is collected and may be stored according to standard procedures prior to further preparation.

B. Extraction of RNA

There are numerous methods for extracting RNA from a biological sample. The general methods of RNA preparation (e.g., described by Sambrook and Russell, *Molecular Cloning: A Laboratory Manual* 3d ed., 2001) can be followed; various commercially available reagents or kits, such as Trizol reagent (Invitrogen, Carlsbad, CA), Oligotex Direct mRNA Kits (Qiagen, Valencia, CA), RNeasy Mini Kits (Qiagen, Hilden, Germany), and PolyATtract® Series 9600™ (Promega, Madison, WI), may also be used to obtain RNA from a liver sample from an infant. Combinations of more than one of these methods may also be used.

It is preferable in some applications that all or most of the contaminating DNA be eliminated from the RNA preparations. Thus, careful handling of the samples, thorough treatment with DNase, and proper negative controls in the amplification and quantification steps should be used.

C. PCR-Based Quantitative Determination of RNA Level

Once RNA is extracted from a biological sample, the amount of RNA derived from a genetic locus of interest, e.g., and encoding for a protein of interest such as APP, may be quantified. The preferred method for determining the RNA level is an amplification-based method, e.g., by PCR.

Prior to the amplification step, a DNA copy (cDNA) of the RNA of interest must be synthesized. This is achieved by reverse transcription, which can be carried out as a separate step, or in a homogeneous reverse transcription-polymerase chain reaction (RT-PCR), a modification of the polymerase chain reaction for amplifying RNA. Methods suitable for PCR amplification of ribonucleic acids are described by Romero and Rotbart in *Diagnostic Molecular Biology: Principles and Applications* pp. 401-406; Persing et al., eds., Mayo Foundation, Rochester, MN, 1993; Egger et al., *J. Clin. Microbiol.* 33:1442-1447, 1995; and U.S. Pat. No. 5,075,212.

The general methods of PCR are well known in the art and are thus not described in detail herein. For a review of PCR methods, protocols, and principles in designing primers, see, e.g., Innis, et al., *PCR Protocols: A Guide to Methods and Applications*, Academic Press, Inc. N.Y., 1990. PCR reagents and protocols are also available from commercial vendors, such as Roche Molecular Systems.

PCR is most usually carried out as an automated process with a thermostable enzyme. In this process, the temperature of the reaction mixture is typically cycled through a denaturing region, a primer annealing region, and an extension reaction region automatically. In some protocols, the annealing region and the extension reaction region are merged. Machines specifically adapted for this purpose are commercially available.

Although PCR amplification of the target RNA is typically used in practicing the present invention. One of skill in the art will recognize, however, that amplification of these RNA species in a maternal blood sample may be accomplished by any known method, such as ligase chain reaction (LCR), transcription-mediated amplification, and self-sustained sequence replication or nucleic acid sequence-based amplification (NASBA), each of which provides sufficient amplification. More recently developed branched-DNA technology may also be used to quantitatively determining the amount of RNA markers in maternal blood. For a review of branched-DNA signal amplification for direct quantitation of nucleic acid sequences in clinical samples, see Nolte, Adv. *Clin. Chem.* 33:201-235, 1998.

C. Other Quantitative Methods

The RNA species of interest (such as the APP mRNA) can also be detected using other standard techniques, well-known to those of skill in the art. Although the detection step is typically preceded by an amplification step, amplification is not required in the methods of the invention. For instance, the RNA species of interest may be identified by size fractionation (e.g., gel electrophoresis), whether or not proceeded by an amplification step. After running a sample in an agarose or polyacrylamide gel and labeling with ethidium bromide according to well-known techniques (see, e.g., Sambrook and Russell, supra), the presence of a band of the same size as the standard control is an indication of the presence of a target RNA, the amount of which may then be compared to the control based on the intensity of the band. Alternatively, oligonucleotide probes specific to RNA transcribed from a genetic locus, e.g., the APP gene, can be used to detect the presence of such RNA species and indicate the amount of RNA in comparison to the standard control, based on the intensity of signal imparted by the probe.

Sequence-specific probe hybridization is a well-known method of detecting a particular nucleic acid comprising other species of nucleic acids. Under sufficiently stringent hybridization conditions, the probes hybridize specifically only to substantially complementary sequences. The stringency of the hybridization conditions can be relaxed to tolerate varying amounts of sequence mismatch.

A number of hybridization formats are well-known in the art, including but not limited to, solution phase, solid phase, or mixed phase hybridization assays. The following articles provide an overview of the various hybridization assay formats: Singer et al., *Biotechniques* 4:230, 1986; Haase et al., *Methods in Virology*, pp. 189-226, 1984; Wilkinson, *In situ Hybridization*, Wilkinson ed., IRL Press, Oxford University Press, Oxford; and Hames and Higgins eds., *Nucleic Acid Hybridization: A Practical Approach*, IRL Press, 1987.

The hybridization complexes are detected according to well-known techniques and the detection is not a critical aspect of the present invention. Nucleic acid probes capable of specifically hybridizing to a target nucleic acid, i.e., the APP mRNA species or the amplified DNA, can be labeled by any one of several methods typically used to detect the presence of hybridized nucleic acids. One common method of detection is the use of autoradiography using probes labeled with $^{3}H$, $^{125}I$, $^{35}S$, $^{14}C$, or $^{32}P$, or the like. The choice of radioactive isotope depends on research preferences due to ease of synthesis, stability, and half-lives of the selected isotopes. Other labels include compounds (e.g., biotin and digoxigenin), which bind to antiligands or antibodies labeled with fluorophores, chemiluminescent agents, and enzymes. Alternatively, probes can be conjugated directly with labels such as fluorophores, chemiluminescent agents or enzymes. The choice of label depends on sensitivity required, ease of conjugation with the probe, stability requirements, and available instrumentation.

The probes and primers necessary for practicing the present invention can be synthesized and labeled using well known techniques. Oligonucleotides used as probes and primers may be chemically synthesized according to the solid phase phosphoramidite triester method first described by Beaucage and Caruthers, *Tetrahedron Letts.,* 22:1859-1862, 1981, using an automated synthesizer, as described in Needham-VanDevanter et al., *Nucleic Acids Res.* 12:6159-6168, 1984. Purification of oligonucleotides is by either native acrylamide gel electrophoresis or by anion-exchange high performance liquid chromatography (HPLC) as described in Pearson and Regnier, *J. Chrom.,* 255:137-149, 1983.

III. Immunoassays for Detection of Amyloid Precursor Protein

One aspect of this invention provides immunoassays used in the detection of APP in order to determine the expression level of the protein for the purpose of diagnosis and prognosis of BA. Antibodies against APP described herein are useful for carrying out these immunological assays.

A. Production of Antibodies Against APP

Methods for producing polyclonal and monoclonal antibodies that react specifically with an immunogen of interest are known to those of skill in the art (see, e.g., Coligan, *Current Protocols in Immunology Wiley*/Greene, NY, 1991; Harlow and Lane, *Antibodies: A Laboratory Manual* Cold Spring Harbor Press, NY, 1989; Stites et al. (eds.) *Basic and Clinical Immunology* (4th ed.) Lange Medical Publications, Los Altos, CA, and references cited therein; Goding, *Monoclonal Antibodies: Principles and Practice* (2d ed.) Academic Press, New York, NY, 1986; and Kohler and Milstein *Nature* 256:495-497, 1975). Such techniques include antibody preparation by selection of antibodies from libraries of recombinant antibodies in phage or similar vectors (see, Huse et al., *Science* 246:1275-1281, 1989; and Ward et al., *Nature* 341:544-546, 1989).

In order to produce antisera containing antibodies with desired specificity, the polypeptide of interest (e.g., APP) or an antigenic fragment thereof can be used to immunize suitable animals, e.g., mice, rabbits, or primates. A standard adjuvant, such as Freund's adjuvant, can be used in accordance with a standard immunization protocol. Alternatively, a synthetic antigenic peptide derived from that particular polypeptide can be conjugated to a carrier protein and subsequently used as an immunogen.

The animal's immune response to the immunogen preparation is monitored by taking test bleeds and determining the titer of reactivity to the antigen of interest. When appropriately high titers of antibody to the antigen are obtained, blood is collected from the animal and antisera are prepared. Further fractionation of the antisera to enrich antibodies specifically reactive to the antigen and purification of the antibodies can be performed subsequently, see, Harlow and Lane, supra, and the general descriptions of protein purification provided above.

Monoclonal antibodies are obtained using various techniques familiar to those of skill in the art. Typically, spleen cells from an animal immunized with a desired antigen are immortalized, commonly by fusion with a myeloma cell (see, Kohler and Milstein, *Eur. J. Immunol.* 6:511-519, 1976). Alternative methods of immortalization include, e.g., transformation with Epstein Barr Virus, oncogenes, or retroviruses, or other methods well known in the art. Colonies arising from single immortalized cells are screened for production of antibodies of the desired specificity and affinity for the antigen, and the yield of the monoclonal antibodies produced by such cells may be enhanced by various techniques, including injection into the peritoneal cavity of a vertebrate host.

Additionally, monoclonal antibodies may also be recombinantly produced upon identification of nucleic acid sequences encoding an antibody with desired specificity or a binding fragment of such antibody by screening a human B cell cDNA library according to the general protocol outlined by Huse et al., supra. The general principles and methods of recombinant polypeptide production discussed above are applicable for antibody production by recombinant methods.

B. Immunoassays for APP

Once antibodies specific for APP are available, the expression of APP at protein level in a sample, e.g., a liver cell or tissue sample, can be measured by a variety of immunoassay methods providing qualitative and quantitative results to a skilled artisan. For a review of immunological and immunoassay procedures in general see, e.g., Stites, supra; U.S. Pat. Nos. 4,366,241; 4,376,110; 4,517,288; and 4,837,168.

1. Labeling in Immunoassays

Immunoassays often utilize a labeling agent to specifically bind to and label the binding complex formed by the antibody and the target protein (e.g., APP). The labeling agent may itself be one of the moieties comprising the antibody/target protein complex, or may be a third moiety, such as another antibody, that specifically binds to the antibody/target protein complex. A label may be detectable by spectroscopic, photochemical, biochemical, immunochemical, electrical, optical or chemical means. Examples include, but are not limited to, magnetic beads (e.g., Dynabeads™), fluorescent dyes (e.g., fluorescein isothiocyanate, Texas red, rhodamine, and the like), radiolabels (e.g., $^{3}H$, $^{125}I$, $^{35}S$, $^{14}C$, or $^{32}P$), enzymes (e.g., horse radish peroxidase, alkaline phosphatase, and others commonly used in an ELISA), and colorimetric labels such as colloidal gold or colored glass or plastic (e.g., polystyrene, polypropylene, latex, etc.) beads.

In some cases, the labeling agent is a second antibody bearing a detectable label. Alternatively, the second antibody may lack a label, but it may, in turn, be bound by a labeled third antibody specific to antibodies of the species from which the second antibody is derived. The second antibody can be modified with a detectable moiety, such as biotin, to which a third labeled molecule can specifically bind, such as enzyme-labeled streptavidin.

Other proteins capable of specifically binding immunoglobulin constant regions, such as protein A or protein G, can also be used as the label agents. These proteins are normal constituents of the cell walls of streptococcal bacteria. They exhibit a strong non-immunogenic reactivity with immunoglobulin constant regions from a variety of species (see, generally, Kronval, et al. *J. Immunol.,* 111:1401-1406 (1973); and Akerstrom, et al., *J. Immunol.,* 135:2589-2542 (1985)).

2. Immunoassay Formats

Immunoassays for detecting a target protein of interest (e.g., APP) from samples may be either competitive or noncompetitive. Noncompetitive immunoassays are assays in which the amount of captured target protein is directly measured. In one preferred "sandwich" assay, for example, the antibody specific for the target protein can be bound directly to a solid substrate where the antibody is immobilized. It then captures the target protein in test samples. The antibody/target protein complex thus immobilized is then bound by a labeling agent, such as a second or third antibody bearing a label, as described above.

In competitive assays, the amount of target protein in a sample is measured indirectly by measuring the amount of an added (exogenous) target protein displaced (or competed away) from an antibody specific for the target protein by the target protein present in the sample. In a typical example of such an assay, the antibody is immobilized and the exogenous target protein is labeled. Since the amount of the exogenous target protein bound to the antibody is inversely proportional to the concentration of the target protein present in the sample, the target protein level in the sample can thus be determined based on the amount of exogenous target protein bound to the antibody and thus immobilized.

In some cases, western blot (immunoblot) analysis is used to detect and quantify the presence of APP in the samples. The technique generally comprises separating sample proteins by gel electrophoresis on the basis of molecular weight, transferring the separated proteins to a suitable solid support (such as a nitrocellulose filter, a nylon filter, or a derivatized nylon filter) and incubating the samples with the antibodies that specifically bind the target protein. These antibodies may be directly labeled or alternatively may be subsequently detected using labeled antibodies (e.g., labeled sheep anti-mouse antibodies) that specifically bind to the antibodies against APP.

Other assay formats include liposome immunoassays (LIA), which use liposomes designed to bind specific molecules (e.g., antibodies) and release encapsulated reagents or markers. The released chemicals are then detected according to standard techniques (see, Monroe et al., *Amer. Clin. Prod. Rev.,* 5:34-41 (1986)).

For these immunoassays, the patient being tested may be an infant who is at risk of developing BA or may be one who has been diagnosed with BA, has undergone treatment such as Kasai operation, and is now being assessed for likelihood of a desirable outcome of the treatment.

IV. Treatment Options

One practical application of this invention is intended for early detection of BA among infants who are suspected of suffering from the disease or are at increased risk of developing the disease. Once they are tested according to any one of the methods of this invention and are determined as at risk of suffering from or later developing this disease, they can be subject to additional diagnostic tests, such as blood tests, ultrasound of the abdomen, liver biopsy, and diagnostic surgery (which may include an operative cholangiogram) in order to confirm whether they indeed suffer from the disease. Upon confirmation of the diagnosis of BA, they can then undergo appropriate treatment (e.g., the Kasai operation) as prescribed by their attending physician.

Another application is intended for predicting the likelihood of success among infants who have been diagnosed with BA and have been given appropriate treatment such as the Kasai operation. As it is known that a minority of all infant BA patients who underwent the operation will fail to properly recover, and the symptoms and damaging effects of BA will continue and even worsen. The claimed method of this invention allows physicians to quickly obtain an assessment of the likelihood of treatment outcome (e.g., shortly after the Kasai procedure such as 1 day, 2 days, 3 days, 4 days, 5 days, 6 days, 7 days, or up to 10 days or 2 weeks post-operation) when the infant may or may not yet to show any signs of persistent or deteriorating BA symptoms: whether it will result in desirable outcome, where the infant patient will fully recover from the disease, or it will result in failure, where the infant patient will require additional treatment, such as another Kasai procedure or even liver transplant.

A further aspect of the present invention is the treatment of BA. Since the expression of APP, both at mRNA level and at protein level, has been found to increase in the liver of infants who suffer from BA, or who are at increased risk of later developing BA while exhibiting no BA symptoms for the time being, or who have been diagnosed with BA and given appropriate treatment such as the Kasai procedure but suffer from undesirable outcome (i.e., failure of treatment to alleviate BA symptoms and damages to liver), one treatment method for BA is to target APP by suppressing its expression (both at mRNA and protein level) and/or activity. For instance, specific inhibitors targeting APP expression and/or activity may be administered to an infant who suffers from BA, or who is at heightened risk of later developing BA, or who has received a diagnosis of BA and received treatment (e.g., the Kasai procedure) but is at risk of suffering from treatment failure. Such specific inhibitors include a broad spectrum of possible compounds of distinct chemical and structural features such as a dominant negative APP mutant or its encoding nucleic acid, a nucleic acid encoding an antisense or miRNA, miniRNA, long non-coding RNA targeting APP, an inactivating anti-APP antibody, small chemicals, peptides, proteins, natural extract compounds from herbs, etc., and they are useful in both prophylactic and therapeutic applications for treating BA. Also, APP expression may be suppressed by genetic manipulation techniques including CRISPR.

V. Establishing Standard Controls

For the application of this invention for the purpose of diagnosing BA or assessing risk of developing BA at a later time, in order to establish a standard control, a group of healthy infants without any liver disorders, especially BA, should first be selected before liver samples are obtained. These infants should be of similar age, which is within the appropriate time frame (for example, aged from about 2 weeks to about 8 weeks) when infants may be tested using the methods of the present invention. The health status of the selected infants should be confirmed by well established, routinely employed methods including but not limited to blood tests and abdominal ultrasound.

The selected group of healthy infants must be of a reasonable size, such that the average amount of APP mRNA and protein found in the liver tissue samples (e.g., liver biopsy) calculated from the group can be reasonably regarded as representative of the normal or average amount among the general population of healthy infants not suffering from BA and not at heightened risk of developing BA. Preferably, the selected group comprises at least 10 healthy infants.

For the application of this invention for the purpose of providing a prognosis of BA treatment (especially the Kasai procedure) outcome among infants who have already been diagnosed with BA and received appropriate treatment such as the Kasai procedure, the same standard control described above may be used. In the alternative, a slightly different standard control can be established: a group of infants who suffered from BA and have undergone the same BA treatment such as Kasai operation and successfully recovered should be selected for collection of liver samples. Similar to the description above, these infants should be of similar age and make up a group of a reasonable size, e.g., at least 10 in the group.

Once an average value is established for the amount of APP mRNA or protein based on the individual values found in the liver tissue of each infant of the selected group, this value is considered a standard control value for APP mRNA or protein. Any liver tissue sample that contains a similar amount of APP mRNA or protein can thus be used as a standard control sample.

VI. Kits

The invention also provides kits for detecting APP mRNA or protein, especially in a liver sample taken from an infant, according to the method of the present invention for the purpose of detecting the presence of BA, assessing the risk of later developing BA, or assessing likelihood of a successful BA treatment (such as the Kasai operation) outcome. The kits typically include a first container that contains a first container containing at least one, possibly more, reagent for detecting expression level of APP and a second container containing a composition having a standard control level of APP expression (or a standard control sample). The one or more reagents in the first container may be used for measuring APP mRNA level, such as oligonucleotide primers useful for RT-PCR and/or oligonucleotide probe(s) for specific hybridization with an APP-specific polynucleotide sequence. Other possible reagents may include the necessary enzyme(s) and buffer(s) for performing assays to detect APP mRNA such as RT-PCR or nucleotide hybridization.

For the purpose of determining the APP protein level in a liver sample, the one or more reagents contained in the first container may be those useful for immunoassays capable of specifically detecting and quantifying APP level as a protein, such as ELISA or western blot analysis. One useful reagent is an anti-APP antibody, which may be a polyclonal antibody or a monoclonal antibody capable of specific binding to APP. Further included may be a secondary antibody, for example, an antibody against the anti-APP antibody, preferably conjugated with a detectable label.

In addition, the kit may further include informational material containing instructions for a user on how to use the kit for performing an assay and determining whether increased APP mRNA or protein is present in a patient sample.

EXAMPLES

The following examples are provided by way of illustration only and not by way of limitation. Those of skill in the art will readily recognize a variety of non-critical parameters that could be changed or modified to yield essentially the same or similar results.

Example 1: Amyloid Precursor Protein Expression in Biliary Atresia

This study reveals, for the first time, the specific expression of amyloid precursor protein and/or its processed forms in the bile duct of livers in patients suffering from biliary atresia (BA). This discovery allows one to devise new and reliable diagnostic methods for early detection of BA as well as for predicting the therapeutic outcome of BA treatment such as Kasai operation.

Introduction

Biliary atresia (BA [OMIM 210500]) is characterized by progressive fibro-obliterative cholangiopathy (disease of the bile duct) affecting both the intra- and extra-hepatic bile ducts and resulting in obstructive bile flow, cholestasis, and jaundice in neonates. BA occurs in some infants two to six weeks after birth, and symptoms of BA are usually evident between two and six weeks after birth, in that babies with BA develop progressive cholestasis, a condition in which the liver is unable to excrete bilirubin through the bile ducts in the form of bile. Bilirubin builds up inside of liver and begins to accumulate in the blood, causing symptoms including yellowing of the skin, itchiness, poor absorption of nutrients, pale stools, dark urine, and a swollen abdomen.

The differential diagnosis of BA allows for identification of patients suffering from BA as opposed to other disorders such as neonatal cholestasis (NC) like neonatal hepatitis (NH), paucity of interlobular bile ducts (PILBD), progressive familial intrahepatic cholestasis (PFIC), and various metabolic diseases like galactosemia and a-1 antitrypsin deficiency. The most important objective in such cases is to distinguish obstructive cholestasis from non-obstructive causes. The diagnosis of BA, particularly distinguishing it from other causes of liver injury in the neonatal period, is challenging as there is a high degree of overlap in clinical, biochemical, imaging, and histological characteristics of BA and other causes of NC.

Without surgical treatment (Kasai operation) to re-establish the bile drainage from microscopic residual bile ductules within the liver, progressive hepatic fibrosis leads to cirrhosis, portal vein hypertension, liver failure and death by the age of two (1, 2). However, postsurgical complications, including cholangitis (50%) and portal hypertension (>60%), remain a problem (3-7). Furthermore, regardless of drainage after successful surgery, patients will often develop inflammation and sclerosis of the biliary tree, leading to secondary biliary cirrhosis. To these patients and those who failed the surgical intervention, liver transplantation becomes the only treatment option. Indeed, BA has been the most common indication for liver transplantation during childhood for the past 20 years. Due to liver graft scarcity, many patients die before transplantation.

Urgently, there exists a distinct need to address the following problems: first, diagnosis of BA needs to be improved, in particular at early stages of the disease. The optimal age for Kasai operation is 60-75 days; delayed in diagnosis and surgery will lead to poor outcome. In fact, early diagnosis allows the family and surgeon for better planning of disease management. Second, despite the same Kasai operation, the outcome can vary from patient to patient, suggesting the existence of subsets of patient but there are no reliable markers for prognosis to guide stratified treatments for optimal outcomes. Third, regardless of drainage after Kasai operation, patients will often develop bile duct inflammation and sclerosis, leading to secondary biliary cirrhosis. To these patients and those who failed surgery, liver transplantation is the only option. For those BA patients who are predicted to have poor outcome after Kasai operation may be selected to undergo liver transplantation as the treatment from the start without first undergoing Kasai operation. There is an urgent need to find new and effective therapies that ameliorate BA.

Materials and Methods

Liver Tissues

Control liver: "Quasi-normal" human liver tissues were obtained from non-tumour margin of hepatoblastoma (HB). BA liver: Liver biopsies of BA patients taken during Kasai operation or at transplantation. All tissues were obtained during operations with full informed consent from parents or patients, and the study was approved by Hong Kong West Cluster-Hong Kong University Cluster Research Ethics Committee/Institutional Review Board (UW 16-052).

Antibodies

Anti-β-Amyloid (4G8; Biolegend) reacts to precursor forms, as well as abnormally processed isoforms of amyloid precursor protein. Anti-CK19 (ab52625; abcam) reacts to human cytokeratin 19.

Liver Biopsies

Wedge biopsies (50×50 mm) were obtained from non-syndromic BA patients during laparoscopic cholangiography, hepatoblastoma (HB)).

RNA Sequencing of Liver Tissues

Total RNAs were prepared from 30 mg of control livers (HB; n=2) and BA livers (n=4) using RNeasy Mini Kit (Qiagen) following manufacturer's protocol. Reverse transcription, amplification of 50 ng total RNA of each liver samples, and library construction were performed using single cell RNA-seq technology (Smart-seq 2.0) with minor modifications (8). Qualities of the pre-amplified products of normal and BA livers were confirmed to be optimal by Bioanalyzer. Library construction was performed using Nextera XT Kit following manufacturer's protocol. Libraries were pooled and sequenced by pair ends of 100 base pairs (PE100) on illumina HiSeq 2500 System.

Immuno-Fluorescence Staining

Tissues were fixed in 4% paraformaldehyde (w/v) in PBS (phosphate-buffered saline, pH 7.2) for 48 h at 4° C., dehydrated in graded series of alcohol, cleared in xylene before being embedded in paraffin. Sections (8 μm in thickness) were prepared, mounted onto TESPA-coated microscope glass. Sections were dewaxed in xylene, hydrated in a graded series of alcohol and finally in distilled water. Antigen was retrieved by two steps: (i) incubating in 70% Formic acid for 10 minutes and washing in water; (ii) incubating in 10 mM sodium citrate buffer (pH 6.0) at 95° C. for 10 min and washing in water. After blocking in PBS-T (PBS with 0.1% Triton) supplemented with 1% Bovine Serum Albumin for 1 h at room temperature, sections were incubated with anti-β-Amyloid (4G8, 1:200; Biolegend) and anti-CK19 (ab52625, 1:250; abcam) diluted in PBS-T/BSA for overnight at 4° C. After washing in PBS-T, sections were incubated with appropriate fluorescent tagged secondary antibodies in PBS-T/BSA at 37° C. for 1 h. After PBS-T washings, sections were mounted in Dapi-containing anti-fade mounting fluid. Images were taken with Nikon Eclipse 80i microscope mounted with SPOT RT3 microscope digital camera under fluorescence illumination. Photos were compiled using Adobe Photoshop 7.

Results

Transcriptome Analysis of Normal and BA Liver by RNAseq

The RNA-seq reads were first subjected to quality check using FastQC version 0.11.1. Further the adapter contamination and low-quality regions were filtered using Cutadapt version 1.8.3 with the parameter −q=33 and retained only reads with length≥30. The percentage of high quality bases in the filtered raw reads were greater than 90% for all the samples, with the quality score cut-off=20. Subsequently, sequencing reads were filtered for rRNA sequence by aligning to human rRNA sequences using Bowtie 2 (default parameters). The remaining reads were mapped to the reference genome. The transcriptome mapping/alignment and identification of exon-exon splice junctions with the human genome reference (GRCh38, downloaded from Ensembl database) was done by using TopHat version 2.0.10 (default parameters). All the samples had an overall alignment of >80% with human reference. Counting of aligned reads per gene were done using HTSeq version 0.9.1 for further differential expression analysis. The counts for each gene per samples were presented as table in DESeq2 to accurately detect significant differentially expressed genes across the conditions. Visualization was done using R and Bioconductor (FIG. 5*c*?).

Principal component analysis (PCA) of liver biopsies revealed the following observations:

1. Normal liver and BA liver displayed distinctive molecular signatures.
2. The two normal liver controls showed differences among themselves, which may indicate the genetic differences between the patients or the tissue stages during isolation.
3. Three of the BA livers were clustering very closely to each other while the other patient showed enormous difference, which may indicate progression of disease.

TABLE 1

| Pathways involvement of the 1558 differentially expressed genes | |
|---|---|
| Integrin signalling pathway (P00034) | 28 |
| Gonadotropin-releasing hormone receptor pathway (P06664) | 25 |
| Inflammation mediated by chemokine and cytokine signaling pathway (P00031) | 21 |
| CCKR signaling map (P06959) | 20 |
| Wnt signaling pathway (P00057) | 17 |
| Angiogenesis (P00005) | 12 |
| PDGF signaling pathway (P00047) | 12 |
| Apoptosis signaling pathway (P00006) | 11 |
| Nicotinic acetylcholine receptor signaling pathway (P00044) | 10 |
| Huntington disease (P00029) | 9 |
| Alzheimer disease-presenilin pathway (P00004) | 8 |
| Heterotrimeric G-protein signaling pathway-Gq alpha and Go alpha mediated pathway (P00027) | 8 |
| Heterotrimeric G-protein signaling pathway-Gi alpha and Gs alpha mediated pathway (P00026) | 8 |
| Parkinson disease (P00049) | 7 |

TABLE 1-continued

| Pathways involvement of the 1558 differentially expressed genes | |
|---|---|
| Interleukin signaling pathway (P00036) | 7 |
| EGF receptor signaling pathway (P00018) | 7 |
| T cell activation (P00053) | 6 |
| TGF-beta signaling pathway (P00052) | 6 |
| FGF signaling pathway (P00021) | 6 |
| FAS signaling pathway (P00020) | 6 |
| Cadherin signaling pathway (P00012) | 6 |
| B cell activation (P00010) | 6 |
| Axon guidance mediated by Slit/Robo (P00008) | 5 |
| Toll receptor signaling pathway (P00054) | 5 |
| Oxidative stress response (P00046) | 5 |
| Muscarinic acetylcholine receptor 1 and 3 signaling pathway (P00042) | 5 |
| Insulin/IGF pathway-protein kinase B signaling cascade (P00033) | 5 |
| Insulin/IGF pathway-mitogen activated protein kinase kinase/MAP kinase cascade (P00032) | 5 |
| Dopamine receptor mediated signaling pathway (P05912) | 5 |
| Pyrimidine Metabolism (P02771) | 5 |
| Endothelin signaling pathway (P00019) | 5 |
| Blood coagulation (P00011) | 5 |
| Adrenaline and noradrenaline biosynthesis (P00001) | 4 |
| De novo purine biosynthesis (P02738) | 4 |
| PI3 kinase pathway (P00048) | 4 |
| Notch signaling pathway (P00045) | 4 |
| Muscarinic acetylcholine receptor 2 and 4 signaling pathway (P00043) | 4 |
| Nicotine degradation (P05914) | 4 |
| 5-Hydroxytryptamine degredation (P04372) | 4 |
| Axon guidance mediated by semaphorins (P00007) | 3 |
| Alpha adrenergic receptor signaling pathway (P00002) | 3 |
| Ubiquitin proteasome pathway (P00060) | 3 |
| p53 pathway (P00059) | 3 |
| Formyltetrahydroformate biosynthesis (P02743) | 3 |
| Plasminogen activating cascade (P00050) | 3 |
| Synaptic vesicle trafficking (P05734) | 3 |
| Metabotropic glutamate receptor group III pathway (P00039) | 3 |
| Ionotropic glutamate receptor pathway (P00037) | 3 |
| Thyrotropin-releasing hormone receptor signaling pathway (P04394) | 3 |
| 2-arachidonoylglycerol biosynthesis (P05726) | 3 |
| Serine glycine biosynthesis (P02776) | 3 |
| Nicotine pharmacodynamics pathway (P06587) | 3 |
| Cytoskeletal regulation by Rho GTPase (P00016) | 3 |
| Purine metabolism (P02769) | 3 |
| 5HT2 type receptor mediated signaling pathway (P04374) | 3 |
| Axon guidance mediated by netrin (P00009) | 2 |
| Pyridoxal-5-phosphate biosynthesis (P02759) | 2 |
| Alzheimer disease-amyloid secretase pathway (P00003) | 2 |
| Heme biosynthesis (P02746) | 2 |
| VEGF signaling pathway (P00056) | 2 |
| Tetrahydrofolate biosynthesis (P02742) | 2 |
| De novo pyrimidine ribonucleotides biosythesis (P02740) | 2 |
| Androgen/estrogene/progesterone biosynthesis (P02727) | 2 |
| JAK/STAT signaling pathway (P00038) | 2 |
| Vitamin B6 metabolism (P02787) | 2 |
| p53 pathway by glucose deprivation (P04397) | 2 |
| Hypoxia response via HIF activation (P00030) | 2 |
| Vitamin D metabolism and pathway (P04396) | 2 |
| Ras Pathway (P04393) | 2 |
| Oxytocin receptor mediated signaling pathway (P04391) | 2 |
| p38 MAPK pathway (P05918) | 2 |
| Hedgehog signaling pathway (P00025) | 2 |
| Glycolysis (P00024) | 2 |
| General transcription by RNA polymerase I (P00022) | 2 |
| Pyruvate metabolism (P02772) | 2 |
| Histamine H1 receptor mediated signaling pathway (P04385) | 2 |
| Cortocotropin releasing factor receptor signaling pathway (P04380) | 2 |
| Circadian clock system (P00015) | 2 |
| 5HT4 type receptor mediated signaling pathway (P04376) | 2 |
| 5HT3 type receptor mediated signaling pathway (P04375) | 2 |
| 5HT1 type receptor mediated signaling pathway (P04373) | 2 |
| Toll pathway-drosophila (P06217) | 1 |
| SCW signaling pathway (P06216) | 1 |
| GBB signaling pathway (P06214) | 1 |
| DPP signaling pathway (P06213) | 1 |
| DPP-SCW signaling pathway (P06212) | 1 |
| BMP/activin signaling pathway-drosophila (P06211) | 1 |
| N-acetylglucosamine metabolism (P02756) | 1 |
| Methylmalonyl pathway (P02755) | 1 |
| Methionine biosynthesis (P02753) | 1 |
| Leucine biosynthesis (P02749) | 1 |

TABLE 1-continued

| Pathways involvement of the 1558 differentially expressed genes | |
|---|---|
| Isoleucine biosynthesis (P02748) | 1 |
| mRNA splicing (P00058) | 1 |
| Histidine biosynthesis (P02747) | 1 |
| Transcription regulation by bZIP transcription factor (P00055) | 1 |
| Fructose galactose metabolism (P02744) | 1 |
| De novo pyrimidine deoxyribonucleotide biosynthesis (P02739) | 1 |
| Metabotropic glutamate receptor group I pathway (P00041) | 1 |
| Asparagine and aspartate biosynthesis (P02730) | 1 |
| Metabotropic glutamate receptor group II pathway (P00040) | 1 |
| GABA-B receptor II signaling (P05731) | 1 |
| Alanine biosynthesis (P02724) | 1 |
| Interferon-gamma signaling pathway (P00035) | 1 |
| Adenine and hypoxanthine salvage pathway (P02723) | 1 |
| p53 pathway feedback loops 2 (P04398) | 1 |
| Valine biosynthesis (P02785) | 1 |
| Threonine biosynthesis (P02781) | 1 |
| P53 pathway feedback loops 1 (P04392) | 1 |
| Bupropion degradation (P05729) | 1 |
| Heterotrimeric G-protein signaling pathway-rod outer segment phototransduction (P00028) | 1 |
| Opioid proopiomelanocortin pathway (P05917) | 1 |
| Sulfate assimilation (P02778) | 1 |
| Opioid prodynorphin pathway (P05916) | 1 |
| Succinate to proprionate conversion (P02777) | 1 |
| Opioid proenkephalin pathway (P05915) | 1 |
| General transcription regulation (P00023) | 1 |
| Salvage pyrimidine ribonucleotides (P02775) | 1 |
| Salvage pyrimidine deoxyribonucleotides (P02774) | 1 |
| Angiotensin II-stimulated signaling through G proteins and beta-arrestin (P05911) | 1 |
| Pyridoxal phosphate salvage pathway (P02770) | 1 |
| DNA replication (P00017) | 1 |
| Cholesterol biosynthesis (P00014) | 1 |
| Beta3 adrenergic receptor signaling pathway (P04379) | 1 |
| Beta2 adrenergic receptor signaling pathway (P04378) | 1 |
| Beta1 adrenergic receptor signaling pathway (P04377) | 1 |

TABLE 2

List of amyloid pathway genes being differentially expressed

| Gene id | $\log_2$ Fold Change |
|---|---|
| A2M | −1.13 |
| ADAM9 | 1.53 |
| APBB3 | 0.98 |
| APH1B | 2.06 |
| APOL1 | −1.66 |
| ATP2A3 | 1.89 |
| CAPN1 | 1.13 |
| FAS | −1.98 |
| FSTL1 | 0.96 |
| ITPR3 | 2.22 |
| LPL | 2.74 |
| MMP19 | 3.21 |
| MMP2 | 2.76 |
| MMP7 | 5.75 |
| NDUFA6 | −1.57 |
| NDUFB1 | −0.78 |
| NDUFB3 | −0.75 |
| NDUFV3 | −0.86 |
| NOTCH3 | 2.66 |
| TCF3 | 1.34 |
| TTR | −2.11 |

Genes Involved in Amyloid Precursor Protein (APP) Metabolism were Differentially Expressed in BA Liver Pathway analysis for differentially expressed genes (1558) were done using PANTHER (website: www.pantherdb.org/), KEGG Mapper (https://www.genome.jp/kegg/mapper.html), DAVID (website: david.ncifcrf.gov/) and also from literatures. Among the list of pathways (Table 1), apart from hormonal and metabolic pathways, few disease related pathways were observed. Alzheimer disease presenilin and amyloid secretase pathway genes (10 nos.) were observed from panther pathways. KEGG pathway analysis also revealed few more genes to be involved in amyloid pathway genes from whole liver RNA-seq analysis. There were a total of 21 genes from total differentially expressed genes involved in amyloid pathway. The list of 21 genes along with log 2FoldChange are displayed in Table 2. Among which, MMP7 (Matrilysin, involved in amyloid-presenilin pathway) being the highest upregulated gene (log 2FoldChange=5.752) among the total (1558) differentially expressed genes.

Expression of APP and its Processed Forms in BA Liver

Figure 2:
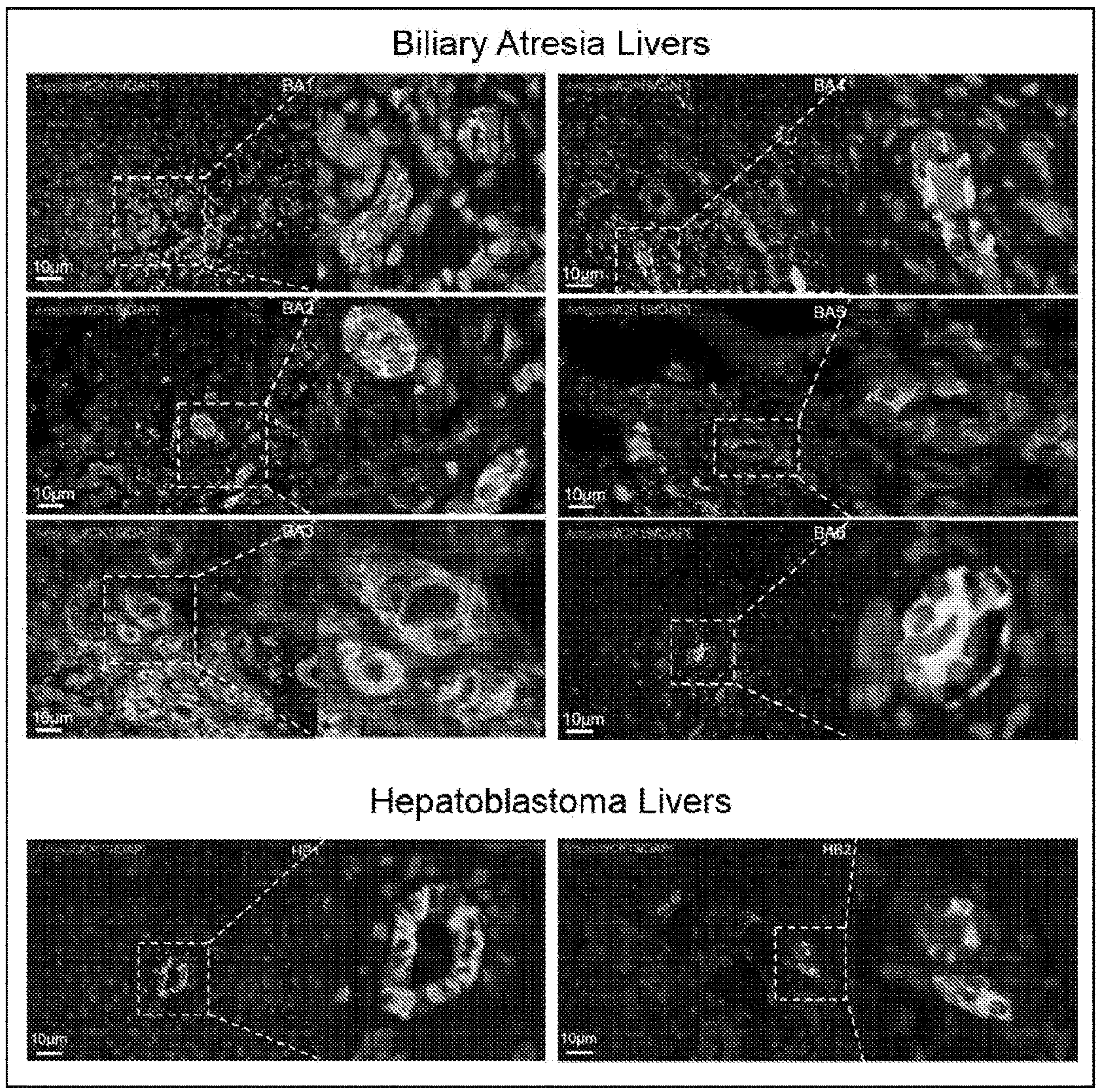
FIG. 2. Expression of APP in BA bile ducts. Sections of livers of biliary atresia (A) and normal controls (B; Hepatoblastoma) were immuno-fluorescent stained for APP (red) and CK19 (green; bile duct marker). Photos of liver sections of six BA patients (BA1 to BA6) and two HB patients (HB1 and HB2) were shown for comparison. Regions highlighted were enlarged and shown on the right.

Immuno-fluorescence analysis for APP on liver sections of BA (n=18) and control (HB, n=5; CC, n=13; CS, n=2) patients revealed elevated expression of APP and/or its processed forms in the bile ducts of all the BA livers but not in all the control livers (FIG. 2).

All patents, patent applications, and other publications, including GenBank Accession Numbers or equivalent sequence identification numbers, cited in this application are incorporated by reference in the entirety of their contents for all purposes.

TABLE 3

| APP_transcrips_final | | |
|---|---|---|
| Number of variants | Ensembl_protein_id/ UniProt_id | Fasta_Formatted_DNA_sequences_with_cufflinks_ transcript_ids_and_corres-ponding_Ensembl_ids |
| 1 | ENSP00000284981 | >TCONS_00180767\|ENST00000346798 (SEQ ID NO: 1)<br>GGTACCCACTGATGGTAATGCTGGCCTGCTGGCTGAACC<br>CCAGATTGCCATGTTCTGTGGCAGACTGAACATGCACAT<br>GAATGTCCAGAATGGGAAGTGGGATTCAGATCCATCAGG<br>GACCAAAACCTGCATTGATACCAAGGAAGGCATCCTGCA<br>GTATTGCCAAGAAGTCTACCCTGAACTGCAGATCACCAAT<br>GTGGTAGAAGCCAACCAACCAGTGACCATCCAGAACTGG<br>TGCAAGCGGGGCCGCAAGCAGTGCAAGACCCATCCCCA<br>CTTTGTGATTCCCTACCGCTGCTTAGTTGGTGAGTTTGTA<br>AGTGATGCCCTTCTCGTTCCTGACAAGTGCAAATTCTTAC<br>ACCAGGAGAGGATGGATGTTTGCGAAACTCATCTTCACT<br>GGCACACCGTCGCCAAAGAGACATGCAGTGAGAAGAGTA<br>CCAACTTGCATGACTACGGCATGTTGCTGCCCTGCGGAA<br>TTGACAAGTTCCGAGGGGTAGAGTTTGTGTGTTGCCCAC<br>TGGCTGAAGAAAGTGACAATGTGGATTCTGCTGATGCGG<br>AGGAGGATGACTCGGATGTCTGGTGGGGCGGAGCAGAC<br>ACAGACTATGCAGATGGGAGTGAAGACAAAGTAGTAGAA<br>GTAGCAGAGGAGGAAGAAGTGGCTGAGGTGGAAGAAGA<br>AGAAGCCGATGATGACGAGGACGATGAGGATGGTGATGA<br>GGTAGAGGAAGAGGCTGAGGAACCCTACGAAGAAGCCA<br>CAGAGAGAACCACCAGCATTGCCACCACCACCACCACCA<br>CCACAGAGTCTGTGGAAGAGGTGGTTCGAGAGGTGTGCT<br>CTGAACAAGCCGAGACGGGGCCGTGCCGAGCAATGATC<br>TCCCGCTGGTACTTTGATGTGACTGAAGGGAAGTGTGCC<br>CCATTCTTTTACGGCGGATGTGGCGGCAACCGGAACAAC<br>TTTGACACAGAAGAGTACTGCATGGCCGTGTGTGGCAGC<br>GCCATGTCCCAAAGTTTACTCAAGACTACCCAGGAACCTC<br>TTGCCCGAGATCCTGTTAAACTTCCTACAACAGCAGCCAG<br>TACCCCTGATGCCGTTGACAAGTATCTCGAGACACCTGG<br>GGATGAGAATGAACATGCCCATTTCCAGAAAGCCAAAGA<br>GAGGCTTGAGGCCAAGCACCGAGAGAGAATGTCCCAGG<br>TCATGAGAGAATGGGAAGAGGCAGAACGTCAAGCAAAGA<br>ACTTGCCTAAAGCTGATAAGAAGGCAGTTATCCAGCATTT<br>CCAGGAGAAAGTGGAATCTTTGGAACAGGAAGCAGCCAA<br>CGAGAGACAGCAGCTGGTGGAGACACACATGGCCAGAG<br>TGGAAGCCATGCTCAATGACCGCCGCCGCCTGGCCCTG<br>GAGAACTACATCACCGCTCTGCAGGCTGTTCCTCCTCGG<br>CCTCGTCACGTGTTCAATATGCTAAAGAAGTATGTCCGCG<br>CAGAACAGAAGGACAGACAGCACACCCTAAAGCATTTCG<br>AGCATGTGCGCATGGTGGATCCCAAGAAAGCCGCTCAGA<br>TCCGGTCCCAGGTTATGACACACCTCCGTGTGATTTATGA<br>GCGCATGAATCAGTCTCTCTCCCTGCTCTACAACGTGCCT<br>GCAGTGGCCGAGGAGATTCAGGATGAAGTTGATGAGCTG<br>CTTCAGAAAGAGCAAAACTATTCAGATGACGTCTTGGCCA<br>ACATGATTAGTGAACCAAGGATCAGTTACGGAAACGATG<br>CTCTCATGCCATCTTTGACCGAAACGAAAACCACCGTGG<br>AGCTCCTTCCCGTGAATGGAGAGTTCAGCCTGGACGATC<br>TCCAGCCGTGGCATTCTTTTGGGGCTGACTCTGTGCCAG<br>CCAACACAGAAAACGAAGTTGAGCCTGTTGATGCCCGCC<br>CTGCTGCCGACCGAGGACTGACCACTCGACCAGGTTCTG<br>GGTTGACAAATATCAAGACGGAGGAGATCTCTGAAGTGA<br>AGATGGATGCAGAATTCCGACATGACTCAGGATATGAAG<br>TTCATCATCAAAAATTGGTGTTCTTTGCAGAAGATGTGGG<br>TTCAAACAAAGGTGCAATCATTGGACTCATGGTGGGCGG<br>TGTTGTCATAGCGACAGTGATCGTCATCACCTTGGTGATG<br>CTGAAGAAGAAACAGTACACATCCATTCATCATGGTGTGG<br>TGGAGGTTGACGCCGCTGTCACCCCAGAGGAGCGCCAC<br>CTGTCCAAGATGCAGCAGAACGGCTACGAAAATCCAACC<br>TACAAGTTCTTTGAGCAGATGCAGAACTAGACCCCCGCC<br>ACAGCAGCCTCTGAAGTTGGACAGCAAAACCATTGCTTC<br>ACTACCCATCGGTGTCCATTTATAGAATAATGTGGGAAGA<br>AACAAACCCGTTTTATGATTTACTCATTATCGCCTTTTGAC<br>AGCTGTGCTGTAACACAAGTAGATGCCTGAACTTGAATTA<br>ATCCACACATCAGTAATGTATTCTATCTCTCTTTACATTTT<br>GGTCTCTATACTACATTATTAATGGGTTTTGTGTACTGTAA<br>AGAATTTAGCTGTATCAAACTAGTGCATGAATAGATTCTCT<br>CCTGATTATTTATCACATAGCCCCTTAGCCAGTTGTATATT<br>ATTCTTGTGGTTTGTGACCCAATTAAGTCCTACTTTACATA<br>TGCTTTAAGAATCGATGGGGGATGCTTCATGTGAACGTG<br>GGAGTTCAGCTGCTTCTCTTGCCTAAGTATTCCTTTCCTG<br>ATCACTATGCATTTTAAAGTTAAACATTTTTAAGTATTTCA<br>GATGCTTTAGAGAGATTTTTTTTCCATGACTGCATTTTACT<br>GTACAGATTGCTGCTTCTGCTATATTTGTGATATAGGAATT<br>AAGAGGATACACACGTTTGTTTCTTCGTGCCTGTTTTATG<br>TGCACACATTAGGCATTGAGACTTCAAGCTTTTCTTTTTTT |

TABLE 3-continued

| APP_transcrips_final | | |
|---|---|---|
| Number of variants | Ensembl_protein_id/ UniProt_id | Fasta_Formatted_DNA_sequences_with_cufflinks_ transcript_ids_and_corres-ponding_Ensembl_ids |
| | | GTCCACGTATCTTTGGGTCTTTGATAAAGAAAAGAATCCC<br>TGTTCATTGTAAGCACTTTTACGGGGGGGGTGGGGAGGG<br>GTGCTCTGCTGGTCTTCAATTACCAAGAATTCTCCAAAAC<br>AATTTTCTGCAGGATGATTGTACAGAATCATTGCTTATGA<br>CATGATCGCTTTCTACACTGTATTACATAAATAAATTAAAT<br>AAAATAACCCCGGGCAAGACTTTTCTTTGAAGGATGACTA<br>CAGACATTAAATAATCGAAGTAATTTTGGGTGGGGAGAAG<br>AGGCAGATTCAATTTTCTTTAACCAGTCTGAAGTTTCATTT<br>ATGATACAAAAGAAGATGAAAATGGAAGTGGCAATATAAG<br>GGGATGAGGAAGGCATGCCTGGACAAACCCTTCTTTTAA<br>GATGTGTCTTCAATTTGTATAAAATGGTGTTTTCATGTAAA<br>TAAATACATTCTTGGAGGAGCACCATTG |
| 2 | ENSP00000284981 | >TCONS_00180768\|ENST00000346798 (SEQ ID NO: 2)<br>ATTGAGTGAAGATTAAGACGGAGAAGATGGCGCCTCTGC<br>AGTGCAGCAAAGAAAAGCTGTGTGGAGGCTGCAGCCTAG<br>TGAAATCCACCCACCACTAGGTACCCACTGATGGTAATG<br>CTGGCCTGCTGGCTGAACCCCAGATTGCCATGTTCTGTG<br>GCAGACTGAACATGCACATGAATGTCCAGAATGGGAAGT<br>GGGATTCAGATCCATCAGGGACCAAAACCTGCATTGATA<br>CCAAGGAAGGCATCCTGCAGTATTGCCAAGAAGTCTACC<br>CTGAACTGCAGATCACCAATGTGGTAGAAGCCAACCAAC<br>CAGTGACCATCCAGAACTGGTGCAAGCGGGGCCGCAAG<br>CAGTGCAAGACCCATCCCCACTTTGTGATTCCCTACCGCT<br>GCTTAGTTGGTGAGTTTGTAAGTGATGCCCTTCTCGTTCC<br>TGACAAGTGCAAATTCTTACACCAGGAGAGGATGGATGTT<br>TGCGAAACTCATCTTCACTGGCACACCGTCGCCAAAGAG<br>ACATGCAGTGAGAAGAGTACCAACTTGCATGACTACGGC<br>ATGTTGCTGCCCTGCGGAATTGACAAGTTCCGAGGGGTA<br>GAGTTTGTGTGTTGCCCACTGGCTGAAGAAAGTGACAAT<br>GTGGATTCTGCTGATGCGGAGGAGGATGACTCGGATGTC<br>TGGTGGGGCGGAGCAGACACAGACTATGCAGATGGGAG<br>TGAAGACAAAGTAGTAGAAGTAGCAGAGGAGGAAGAAGT<br>GGCTGAGGTGGAAGAAGAAGAAGCCGATGATGACGAGG<br>ACGATGAGGATGGTGATGAGGTAGAGGAAGAGGCTGAG<br>GAACCCTACGAAGAAGCCACAGAGAGAACCACCAGCATT<br>GCCACCACCACCACCACCACCACAGAGTCTGTGGAAGAG<br>GTGGTTCGAGAGGTGTGCTCTGAACAAGCCGAGACGGG<br>GCCGTGCCGAGCAATGATCTCCCGCTGGTACTTTGATGT<br>GACTGAAGGGAAGTGTGCCCCATTCTTTTACGGCGGATG<br>TGGCGGCAACCGGAACAACTTTGACACAGAAGAGTACTG<br>CATGGCCGTGTGTGGCAGCGCCATTCCTACAACAGCAGC<br>CAGTACCCCTGATGCCGTTGACAAGTATCTCGAGACACC<br>TGGGGATGAGAATGAACATGCCCATTTCCAGAAAGCCAA<br>AGAGAGGCTTGAGGCCAAGCACCGAGAGAGAATGTCCC<br>AGGTCATGAGAGAATGGGAAGAGGCAGAACGTCAAGCAA<br>AGAACTTGCCTAAAGCTGATAAGAAGGCAGTTATCCAGCA<br>TTTCCAGGAGAAAGTGGAATCTTTGGAACAGGAAGCAGC<br>CAACGAGAGACAGCAGCTGGTGGAGACACACATGGCCA<br>GAGTGGAAGCCATGCTCAATGACCGCCGCCGCCTGGCC<br>CTGGAGAACTACATCACCGCTCTGCAGGCTGTTCCTCCT<br>CGGCCTCGTCACGTGTTCAATATGCTAAAGAAGTATGTCC<br>GCGCAGAACAGAAGGACAGACAGCACACCCTAAAGCATT<br>TCGAGCATGTGCGCATGGTGGATCCCAAGAAAGCCGCTC<br>AGATCCGGTCCCAGGTTATGACACACCTCCGTGTGATTTA<br>TGAGCGCATGAATCAGTCTCTCTCCCTGCTCTACAACGTG<br>CCTGCAGTGGCCGAGGAGATTCAGGATGAAGTTGATGAG<br>CTGCTTCAGAAAGAGCAAAACTATTCAGATGACGTCTTGG<br>CCAACATGATTAGTGAACCAAGGATCAGTTACGGAAACG<br>ATGCTCTCATGCCATCTTTGACCGAAACGAAAACCACCGT<br>GGAGCTCCTTCCCGTGAATGGAGAGTTCAGCCTGGACGA<br>TCTCCAGCCGTGGCATTCTTTTGGGGCTGACTCTGTGCC<br>AGCCAACACAGAAAACGAAGTTGAGCCTGTTGATGCCCG<br>CCCTGCTGCCGACCGAGGACTGACCACTCGACCAGGTTC<br>TGGGTTGACAAATATCAAGACGGAGGAGATCTCTGAAGT<br>GAAGATGGATGCAGAATTCCGACATGACTCAGGATATGA<br>AGTTCATCATCAAAAATTGGTGTTCTTTGCAGAAGATGTG<br>GGTTCAAACAAAGGTGCAATCATTGGACTCATGGTGGGC<br>GGTGTTGTCATAGCGACAGTGATCGTCATCACCTTGGTG<br>ATGCTGAAGAAGAAACAGTACACATCCATTCATCATGGTG<br>TGGTGGAGGTTGACGCCGCTGTCACCCCAGAGGAGCGC<br>CACCTGTCCAAGATGCAGCAGAACGGCTACGAAAATCCA<br>ACCTACAAGTTCTTTGAGCAGATGCAGAACTAGACCCCC<br>GCCACAGCAGCCTCTGAAGTTGGACAGCAAAACCATTGC<br>TTCACTACCCATCGGTGTCCATTTATAGAATAATGTGGGA |

TABLE 3-continued

| APP_transcrips_final | | |
|---|---|---|
| Number of variants | Ensembl_protein_id/ UniProt_id | Fasta_Formatted_DNA_sequences_with_cufflinks_ transcript_ids_and_corres-ponding_Ensembl_ids |
| | | AGAAACAAACCCGTTTTATGATTTACTCATTATCGCCTTTT<br>GACAGCTGTGCTGTAACACAAGTAGATGCCTGAACTTGA<br>ATTAATCCACACATCAGTAATGTATTCTATCTCTCTTTACA<br>TTTTGGTCTCTATACTACATTATTAATGGGTTTTGTGTACT<br>GTAAAGAATTTAGCTGTATCAAACTAGTGCATGAATAGAT<br>TCTCTCCTGATTATTTATCACATAGCCCCTTAGCCAGTTGT<br>ATATTATTCTTGTGGTTTGTGACCCAATTAAGTCCTACTTT<br>ACATATGCTTTAAGAATCGATGGGGGATGCTTCATGTGAA<br>CGTGGGAGTTCAGCTGCTTCTCTTGCCTAAGTATTCCTTT<br>CCTGATCACTATGCATTTTAAAGTTAAACATTTTTAAGTAT<br>TTCAGATGCTTTAGAGAGATTTTTTTTCCATGACTGCATTT<br>TACTGTACAGATTGCTGCTTCTGCTATATTTGTGATATAG<br>GAATTAAGAGGATACACACGTTTGTTTCTTCGTGCCTGTT<br>TTATGTGCACACATTAGGCATTGAGACTTCAAGCTTTTCTT<br>TTTTTGTCCACGTATCTTTGGGTCTTTGATAAAGAAAAGAA<br>TCCCTGTTCATTGTAAGCACTTTTACGGGGGGGGTGGGG<br>AGGGGTGCTCTGCTGGTCTTCAATTACCAAGAATTCTCCA<br>AAACAATTTTCTGCAGGATGATTGTACAGAATCATTGCTTA<br>TGACATGATCGCTTTCTACACTGTATTACATAAATAAATTA<br>AATAAAATAACCCCGGGCAAGACTTTTCTTTGAAGGATGA<br>CTACAGACATTAAATAATCGAAGTAATTTTGGGTGGGGAG<br>AAGAGGCAGATTCAATTTTCTTTAACCAGTCTGAAGTTTC<br>ATTTATGATACAAAAGAAGATGAAAATGGAAGTGGCAATA<br>TAAGGGGATGAGGAAGGCATGCCTGGACAAACCCTTCTT<br>TTAAGATGTGTCTTCAATTTGTATAAAATGGTGTTTTCATG<br>TAAATAAATACATTCTTGGAGGAGCACCATTG |
| 3 | ENSP00000284981 | >TCONS_00180769\|ENST00000346798 (SEQ ID NO: 3)<br>CGCCGCGCTCGGGCTCCGTCAGTTTCCTCGGCAGCGGT<br>AGGCGAGAGCACGCGGAGGAGCGTGCGCGGGGGCCCC<br>GGGAGACGGCGGCGGTGGCGGCGCGGGCAGAGCAAGG<br>ACGCGGCGGATCCCACTCGCACAGCAGCGCACTCGGTG<br>CCCCGCGCAGGGTCGCGATGCTGCCCGGTTTGGCACTG<br>CTCCTGCTGGCCGCCTGGACGGCTCGGGCGCTGGAGGT<br>CTACCCTGAACTGCAGATCACCAATGTGGTAGAAGCCAA<br>CCAACCAGTGACCATCCAGAACTGGTGCAAGCGGGGCC<br>GCAAGCAGTGCAAGACCCATCCCCACTTTGTGATTCCCT<br>ACCGCTGCTTAGTTGGTGAGTTTGTAAGTGATGCCCTTCT<br>CGTTCCTGACAAGTGCAAATTCTTACACCAGGAGAGGAT<br>GGATGTTTGCGAAACTCATCTTCACTGGCACACCGTCGC<br>CAAAGAGACATGCAGTGAGAAGAGTACCAACTTGCATGA<br>CTACGGCATGTTGCTGCCCTGCGGAATTGACAAGTTCCG<br>AGGGGTAGAGTTTGTGTGTTGCCCACTGGCTGAAGAAAG<br>TGACAATGTGGATTCTGCTGATGCGGAGGAGGATGACTC<br>GGATGTCTGGTGGGGCGGAGCAGACACAGACTATGCAG<br>ATGGGAGTGAAGACAAAGTAGTAGAAGTAGCAGAGGAGG<br>AAGAAGTGGCTGAGGTGGAAGAAGAAGAAGCCGATGATG<br>ACGAGGACGATGAGGATGGTGATGAGGTAGAGGAAGAG<br>GCTGAGGAACCCTACGAAGAAGCCACAGAGAGAACCACC<br>AGCATTGCCACCACCACCACCACCACCACAGAGTCTGTG<br>GAAGAGGTGGTTCGAGAGGTGTGCTCTGAACAAGCCGA<br>GACGGGGCCGTGCCGAGCAATGATCTCCCGCTGGTACTT<br>TGATGTGACTGAAGGGAAGTGTGCCCCATTCTTTTACGG<br>CGGATGTGGCGGCAACCGGAACAACTTTGACACAGAAGA<br>GTACTGCATGGCCGTGTGTGGCAGCGCCATGTCCCAAAG<br>TTTACTCAAGACTACCCAGGAACCTCTTGCCCGAGATCCT<br>GTTAAACTTCCTACAACAGCAGCCAGTACCCCTGATGCC<br>GTTGACAAGTATCTCGAGACACCTGGGGATGAGAATGAA<br>CATGCCCATTTCCAGAAAGCCAAAGAGAGGCTTGAGGCC<br>AAGCACCGAGAGAGAATGTCCCAGCCTCGTCACGTGTTC<br>AATATGCTAAAGAAGTATGTCCGCGCAGAACAGAAGGAC<br>AGACAGCACACCCTAAAGCATTTCGAGCATGTGCGCATG<br>GTGGATCCCAAGAAAGCCGCTCAGATCCGGTCCCAGGTT<br>ATGACACACCTCCGTGTGATTTATGAGCGCATGAATCAGT<br>CTCTCTCCCTGCTCTACAACGTGCCTGCAGTGGCCGAGG<br>AGATTCAGGATGAAGTTGATGAGCTGCTTCAGAAAGAGC<br>AAAACTATTCAGATGACGTCTTGGCCAACATGATTAGTGA<br>ACCAAGGATCAGTTACGGAAACGATGCTCTCATGCCATCT<br>TTGACCGAAACGAAAACCACCGTGGAGCTCCTTCCCGTG<br>AATGGAGAGTTCAGCCTGGACGATCTCCAGCCGTGGCAT<br>TCTTTTGGGGCTGACTCTGTGCCAGCCAACACAGAAAAC<br>GAAGTTGAGCCTGTTGATGCCCGCCCTGCTGCCGACCGA<br>GGACTGACCACTCGACCAGGTTCTGGGTTGACAAATATC<br>AAGACGGAGGAGATCTCTGAAGTGAAGATGGATGCAGAA<br>TTCCGACATGACTCAGGATATGAAGTTCATCATCAAAAT |

TABLE 3-continued

| APP_transcrips_final | | |
|---|---|---|
| Number of variants | Ensembl_protein_id/ UniProt_id | Fasta_Formatted_DNA_sequences_with_cufflinks_ transcript_ids_and_corres-ponding_Ensembl_ids |
| | | TGGTGTTCTTTGCAGAAGATGTGGGTTCAAACAAAGGTG<br>CAATCATTGGACTCATGGTGGGCGGTGTTGTCATAGCGA<br>CAGTGATCGTCATCACCTTGGTGATGCTGAAGAAGAAAC<br>AGTACACATCCATTCATCATGGTGTGGTGGAGGTTGACG<br>CCGCTGTCACCCCAGAGGAGCGCCACCTGTCCAAGATG<br>CAGCAGAACGGCTACGAAAATCCAACCTACAAGTTCTTTG<br>AGCAGATGCAGAACTAGACCCCCGCCACAGCAGCCTCTG<br>AAGTTGGACAGCAAAACCATTGCTTCACTACCCATCGGTG<br>TCCATTTATAGAATAATGTGGGAAGAAACAAACCCGTTTT<br>ATGATTTACTCATTATCGCCTTTTGACAGCTGTGCTGTAA<br>CACAAGTAGATGCCTGAACTTGAATTAATCCACACATCAG<br>TAATGTATTCTATCTCTCTTTACATTTTGGTCTCTATACTAC<br>ATTATTAATGGGTTTTGTGTACTGTAAAGAATTTAGCTGTA<br>TCAAACTAGTGCATGAATAGATTCTCTCCTGATTATTTATC<br>ACATAGCCCCTTAGCCAGTTGTATATTATTCTTGTGGTTT<br>GTGACCCAATTAAGTCCTACTTTACATATGCTTTAAGAATC<br>GATGGGGGATGCTTCATGTGAACGTGGGAGTTCAGCTGC<br>TTCTCTTGCCTAAGTATTCCTTTCCTGATCACTATGCATTT<br>TAAAGTTAAACATTTTTAAGTATTTCAGATGCTTTAGAGAG<br>ATTTTTTTTCCATGACTGCATTTTACTGTACAGATTGCTGC<br>TTCTGCTATATTTGTGATATAGGAATTAAGAGGATACACA<br>CGTTTGTTTCTTCGTGCCTGTTTTATGTGCACACATTAGG<br>CATTGAGACTTCAAGCTTTTCTTTTTTTGTCCACGTATCTT<br>TGGGTCTTTGATAAAGAAAAGAATCCCTGTTCATTGTAAG<br>CACTTTTACGGGGGGGGTGGGGAGGGGTGCTCTGCTGG<br>TCTTCAATTACCAAGAATTCTCCAAAACAATTTTCTGCAGG<br>ATGATTGTACAGAATCATTGCTTATGACATGATCGCTTTCT<br>ACACTGTATTACATAAATAAATTAAATAAAATAACCCCGGG<br>CAAGACTTTTCTTTGAAGGATGACTACAGACATTAAATAAT<br>CGAAGTAATTTTGGGTGGGGAGAAGAGGCAGATTCAATT<br>TTCTTTAACCAGTCTGAAGTTTCATTTATGATACAAAAGAA<br>GATGAAAATGGAAGTGGCAATATAAGGGGATGAGGAAGG<br>CATGCCTGGACAAACCCTTCTTTTAAGATGTGTCTTCAAT<br>TTGTATAAAATGGTGTTTTCATGTAAATAAATACATTCTTG<br>GAGGAGCACCATTG |
| 4 | ENSP00000284981 | >TCONS_00180771\|ENST00000346798 (SEQ ID NO: 4)<br>CGCCGCGCTCGGGCTCCGTCAGTTTCCTCGGCAGCGGT<br>AGGCGAGAGCACGCGGAGGAGCGTGCGCGGGGGCCCC<br>GGGAGACGGCGGCGGTGGCGGCGCGGGCAGAGCAAGG<br>ACGCGGCGGATCCCACTCGCACAGCAGCGCACTCGGTG<br>CCCCGCGCAGGGTCGCGATGCTGCCCGGTTTGGCACTG<br>CTCCTGCTGGCCGCCTGGACGGCTCGGGCGCTGGAGGT<br>ACCCACTGATGGTAATGCTGGCCTGCTGGCTGAACCCCA<br>GATTGCCATGTTCTGTGGCAGACTGAACATGCACATGAAT<br>GTCCAGAATGGGAAGTGGGATTCAGATCCATCAGGGACC<br>AAAACCTGCATTGATACCAAGGAAGGCATCCTGCAGTATT<br>GCCAAGAAGTCTACCCTGAACTGCAGATCACCAATGTGG<br>TAGAAGCCAACCAACCAGTGACCATCCAGAACTGGTGCA<br>AGCGGGGCCGCAAGCAGTGCAAGACCCATCCCCACTTT<br>GTGATTCCCTACCGCTGCTTAGTTGGTGAGTTTGTAAGTG<br>ATGCCCTTCTCGTTCCTGACAAGTGCAAATTCTTACACCA<br>GGAGAGGATGGATGTTTGCGAAACTCATCTTCACTGGCA<br>CACCGTCGCCAAAGAGACATGCAGTGAGAAGAGTACCAA<br>CTTGCATGACTACGGCATGTTGCTGCCCTGCGGAATTGA<br>CAAGTTCCGAGGGGTAGAGTTTGTGTGTTGCCCACTGGC<br>TGAAGAAAGTGACAATGTGGATTCTGCTGATGCGGAGGA<br>GGATGACTCGGATGTCTGGTGGGGCGGAGCAGACACAG<br>ACTATGCAGATGGGAGTGAAGACAAAGTAGTAGAAGTAG<br>CAGAGGAGGAAGAAGTGGCTGAGGTGGAAGAAGAAGAA<br>GCCGATGATGACGAGGACGATGAGGATGGTGATGAGGT<br>AGAGGAAGAGGCTGAGGAACCCTACGAAGAAGCCACAG<br>AGAGAACCACCAGCATTGCCACCACCACCACCACCACCA<br>CAGAGTCTGTGGAAGAGGTGGTTCGAGAGGTGTGCTCTG<br>AACAAGCCGAGACGGGGCCGTGCCGAGCAATGATCTCC<br>CGCTGGTACTTTGATGTGACTGAAGGGAAGTGTGCCCCA<br>TTCTTTTACGGCGGATGTGGCGGCAACCGGAACAACTTT<br>GACACAGAAGAGTACTGCATGGCCGTGTGTGGCAGCGC<br>CATTCCTACAACAGCAGCCAGTACCCCTGATGCCGTTGA<br>CAAGTATCTCGAGACACCTGGGGATGAGAATGAACATGC<br>CCATTTCCAGAAAGCCAAAGAGAGGCTTGAGGCCAAGCA<br>CCGAGAGAGAATGTCCCAGGTCATGAGAGAATGGGAAGA<br>GGCAGAACGTCAAGCAAAGAACTTGCCTAAAGCTGATAA<br>GAAGGCAGTTATCCAGCATTTCCAGGAGAAAGTGGAATC<br>TTTGGAACAGGAAGCAGCCAACGAGAGACAGCAGCTGGT |

TABLE 3-continued

| APP_transcrips_final | | |
|---|---|---|
| Number of variants | Ensembl_protein_id/ UniProt_id | Fasta_Formatted_DNA_sequences_with_cufflinks_ transcript_ids_and_corres-ponding_Ensembl_ids |
| | | GGAGACACACATGGCCAGAGTGGAAGCCATGCTCAATGA<br>CCGCCGCCGCCTGGCCCTGGAGAACTACATCACCGCTCT<br>GCAGGCTGTTCCTCCTCGGCCTCGTCACGTGTTCAATAT<br>GCTAAAGAAGTATGTCCGCGCAGAACAGAAGGACAGACA<br>GCACACCCTAAAGCATTTCGAGCATGTGCGCATGGTGGA<br>TCCCAAGAAAGCCGCTCAGATCCGGTCCCAGGTTATGAC<br>ACACCTCCGTGTGATTTATGAGCGCATGAATCAGTCTCTC<br>TCCCTGCTCTACAACGTGCCTGCAGTGGCCGAGGAGATT<br>CAGGATGAAGTTGATGAGCTGCTTCAGAAAGAGCAAAAC<br>TATTCAGATGACGTCTTGGCCAACATGATTAGTGAACCAA<br>GGATCAGTTACGGAAACGATGCTCTCATGCCATCTTTGAC<br>CGAAACGAAAACCACCGTGGAGCTCCTTCCCGTGAATGG<br>AGAGTTCAGCCTGGACGATCTCCAGCCGTGGCATTCTTT<br>TGGGGCTGACTCTGTGCCAGCCAACACAGAAAACGAAGG<br>TTCTGGGTTGACAAATATCAAGACGGAGGAGATCTCTGAA<br>GTGAAGATGGATGCAGAATTCCGACATGACTCAGGATAT<br>GAAGTTCATCATCAAAAATTGGTGTTCTTTGCAGAAGATG<br>TGGGTTCAAACAAAGGTGCAATCATTGGACTCATGGTGG<br>GCGGTGTTGTCATAGCGACAGTGATCGTCATCACCTTGG<br>TGATGCTGAAGAAGAAACAGTACACATCCATTCATCATGG<br>TGTGGTGGAGGTTGACGCCGCTGTCACCCCAGAGGAGC<br>GCCACCTGTCCAAGATGCAGCAGAACGGCTACGAAAATC<br>CAACCTACAAGTTCTTTGAGCAGATGCAGAACTAGACCCC<br>CGCCACAGCAGCCTCTGAAGTTGGACAGCAAAACCATTG<br>CTTCACTACCCATCGGTGTCCATTTATAGAATAATGTGGG<br>AAGAAACAAACCCGTTTTATGATTTACTCATTATCGCCTTT<br>TGACAGCTGTGCTGTAACACAAGTAGATGCCTGAACTTGA<br>ATTAATCCACACATCAGTAATGTATTCTATCTCTCTTTACA<br>TTTTGGTCTCTATACTACATTATTAATGGGTTTTGTGTACT<br>GTAAAGAATTTAGCTGTATCAAACTAGTGCATGAATAGAT<br>TCTCTCCTGATTATTTATCACATAGCCCCTTAGCCAGTTGT<br>ATATTATTCTTGTGGTTTGTGACCCAATTAAGTCCTACTTT<br>ACATATGCTTTAAGAATCGATGGGGGATGCTTCATGTGAA<br>CGTGGGAGTTCAGCTGCTTCTCTTGCCTAAGTATTCCTTT<br>CCTGATCACTATGCATTTTAAAGTTAAACATTTTTAAGTAT<br>TTCAGATGCTTTAGAGAGATTTTTTTTCCATGACTGCATTT<br>TACTGTACAGATTGCTGCTTCTGCTATATTTGTGATATAG<br>GAATTAAGAGGATACACACGTTTGTTTCTTCGTGCCTGTT<br>TTATGTGCACACATTAGGCATTGAGACTTCAAGCTTTTCTT<br>TTTTTGTCCACGTATCTTTGGGTCTTTGATAAAGAAAAGAA<br>TCCCTGTTCATTGTAAGCACTTTTACGGGGGGGGTGGGG<br>AGGGGTGCTCTGCTGGTCTTCAATTACCAAGAATTCTCCA<br>AAACAATTTTCTGCAGGATGATTGTACAGAATCATTGCTTA<br>TGACATGATCGCTTTCTACACTGTATTACATAAATAAATTA<br>AATAAAATAACCCCGGGCAAGACTTTTCTTTGAAGGATGA<br>CTACAGACATTAAATAATCGAAGTAATTTTGGGTGGGGAG<br>AAGAGGCAGATTCAATTTTCTTTAACCAGTCTGAAGTTTC<br>ATTTATGATACAAAAGAAGATGAAAATGGAAGTGGCAATA<br>TAAGGGGATGAGGAAGGCATGCCTGGACAAACCCTTCTT<br>TTAAGATGTGTCTTCAATTTGTATAAAATGGTGTTTTCATG<br>TAAATAAATACATTCTTGGAGGAGCACCATTG |
| 5 | ENSP00000284981 | >TCONS_00180772\|ENST00000346798 (SEQ ID NO: 5)<br>CGCCGCGCTCGGGCTCCGTCAGTTTCCTCGGCAGCGGT<br>AGGCGAGAGCACGCGGAGGAGCGTGCGCGGGGGCCCC<br>GGGAGACGGCGGCGGTGGCGGCGCGGGCAGAGCAAGG<br>ACGCGGCGGATCCCACTCGCACAGCAGCGCACTCGGTG<br>CCCCGCGCAGGGTCGCGATGCTGCCCGGTTTGGCACTG<br>CTCCTGCTGGCCGCCTGGACGGCTCGGGCGCTGGAGGT<br>ACCCACTGATGGTAATGCTGGCCTGCTGGCTGAACCCCA<br>GATTGCCATGTTCTGTGGCAGACTGAACATGCACATGAAT<br>GTCCAGAATGGGAAGTGGGATTCAGATCCATCAGGGACC<br>AAAACCTGCATTGATACCAAGGAAGGCATCCTGCAGTATT<br>GCCAAGAAGTCTACCCTGAACTGCAGATCACCAATGTGG<br>TAGAAGCCAACCAACCAGTGACCATCCAGAACTGGTGCA<br>AGCGGGGCCGCAAGCAGTGCAAGACCCATCCCCACTTT<br>GTGATTCCCTACCGCTGCTTAGTTGGTGAGTTTGTAAGTG<br>ATGCCCTTCTCGTTCCTGACAAGTGCAAATTCTTACACCA<br>GGAGAGGATGGATGTTTGCGAAACTCATCTTCACTGGCA<br>CACCGTCGCCAAAGAGACATGCAGTGAGAAGAGTACCAA<br>CTTGCATGACTACGGCATGTTGCTGCCCTGCGGAATTGA<br>CAAGTTCCGAGGGGTAGAGTTTGTGTGTTGCCCACTGGC<br>TGAAGAAAGTGACAATGTGGATTCTGCTGATGCGGAGGA<br>GGATGACTCGGATGTCTGGTGGGGCGGAGCAGACACAG<br>ACTATGCAGATGGGAGTGAAGACAAAGTAGTAGAAGTAG |

TABLE 3-continued

| APP_transcrips_final | | |
|---|---|---|
| Number of variants | Ensembl_protein_id/ UniProt_id | Fasta_Formatted_DNA_sequences_with_cufflinks_ transcript_ids_and_corres-ponding_Ensembl_ids |
| | | CAGAGGAGGAAGAAGTGGCTGAGGTGGAAGAAGAAGAA<br>GCCGATGATGACGAGGACGATGAGGATGGTGATGAGGT<br>AGAGGAAGAGGCTGAGGAACCCTACGAAGAAGCCACAG<br>AGAGAACCACCAGCATTGCCACCACCACCACCACCACCA<br>CAGAGTCTGTGGAAGAGGTGGTTCGAGAGGTGTGCTCTG<br>AACAAGCCGAGACGGGGCCGTGCCGAGCAATGATCTCC<br>CGCTGGTACTTTGATGTGACTGAAGGGAAGTGTGCCCCA<br>TTCTTTTACGGCGGATGTGGCGGCAACCGGAACAACTTT<br>GACACAGAAGAGTACTGCATGGCCGTGTGTGGCAGCGC<br>CATGTCCCAAAGTTTACTCAAGACTACCCAGGAACCTCTT<br>GCCCGAGATCCTGTTAAACTTCCTACAACAGCAGCCAGT<br>ACCCCTGATGCCGTTGACAAGTATCTCGAGACACCTGGG<br>GATGAGAATGAACATGCCCATTTCCAGAAAGCCAAAGAG<br>AGGCTTGAGGCCAAGCACCGAGAGAGAATGTCCCAGGT<br>CATGAGAGAATGGGAAGAGGCAGAACGTCAAGCAAAGAA<br>CTTGCCTAAAGCTGATAAGAAGGCAGTTATCCAGCATTTC<br>CAGGAGAAAGTGGAATCTTTGGAACAGGAAGCAGCCAAC<br>GAGAGACAGCAGCTGGTGGAGACACACATGGCCAGAGT<br>GGAAGCCATGCTCAATGACCGCCGCCGCCTGGCCCTGG<br>AGAACTACATCACCGCTCTGCAGGCTGTTCCTCCTCGGC<br>CTCGTCACGTGTTCAATATGCTAAAGAAGTATGTCCGCGC<br>AGAACAGAAGGACAGACAGCACACCCTAAAGCATTTOGA<br>GCATGTGCGCATGGTGGATCCCAAGAAAGCCGCTCAGAT<br>CCGGTCCCAGGTTATGACACACCTCCGTGTGATTTATGA<br>GCGCATGAATCAGTCTCTCTCCCTGCTCTACAACGTGCCT<br>GCAGTGGCCGAGGAGATTCAGGATGAAGTTGATGAGCTG<br>CTTCAGAAAGAGCAAAACTATTCAGATGACGTCTTGGCCA<br>ACATGATTAGTGAACCAAGGATCAGTTACGGAAACGATG<br>CTCTCATGCCATCTTTGACCGAAACGAAAACCACCGTGG<br>AGCTCCTTCCCGTGAATGGAGAGTTCAGCCTGGACGATC<br>TCCAGCCGTGGCATTCTTTTGGGGCTGACTCTGTGCCAG<br>CCAACACAGAAAACGAAGGTTCTGGGTTGACAAATATCAA<br>GACGGAGGAGATCTCTGAAGTGAAGATGGATGCAGAATT<br>CCGACATGACTCAGGATATGAAGTTCATCATCAAAAATTG<br>GTGTTCTTTGCAGAAGATGTGGGTTCAAACAAAGGTGCAA<br>TCATTGGACTCATGGTGGGCGGTGTTGTCATAGCGACAG<br>TGATCGTCATCACCTTGGTGATGCTGAAGAAGAAACAGTA<br>CACATCCATTCATCATGGTGTGGTGGAGGTTGACGCCGC<br>TGTCACCCCAGAGGAGCGCCACCTGTCCAAGATGCAGCA<br>GAACGGCTACGAAAATCCAACCTACAAGTTCTTTGAGCAG<br>ATGCAGAACTAGACCCCCGCCACAGCAGCCTCTGAAGTT<br>GGACAGCAAAACCATTGCTTCACTACCCATCGGTGTCCAT<br>TTATAGAATAATGTGGGAAGAAACAAACCCGTTTTATGAT<br>TTACTCATTATCGCCTTTTGACAGCTGTGCTGTAACACAA<br>GTAGATGCCTGAACTTGAATTAATCCACACATCAGTAATG<br>TATTCTATCTCTCTTTACATTTTGGTCTCTATACTACATTAT<br>TAATGGGTTTTGTGTACTGTAAAGAATTTAGCTGTATCAAA<br>CTAGTGCATGAATAGATTCTCTCCTGATTATTTATCACATA<br>GCCCCTTAGCCAGTTGTATATTATTCTTGTGGTTTGTGAC<br>CCAATTAAGTCCTACTTTACATATGCTTTAAGAATCGATGG<br>GGGATGCTTCATGTGAACGTGGGAGTTCAGCTGCTTCTC<br>TTGCCTAAGTATTCCTTTCCTGATCACTATGCATTTTAAAG<br>TTAAACATTTTTAAGTATTTCAGATGCTTTAGAGAGATTTT<br>TTTTCCATGATCGCTTTCTACACTGTATTACATAAATAAAT<br>TAAATAAAATAACCCCGGGCAAGACTTTTCTTTGAAGGAT<br>GACTACAGACATTAAATAATCGAAGTAATTTTGGGTGGGG<br>AGAAGAGGCAGATTCAATTTTCTTTAACCAGTCTGAAGTT<br>TCATTTATGATACAAAAGAAGATGAAAATGGAAGTGGCAA<br>TATAAGGGGATGAGGAAGGCATGCCTGGACAAACCCTTC<br>TTTTAAGATGTGTCTTCAATTTGTATAAAATGGTGTTTTCA<br>TGTAAATAAATACATTCTTGGAGGAGCACCATTG |
| 6 | ENSP00000284981 | >TCONS_00180773\|ENST00000346798 (SEQ ID NO: 6)<br>CAGCAGCGCACTCGGTGCCCCGCGCAGGGTCGCGATGC<br>TGCCCGGTTTGGCACTGCTCCTGCTGGCCGCCTGGACG<br>GCTCGGGCGCTGGAGGTACCCACTGATGGTAATGCTGG<br>CCTGCTGGCTGAACCCCAGATTGCCATGTTCTGTGGCAG<br>ACTGAACATGCACATGAATGTCCAGAATGGGAAGTGGGA<br>TTCAGATCCATCAGGGACCAAAACCTGCATTGATACCAAG<br>GAAGGCATCCTGCAGTATTGCCAAGAAGTCTACCCTGAA<br>CTGCAGATCACCAATGTGGTAGAAGCCAACCAACCAGTG<br>ACCATCCAGAACTGGTGCAAGCGGGGCCGCAAGCAGTG<br>CAAGACCCATCCCCACTTTGTGATTCCCTACCGCTGCTTA<br>GTTGGTGAGTTTGTAAGTGATGCCCTTCTCGTTCCTGACA<br>AGTGCAAATTCTTACACCAGGAGAGGATGGATGTTTGCG |

TABLE 3-continued

APP_transcrips_final

| Number of variants | Ensembl_protein_id/ UniProt_id | Fasta_Formatted_DNA_sequences_with_cufflinks_ transcript_ids_and_corres-ponding_Ensembl_ids |
|---|---|---|
| | | AAACTCATCTTCACTGGCACACCGTCGCCAAAGAGACAT<br>GCAGTGAGAAGAGTACCAACTTGCATGACTACGGCATGT<br>TGCTGCCCTGCGGAATTGACAAGTTCCGAGGGGTAGAGT<br>TTGTGTGTTGCCCACTGGCTGAAGAAAGTGACAATGTGG<br>ATTCTGCTGATGCGGAGGAGGATGACTCGGATGTCTGGT<br>GGGGCGGAGCAGACACAGACTATGCAGATGGGAGTGAA<br>GACAAAGTAGTAGAAGTAGCAGAGGAGGAAGAAGTGGCT<br>GAGGTGGAAGAAGAAGAAGCCGATGATGACGAGGACGA<br>TGAGGATGGTGATGAGGTAGAGGAAGAGGCTGAGGAAC<br>CCTACGAAGAAGCCACAGAGAGAACCACCAGCATTGCCA<br>CCACCACCACCACCACCACAGAGTCTGTGGAAGAGGTGG<br>TTCGAGAGGTGTGCTCTGAACAAGCCGAGACGGGGCCG<br>TGCCGAGCAATGATCTCCCGCTGGTACTTTGATGTGACT<br>GAAGGGAAGTGTGCCCCATTCTTTTACGGCGGATGTGGC<br>GGCAACCGGAACAACTTTGACACAGAAGAGTACTGCATG<br>GCCGTGTGTGGCAGCGCCATGTCCCAAAGTTTACTCAAG<br>ACTACCCAGGAACCTCTTGCCCGAGATCCTGTTAAACTTC<br>CTACAACAGCAGCCAGTACCCCTGATGCCGTTGACAAGT<br>ATCTCGAGACACCTGGGGATGAGAATGAACATGCCCATT<br>TCCAGAAAGCCAAAGAGAGGCTTGAGGCCAAGCACCGA<br>GAGAGAATGTCCCAGGTCATGAGAGAATGGGAAGAGGCA<br>GAACGTCAAGCAAAGAACTTGCCTAAAGCTGATAAGAAG<br>GCAGTTATCCAGCATTTCCAGGAGAAAGTGGAATCTTTGG<br>AACAGGAAGCAGCCAACGAGAGACAGCAGCTGGTGGAG<br>ACACACATGGCCAGAGTGGAAGCCATGCTCAATGACCGC<br>CGCCGCCTGGCCCTGGAGAACTACATCACCGCTCTGCAG<br>GCTGTTCCTCCTCGGCCTCGTCACGTGTTCAATATGCTAA<br>AGAAGTATGTCCGCGCAGAACAGAAGGACAGACAGCACA<br>CCCTAAAGCATTTCGAGCATGTGCGCATGGTGGATCCCA<br>AGAAAGCCGCTCAGATCCGGTCCCAGGTTATGACACACC<br>TCCGTGTGATTTATGAGCGCATGAATCAGTCTCTCTCCCT<br>GCTCTACAACGTGCCTGCAGTGGCCGAGGAGATTCAGGA<br>TGAAGTTGATGAGCTGCTTCAGAAAGAGCAAAACTATTCA<br>GATGACGTCTTGGCCAACATGATTAGTGAACCAAGGATC<br>AGTTACGGAAACGATGCTCTCATGCCATCTTTGACCGAAA<br>CGAAAACCACCGTGGAGCTCCTTCCCGTGAATGGAGAGT<br>TCAGCCTGGACGATCTCCAGCCGTGGCATTCTTTTGGGG<br>CTGACTCTGTGCCAGCCAACACAGAAAACGAAGTTGAGC<br>CTGTTGATGCCCGCCCTGCTGCCGACCGAGGACTGACCA<br>CTCGACCAGGTTCTGGGTTGACAAATATCAAGACGGAGG<br>AGATCTCTGAAGTGAAGATGGATGCAGAATTCCGACATG<br>ACTCAGGATATGAAGTTCATCATCAAAAATTGGTGTTCTTT<br>GCAGAAGATGTGGGTTCAAACAAAGGTGCAATCATTGGA<br>CTCATGGTGGGCGGTGTTGTCATAGCGACAGTGATCGTC<br>ATCACCTTGGTGATGCTGAAGAAGAAACAGTACACATCCA<br>TTCATCATGGTGTGGTGGAGGTTGACGCCGCTGTCACCC<br>CAGAGGAGCGCCACCTGTCCAAGATGCAGCAGAACGGC<br>TACGAAAATCCAACCTACAAGTTCTTTGAGCAGATGCAGA<br>ACTAGACCCCCGCCACAGCAGCCTCTGAAGTTGGACAGC<br>AAAACCATTGCTTCACTACCCATCGGTGTCCATTTATAGA<br>ATAATGTGGGAAGAAACAAACCCGTTTTATGATTTACTCA<br>TTATCGCCTTTTGACAGCTGTGCTGTAACACAAGTAGATG<br>CCTGAACTTGAATTAATCCACACATCAGTAATGTATTCTAT<br>CTCTCTTTACATTTTGGTCTCTATACTACATTATTAATGGG<br>TTTTGTGTACTGTAAAGAATTTAGCTGTATCAAACTAGTGC<br>ATGAATAGATTCTCTCCTGATTATTTATCACATAGCCCCTT<br>AGCCAGTTGTATATTATTCTTGTGGTTTGTGACCCAATTAA<br>GTCCTACTTTACATATGCTTTAAGAATCGATGGGGGATGC<br>TTCATGTGAACGTGGGAGTTCAGCTGCTTCTCTTGCCTAA<br>GTATTCCTTTCCTGATCACTATGCATTTTAAAGTTAAACAT<br>TTTTAAGTATTTCAGATGCTTTAGAGAGATTTTTTTTCCAT<br>GACTGCATTTTACTGTACAGATTGCTGCTTCTGCTATATTT<br>GTGATATAGGAATTAAGAGGATACACACGTTTGTTTCTTC<br>GTGCCTGTTTTATGTGCACACATTAGGCATTGAGACTTCA<br>AGCTTTTCTTTTTTTGTCCACGTATCTTTGGGTCTTTGATA<br>AAGAAAAGAATCCCTGTTCATTGTAAGCACTTTTACGGGG<br>CGGGTGGGGAGGGGTGCTCTGCTGGTCTTCAATTACCAA<br>GAATTCTCCAAAACAATTTTCTGCAGGATGATTGTACAGA<br>ATCATTGCTTATGACATGATCGCTTTCTACACTGTATTACA<br>TAAATAAATTAAATAAAATAACCCCGGGCAAGACTTTTCTT<br>TGAAGGATGACTACAGACATTAAATAATCGAAGTAATTTT<br>GGGTGGGGAGAAGAGGCAGATTCAATTTTCTTTAACCAG<br>TCTGAAGTTTCATTTATGATACAAAAGAAGATGAAAATGG<br>AAGTGGCAATATAAGGGGATGAGGAAGGCATGCCTGGAC |

TABLE 3-continued

| APP_transcrips_final | | |
|---|---|---|
| Number of variants | Ensembl_protein_id/ UniProt_id | Fasta_Formatted_DNA_sequences_with_cufflinks_ transcript_ids_and_corres-ponding_Ensembl_ids |
| | | AAACCCTTCTTTTAAGATGTGTCTTCAATTTGTATAAAATG<br>GTGTTTTCATGTAAATAAATACATTCTTGGAGGAGCA |
| 7 | ENSP00000345463 | >TCONS_00180775\|ENST00000348990 (SEQ ID NO: 7)<br>AGTTTCCTCGGCAGCGGTAGGCGAGAGCACGCGGAGGA<br>GCGTGCGCGGGGGCCCCGGGAGACGGCGGCGGTGGCG<br>GCGCGGGCAGAGCAAGGACGCGGCGGATCCCACTCGCA<br>CAGCAGCGCACTCGGTGCCCCGCGCAGGGTCGCGATGC<br>TGCCCGGTTTGGCACTGCTCCTGCTGGCCGCCTGGACG<br>GCTCGGGCGCTGGAGGTACCCACTGATGGTAATGCTGG<br>CCTGCTGGCTGAACCCCAGATTGCCATGTTCTGTGGCAG<br>ACTGAACATGCACATGAATGTCCAGAATGGGAAGTGGGA<br>TTCAGATCCATCAGGGACCAAAACCTGCATTGATACCAAG<br>GAAGGCATCCTGCAGTATTGCCAAGAAGTCTACCCTGAA<br>CTGCAGATCACCAATGTGGTAGAAGCCAACCAACCAGTG<br>ACCATCCAGAACTGGTGCAAGCGGGGCCGCAAGCAGTG<br>CAAGACCCATCCCCACTTTGTGATTCCCTACCGCTGCTTA<br>GTTGGTGAGTTTGTAAGTGATGCCCTTCTCGTTCCTGACA<br>AGTGCAAATTCTTACACCAGGAGAGGATGGATGTTTGCG<br>AAACTCATCTTCACTGGCACACCGTCGCCAAAGAGACAT<br>GCAGTGAGAAGAGTACCAACTTGCATGACTACGGCATGT<br>TGCTGCCCTGCGGAATTGACAAGTTCCGAGGGGTAGAGT<br>TTGTGTGTTGCCCACTGGCTGAAGAAAGTGACAATGTGG<br>ATTCTGCTGATGCGGAGGAGGATGACTCGGATGTCTGGT<br>GGGGCGGAGCAGACACAGACTATGCAGATGGGAGTGAA<br>GACAAAGTAGTAGAAGTAGCAGAGGAGGAAGAAGTGGCT<br>GAGGTGGAAGAAGAAGAAGCCGATGATGACGAGGACGA<br>TGAGGATGGTGATGAGGTAGAGGAAGAGGCTGAGGAAC<br>CCTACGAAGAAGCCACAGAGAGAACCACCAGCATTGCCA<br>CCACCACCACCACCACCACAGAGTCTGTGGAAGAGGTGG<br>TTCGAGTTCCTACAACAGCAGCCAGTACCCCTGATGCCG<br>TTGACAAGTATCTCGAGACACCTGGGGATGAGAATGAAC<br>ATGCCCATTTCCAGAAAGCCAAAGAGAGGCTTGAGGCCA<br>AGCACCGAGAGAGAATGTCCCAGGTCATGAGAGAATGGG<br>AAGAGGCAGAACGTCAAGCAAAGAACTTGCCTAAAGCTG<br>ATAAGAAGGCAGTTATCCAGCATTTCCAGGAGAAAGTGG<br>AATCTTTGGAACAGGAAGCAGCCAACGAGAGACAGCAGC<br>TGGTGGAGACACACATGGCCAGAGTGGAAGCCATGCTCA<br>ATGACCGCCGCCGCCTGGCCCTGGAGAACTACATCACC<br>GCTCTGCAGGCTGTTCCTCCTCGGCCTCGTCACGTGTTC<br>AATATGCTAAAGAAGTATGTCCGCGCAGAACAGAAGGAC<br>AGACAGCACACCCTAAAGCATTTCGAGCATGTGCGCATG<br>GTGGATCCCAAGAAAGCCGCTCAGATCCGGTCCCAGGTT<br>ATGACACACCTCCGTGTGATTTATGAGCGCATGAATCAGT<br>CTCTCTCCCTGCTCTACAACGTGCCTGCAGTGGCCGAGG<br>AGATTCAGGATGAAGTTGATGAGCTGCTTCAGAAAGAGC<br>AAAACTATTCAGATGACGTCTTGGCCAACATGATTAGTGA<br>ACCAAGGATCAGTTACGGAAACGATGCTCTCATGCCATCT<br>TTGACCGAAACGAAAACCACCGTGGAGCTCCTTCCCGTG<br>AATGGAGAGTTCAGCCTGGACGATCTCCAGCCGTGGCAT<br>TCTTTTGGGGCTGACTCTGTGCCAGCCAACACAGAAAAC<br>GAAGTTGAGCCTGTTGATGCCCGCCCTGCTGCCGACCGA<br>GGACTGACCACTCGACCAGGTTCTGGGTTGACAAATATC<br>AAGACGGAGGAGATCTCTGAAGTGAAGATGGATGCAGAA<br>TTCCGACATGACTCAGGATATGAAGTTCATCATCAAAAAT<br>TGGTGTTCTTTGCAGAAGATGTGGGTTCAAACAAAGGTG<br>CAATCATTGGACTCATGGTGGGCGGTGTTGTCATAGCGA<br>CAGTGATCGTCATCACCTTGGTGATGCTGAAGAAGAAAC<br>AGTACACATCCATTCATCATGGTGTGGTGGAGGTTGACG<br>CCGCTGTCACCCCAGAGGAGCGCCACCTGTCCAAGATG<br>CAGCAGAACGGCTACGAAAATCCAACCTACAAGTTCTTTG<br>AGCAGATGCAGAACTAGACCCCCGCCACAGCAGCCTCTG<br>AAGTTGGACAGCAAAACCATTGCTTCACTACCCATCGGTG<br>TCCATTTATAGAATAATGTGGGAAGAAACAAACCCGTTTT<br>ATGATTTACTCATTATCGCCTTTTGACAGCTGTGCTGTAA<br>CACAAGTAGATGCCTGAACTTGAATTAATCCACACATCAG<br>TAATGTATTCTATCTCTCTTTACATTTTGGTCTCTATACTAC<br>ATTATTAATGGGTTTTGTGTACTGTAAAGAATTTAGCTGTA<br>TCAAACTAGTGCATGAATAGATTCTCTCCTGATTATTTATC<br>ACATAGCCCCTTAGCCAGTTGTATATTATTCTTGTGGTTT<br>GTGACCCAATTAAGTCCTACTTTACATATGCTTTAAGAATC<br>GATGGGGGATGCTTCATGTGAACGTGGGAGTTCAGCTGC<br>TTCTCTTGCCTAAGTATTCCTTTCCTGATCACTATGCATTT<br>TAAAGTTAAACATTTTTAAGTATTTCAGATGCTTTAGAGAG<br>ATTTTTTTTCCATGACTGCATTTTACTGTACAGATTGCTGC |

TABLE 3-continued

| APP_transcrips_final | | |
|---|---|---|
| Number of variants | Ensembl_protein_id/ UniProt_id | Fasta_Formatted_DNA_sequences_with_cufflinks_ transcript_ids_and_corres-ponding_Ensembl_ids |
| | | TTCTGCTATATTTGTGATATAGGAATTAAGAGGATACACA<br>CGTTTGTTTCTTCGTGCCTGTTTTATGTGCACACATTAGG<br>CATTGAGACTTCAAGCTTTTCTTTTTTTGTCCACGTATCTT<br>TGGGTCTTTGATAAAGAAAAGAATCCCTGTTCATTGTAAG<br>CACTTTTACGGGGGGGTGGGGAGGGGTGCTCTGCTGG<br>TCTTCAATTACCAAGAATTCTCCAAAACAATTTTCTGCAGG<br>ATGATTGTACAGAATCATTGCTTATGACATGATCGCTTTCT<br>ACACTGTATTACATAAATAAATTAAATAAAATAACCCCGGG<br>CAAGACTTTTCTTTGAAGGATGACTACAGACATTAAATAAT<br>CGAAGTAATTTTGGGTGGGGAGAAGAGGCAGATTCAATT<br>TTCTTTAACCAGTCTGAAGTTTCATTTATGATACAAAAGAA<br>GATGAAAATGGAAGTGGCAATATAAGGGGATGAGGAAGG<br>CATGCCTGGACAAACCCTTCTTTTAAGATGTGTCTTCAAT<br>TTGTATAAAATGGTGTTTTCATGTAAATAAATACATTCTTG<br>GAGGAGCA |
| 8 | ENSP00000346129 | >TCONS_00180774\|ENST00000354192 (SEQ ID NO: 8)<br>GCGAGAGCACGCGGAGGAGCGTGCGCGGGGGCCCCGG<br>GAGACGGCGGCGGTGGCGGCGCGGGCAGAGCAAGGAC<br>GCGGCGGATCCCACTCGCACAGCAGCGCACTCGGTGCC<br>CCGCGCAGGGTCGCGATGCTGCCCGGTTTGGCACTGCT<br>CCTGCTGGCCGCCTGGACGGCTCGGGCGCTGGAGGTCT<br>ACCCTGAACTGCAGATCACCAATGTGGTAGAAGCCAACC<br>AACCAGTGACCATCCAGAACTGGTGCAAGCGGGGCCGC<br>AAGCAGTGCAAGACCCATCCCCACTTTGTGATTCCCTACC<br>GCTGCTTAGTTGGTGAGTTTGTAAGTGATGCCCTTCTCGT<br>TCCTGACAAGTGCAAATTCTTACACCAGGAGAGGATGGA<br>TGTTTGCGAAACTCATCTTCACTGGCACACCGTCGCCAAA<br>GAGACATGCAGTGAGAAGAGTACCAACTTGCATGACTAC<br>GGCATGTTGCTGCCCTGCGGAATTGACAAGTTCCGAGGG<br>GTAGAGTTTGTGTGTTGCCCACTGGCTGAAGAAAGTGAC<br>AATGTGGATTCTGCTGATGCGGAGGAGGATGACTCGGAT<br>GTCTGGTGGGGCGGAGCAGACACAGACTATGCAGATGG<br>GAGTGAAGACAAAGTAGTAGAAGTAGCAGAGGAGGAAGA<br>AGTGGCTGAGGTGGAAGAAGAAGAAGCCGATGATGACG<br>AGGACGATGAGGATGGTGATGAGGTAGAGGAAGAGGCT<br>GAGGAACCCTACGAAGAAGCCACAGAGAGAACCACCAG<br>CATTGCCACCACCACCACCACCACCACAGAGTCTGTGGA<br>AGAGGTGGTTCGAGTTCCTACAACAGCAGCCAGTACCCC<br>TGATGCCGTTGACAAGTATCTCGAGACACCTGGGGATGA<br>GAATGAACATGCCCATTTCCAGAAAGCCAAAGAGAGGCT<br>TGAGGCCAAGCACCGAGAGAGAATGTCCCAGGTCATGAG<br>AGAATGGGAAGAGGCAGAACGTCAAGCAAAGAACTTGCC<br>TAAAGCTGATAAGAAGGCAGTTATCCAGCATTTCCAGGAG<br>AAAGTGGAATCTTTGGAACAGGAAGCAGCCAACGAGAGA<br>CAGCAGCTGGTGGAGACACACATGGCCAGAGTGGAAGC<br>CATGCTCAATGACCGCCGCCGCCTGGCCCTGGAGAACTA<br>CATCACCGCTCTGCAGGCTGTTCCTCCTCGGCCTCGTCA<br>CGTGTTCAATATGCTAAAGAAGTATGTCCGCGCAGAACA<br>GAAGGACAGACAGCACACCCTAAAGCATTTCGAGCATGT<br>GCGCATGGTGGATCCCAAGAAAGCCGCTCAGATCCGGTC<br>CCAGGTTATGACACACCTCCGTGTGATTTATGAGCGCAT<br>GAATCAGTCTCTCTCCCTGCTCTACAACGTGCCTGCAGT<br>GGCCGAGGAGATTCAGGATGAAGTTGATGAGCTGCTTCA<br>GAAAGAGCAAAACTATTCAGATGACGTCTTGGCCAACATG<br>ATTAGTGAACCAAGGATCAGTTACGGAAACGATGCTCTCA<br>TGCCATCTTTGACCGAAACGAAAACCACCGTGGAGCTCC<br>TTCCCGTGAATGGAGAGTTCAGCCTGGACGATCTCCAGC<br>CGTGGCATTCTTTTGGGGCTGACTCTGTGCCAGCCAACA<br>CAGAAAACGAAGTTGAGCCTGTTGATGCCCGCCCTGCTG<br>CCGACCGAGGACTGACCACTCGACCAGGTTCTGGGTTGA<br>CAAATATCAAGACGGAGGAGATCTCTGAAGTGAAGATGG<br>ATGCAGAATTCCGACATGACTCAGGATATGAAGTTCATCA<br>TCAAAAATTGGTGTTCTTTGCAGAAGATGTGGGTTCAAAC<br>AAAGGTGCAATCATTGGACTCATGGTGGGCGGTGTTGTC<br>ATAGCGACAGTGATCGTCATCACCTTGGTGATGCTGAAG<br>AAGAAACAGTACACATCCATTCATCATGGTGTGGTGGAG<br>GTTGACGCCGCTGTCACCCCAGAGGAGCGCCACCTGTC<br>CAAGATGCAGCAGAACGGCTACGAAAATCCAACCTACAA<br>GTTCTTTGAGCAGATGCAGAACTAGACCCCCGCCACAGC<br>AGCCTCTGAAGTTGGACAGCAAAACCATTGCTTCACTACC<br>CATCGGTGTCCATTTATAGAATAATGTGGGAAGAAACAAA<br>CCCGTTTTATGATTTACTCATTATCGCCTTTTGACAGCTGT<br>GCTGTAACACAAGTAGATGCCTGAACTTGAATTAATCCAC<br>ACATCAGTAATGTATTCTATCTCTCTTTACATTTTGGTCTC |

TABLE 3-continued

| APP_transcrips_final | | |
|---|---|---|
| Number of variants | Ensembl_protein_id/ UniProt_id | Fasta_Formatted_DNA_sequences_with_cufflinks_ transcript_ids_and_corres-ponding_Ensembl_ids |
| | | TATACTACATTATTAATGGGTTTTGTGTACTGTAAAGAATT TAGCTGTATCAAACTAGTGCATGAATAGATTCTCTCCTGA TTATTTATCACATAGCCCCTTAGCCAGTTGTATATTATTCT TGTGGTTTGTGACCCAATTAAGTCCTACTTTACATATGCTT TAAGAATCGATGGGGGATGCTTCATGTGAACGTGGGAGT TCAGCTGCTTCTCTTGCCTAAGTATTCCTTTCCTGATCACT ATGCATTTTAAAGTTAAACATTTTTAAGTATTTCAGATGCT TTAGAGAGATTTTTTTTCCATGACTGCATTTTACTGTACAG ATTGCTGCTTCTGCTATATTTGTGATATAGGAATTAAGAG GATACACACGTTTGTTTCTTCGTGCCTGTTTTATGTGCAC ACATTAGGCATTGAGACTTCAAGCTTTTCTTTTTTTGTCCA CGTATCTTTGGGTCTTTGATAAAGAAAAGAATCCCTGTTC ATTGTAAGCACTTTTACGGGGGGGGTGGGGAGGGGTGC TCTGCTGGTCTTCAATTACCAAGAATTCTCCAAAACAATTT TCTGCAGGATGATTGTACAGAATCATTGCTTATGACATGA TCGCTTTCTACACTGTATTACATAAATAAATTAAATAAAAT AACCCCGGGCAAGACTTTTCTTTGAAGGATGACTACAGA CATTAAATAATCGAAGTAATTTTGGGTGGGGAGAAGAGG CAGATTCAATTTTCTTTAACCAGTCTGAAGTTTCATTTATG ATACAAAAGAAGATGAAAATGGAAGTGGCAATATAAGGG GATGAGGAAGGCATGCCTGGACAAACCCCTTCTTTTAAGAT GTGTCTTCAATTTGTATAAAATGGTGTTTTCATGTAAATAA ATACATTCTTGGAGGAGCA |
| 9 | ENSP00000350578 | >TCONS_00180776\|ENST00000357903 SEQ ID NO: 9) CGCCGCGCTCGGGCTCCGTCAGTTTCCTCGGCAGCGGT AGGCGAGAGCACGCGGAGGAGCGTGCGCGGGGGCCCC GGGAGACGGCGGCGGTGGCGGCGCGGGCAGAGCAAGG ACGCGGCGGATCCCACTCGCACAGCAGCGCACTCGGTG CCCCGCGCAGGGTCGCGATGCTGCCCGGTTTGGCACTG CTCCTGCTGGCCGCCTGGACGGCTCGGGCGCTGGAGGT ACCCACTGATGGTAATGCTGGCCTGCTGGCTGAACCCCA GATTGCCATGTTCTGTGGCAGACTGAACATGCACATGAAT GTCCAGAATGGGAAGTGGGATTCAGATCCATCAGGGACC AAAACCTGCATTGATACCAAGGAAGGCATCCTGCAGTATT GCCAAGAAGTCTACCCTGAACTGCAGATCACCAATGTGG TAGAAGCCAACCAACCAGTGACCATCCAGAACTGGTGCA AGCGGGGCCGCAAGCAGTGCAAGACCCATCCCCACTTT GTGATTCCCTACCGCTGCTTAGTTGGTGAGTTTGTAAGTG ATGCCCTTCTCGTTCCTGACAAGTGCAAATTCTTACACCA GGAGAGGATGGATGTTTGCGAAACTCATCTTCACTGGCA CACCGTCGCCAAAGAGACATGCAGTGAGAAGAGTACCAA CTTGCATGACTACGGCATGTTGCTGCCCTGCGGAATTGA CAAGTTCCGAGGGGTAGAGTTTGTGTGTTGCCCACTGGC TGAAGAAAGTGACAATGTGGATTCTGCTGATGCGGAGGA GGATGACTCGGATGTCTGGTGGGGCGGAGCAGACACAG ACTATGCAGATGGGAGTGAAGACAAAGTAGTAGAAGTAG CAGAGGAGGAAGAAGTGGCTGAGGTGGAAGAAGAAGAA GCCGATGATGACGAGGACGATGAGGATGGTGATGAGGT AGAGGAAGAGGCTGAGGAACCCTACGAAGAAGCCACAG AGAGAACCACCAGCATTGCCACCACCACCACCACCACCA CAGAGTCTGTGGAAGAGGTGGTTCGAGAGGTGTGCTCTG AACAAGCCGAGACGGGGCCGTGCCGAGCAATGATCTCC CGCTGGTACTTTGATGTGACTGAAGGGAAGTGTGCCCCA TTCTTTTACGGCGGATGTGGCGGCAACCGGAACAACTTT GACACAGAAGAGTACTGCATGGCCGTGTGTGGCAGCGC CATTCCTACAACAGCAGCCAGTACCCCTGATGCCGTTGA CAAGTATCTCGAGACACCTGGGGATGAGAATGAACATGC CCATTTCCAGAAAGCCAAAGAGAGGCTTGAGGCCAAGCA CCGAGAGAGAATGTCCCAGGTCATGAGAGAATGGGAAGA GGCAGAACGTCAAGCAAAGAACTTGCCTAAAGCTGATAA GAAGGCAGTTATCCAGCATTTCCAGGAGAAAGTGGAATC TTTGGAACAGGAAGCAGCCAACGAGAGACAGCAGCTGGT GGAGACACACATGGCCAGAGTGGAAGCCATGCTCAATGA CCGCCGCCGCCTGGCCCTGGAGAACTACATCACCGCTCT GCAGGCTGTTCCTCCTCGGCCTCGTCACGTGTTCAATAT GCTAAAGAAGTATGTCCGCGCAGAACAGAAGGACAGACA GCACACCCTAAAGCATTTCGAGCATGTGCGCATGGTGGA TCCCAAGAAAGCCGCTCAGATCCGGTCCCAGGTTATGAC ACACCTCCGTGTGATTTATGAGCGCATGAATCAGTCTCTC TCCCTGCTCTACAACGTGCCTGCAGTGGCCGAGGAGATT CAGGATGAAGTTGATGAGCTGCTTCAGAAAGAGCAAAAC TATTCAGATGACGTCTTGGCCAACATGATTAGTGAACCAA GGATCAGTTACGGAAACGATGCTCTCATGCCATCTTTGAC CGAAACGAAAACCACCGTGGAGCTCCTTCCCGTGAATGG |

TABLE 3-continued

<table>
<tr><th colspan="3">APP_transcrips_final</th></tr>
<tr><th>Number of variants</th><th>Ensembl_protein_id/ UniProt_id</th><th>Fasta_Formatted_DNA_sequences_with_cufflinks_ transcript_ids_and_corres-ponding_Ensembl_ids</th></tr>
<tr><td></td><td></td><td>AGAGTTCAGCCTGGACGATCTCCAGCCGTGGCATTCTTT<br>TGGGGCTGACTCTGTGCCAGCCAACACAGAAAACGAAGT<br>TGAGCCTGTTGATGCCCGCCCTGCTGCCGACCGAGGACT<br>GACCACTCGACCAGGTTCTGGGTTGACAAATATCAAGAC<br>GGAGGAGATCTCTGAAGTGAAGATGGATGCAGAATTCCG<br>ACATGACTCAGGATATGAAGTTCATCATCAAAAATTGGTG<br>TTCTTTGCAGAAGATGTGGGTTCAAACAAAGGTGCAATCA<br>TTGGACTCATGGTGGGCGGTGTTGTCATAGCGACAGTGA<br>TCGTCATCACCTTGGTGATGCTGAAGAAGAAACAGTACAC<br>ATCCATTCATCATGGTGTGGTGGAGGTTGACGCCGCTGT<br>CACCCCAGAGGAGCGCCACCTGTCCAAGATGCAGCAGA<br>ACGGCTACGAAAATCCAACCTACAAGTTCTTTGAGCAGAT<br>GCAGAACTAGACCCCCGCCACAGCAGCCTCTGAAGTTGG<br>ACAGCAAAACCATTGCTTCACTACCCATCGGTGTCCATTT<br>ATAGAATAATGTGGGAAGAAACAAACCCGTTTTATGATTT<br>ACTCATTATCGCCTTTTGACAGCTGTGCTGTAACACAAGT<br>AGATGCCTGAACTTGAATTAATCCACACATCAGTAATGTA<br>TTCTATCTCTCTTTACATTTTGGTCTCTATACTACATTATTA<br>ATGGGTTTTGTGTACTGTAAAGAATTTAGCTGTATCAAACT<br>AGTGCATGAATAGATTCTCTCCTGATTATTTATCACATAGC<br>CCCTTAGCCAGTTGTATATTATTCTTGTGGTTTGTGACCC<br>AATTAAGTCCTACTTTACATATGCTTTAAGAATCGATGGG<br>GGATGCTTCATGTGAACGTGGGAGTTCAGCTGCTTCTCTT<br>GCCTAAGTATTCCTTTCCTGATCACTATGCATTTTAAAGTT<br>AAACATTTTTAAGTATTTCAGATGCTTTAGAGAGATTTTTT<br>TTCCATGACTGCATTTTACTGTACAGATTGCTGCTTCTGCT<br>ATATTTGTGATATAGGAATTAAGAGGATACACACGTTTGTT<br>TCTTCGTGCCTGTTTTATGTGCACACATTAGGCATTGAGA<br>CTTCAAGCTTTTCTTTTTTTGTCCACGTATCTTTGGGTCTT<br>TGATAAAGAAAAGAATCCCTGTTCATTGTAAGCACTTTTAC<br>GGGGCGGGTGGGGAGGGGTGCTCTGCTGGTCTTCAATT<br>ACCAAGAATTCTCCAAAACAATTTTCTGCAGGATGATTGT<br>ACAGAATCATTGCTTATGACATGATCGCTTTCTACACTGT<br>ATTACATAAATAAATTAAATAAAATAACCCCGGGCAAGACT<br>TTTCTTTGAAGGATGACTACAGACATTAAATAATCGAAGTA<br>ATTTTGGGTGGGGAGAAGAGGCAGATTCAATTTTCTTTAA<br>CCAGTCTGAAGTTTCATTTATGATACAAAAGAAGATGAAA<br>ATGGAAGTGGCAATATAAGGGGATGAGGAAGGCATGCCT<br>GGACAAACCCTTCTTTTAAGATGTGTCTTCAATTTGTATAA<br>AATGGTGTTTTCATGTAAATAAATACATTCTTGGAGGAGC<br>A</td></tr>
<tr><td>10</td><td>ENSP00000350578</td><td>>TCONS_00179143|ENST00000357903<br>(SEQ ID NO: 10)<br>CTTTATCACTTTACTATGCAATTTTTATGACTATGCTTAAG<br>GAGAGTAAATTTTTCGAAGTTATTGAGGCAATGGAGAGTC<br>TTTGGAATGAGGATAATTAGGCCTGAGGACACAGAGGAA<br>TCATGAGGAAGAATTCTCCAGTTTCATTCCTTTTTCTGGG<br>TACAGTTTGTTTCTCCTTCTAAGTAAGTTCCTAGATATAGA<br>ATGAATTGGAAAAAATGAAACGTGAGGTTTGCTACGTCTA<br>TAACAGTATCACATTTCATTTTTTAAAACTGCCAATGCTTT<br>CAGTGAGGACCAGAAAGTACAGTGAGAAAAAAAAATTCCT<br>CAAATATTAGTTTTCATGCTCTTGCACGCATTTTTATAAAG<br>GCAAAAGTCATTCTGGTGCCTGTATACAATCTAAAGGCAT<br>AATCTCCTGGAGCCTTCAGTGCTGGTTTTGGGGTTTTCTG<br>GAGATCAATCCACAGTGTCCCATTTTTTCTGCTGGAGCTC<br>TGAACCCACTAAGAGAGAGCAAGAAGAGATGTAAACCTC<br>TCCTTTGCTTCTGATAAAGCCAAGCCCTTACTAGTCCACA<br>TGATGCTTTCTCTGGGGAGTGAGTCACATACAGGAGACA<br>TGGCTTGTCCAGCTGCGTGCTGGACTGAATTTCAGCTCC<br>AACCTGAACCTTCCAACAGGACAAGGGAGGGAGGAGAAT<br>GGGCCGTAGCA</td></tr>
<tr><td>11</td><td>ENSP00000350578</td><td>>TCONS_00179153|ENST00000357903<br>(SEQ ID NO: 11)<br>GTGTGTACCCCTAAACCCAGCTTATTATTTTTTTGACTTTT<br>TGTAGAAACAGGGTCTCCCCATGTTGCCCAGGCTGGTCT<br>TAAACTCCTGGGCTCAAATGATCCTCCTGCCTCAGCCTCC<br>CATAGGGCTAGGATTACAGGTGTGAGCCACCATGCCTGG<br>CCTTTTATACTGTTTATTCCCTTTAGATACAGTTAATGGAC<br>ATTAATAAGCAGTTTATGCCAATCCCTTTTCATAGCTAATA<br>AGAAGTCTTATCTTGGATAAATAAAACCTAGCCACTAATG<br>CTGCCACACCCAAATAAACTCTCTATGCATCTGAACTTCT<br>TGAGGTTAATAATGCTTCATTGTAATATTTTATAAAATCAC<br>CACTTTGGAAGTGAACACCACTAGAAATTCACATGGCCAG</td></tr>
</table>

TABLE 3-continued

| APP_transcrips_final | | |
|---|---|---|
| Number of variants | Ensembl_protein_id/ UniProt_id | Fasta_Formatted_DNA_sequences_with_cufflinks_ transcript_ids_and_corres-ponding_Ensembl_ids |
| | | TTTATAGATGGGGACTGGGGGAAGCAGGGAGGATCTCTG<br>CAATCCAGTAGTTAGGCTCTGCCAGAATGTATTTAGAGTT<br>GTCTCTAAATACATTCTGAGTCTCTGCTTCATTTTTTTTTC<br>AATGAAAATGACAATGTCTGTCATCCCATGTTCAAGACAA<br>ATATAACAAGTTTCTAAGAATCCTTATATTTTTGTTATTGCA<br>TATAAGCATGAGTTTTAAAAACCTCTGAATGTTTAAAGGAT<br>CACCTGGGGGAATAAGAAAAATGCAGATCTCTGTAGGTC<br>TGAGGTAGAGCCCAAGAATCTGTATTTTTAACTAGAATTC<br>CTCTAAATTACTGTGCTTCACTTGGCCCCAATTACACATTA<br>GGAGACAATGATTTCAGGATGACAATCAGCCTTTTCCATC<br>CAAGGACTTAAAGCAGCTAAACCGAAGACACCGACAAAT<br>ACCAGATACTTTTCTCAGTCTACTGGCTGATGGCACAAAA<br>GTGCAGAAGTCACGTAGGGC |
| 12 | ENSP00000350578 | >TCONS_00179154\|ENST00000357903<br>(SEQ ID NO: 12)<br>CATGAGGAACTCCTTGGGCCTTGACCATTTTTAGCACTTT<br>CACAGTTTCTGATTTTGATCAAGCCACTTAATCACCCAGG<br>ATTCTGAATCTGAAAACCAGGAGGGTTTAATTCCACTTTC<br>ATGTTCCCTTGAGGAGCTGTTGGCAGCAGGATGAAGGCA<br>GGTCCATACAGAACATGGGAAGGAAGCCAGGAAGCCAG<br>CTTTTCCTTTCACATCAAAGAGATCTAGAAAGCAAAACCT<br>GTCTCACATTTGCATACAATATTAGACTTACATATGGATGC<br>CATGTCTGTCAAAAGACAGGCTAATTAGGGCATTAGTTTC<br>TTTAATGGTTGCGATTTAGTAATTCACAAATAGTCCCACTT<br>AATTTTTCATCCTATACCTAAAGGATCTACTTCACACTTGA<br>AGTTTAAGAAGGCTTCTCCCTTAAGATAGAAAGAAGGCAT<br>TCAAGTATCAAAATACTGGTTTCCTGCCAAAAAATAAGGG<br>ATGAGAAAAAGCAGACACTTAGCTTATCAATCAAAATGCT<br>GGCAGGGAAAGACTACTGGATTACCAAGTTCATTCCCCT<br>AGCCTGCACTGATTCCTCTTTTTCTCTAAAGTTTCTTATTT<br>TTTCAGTTTTTCTCATGATACTGACATTGCCAACCAGCAG<br>TCTGGAAACTGTTCAGGTTGATTCTTAGCAGAAAATCGAG<br>GGGCTCTCCTGTTACTGTTAATATCCTTAAAACACTTAAAT<br>TTGGTTAGTTTGCTTCAAGCATTCTCAGTATATTACAAAAA<br>AAAAAGTACTCAAGAATTTCTAGACTTTATTTTGACTGAC<br>ATCAGCTACCCTAATGAACAGGAGGGGACAACAGCAAGG<br>TATATTAGGAGCATCTCCTTCCTTTTTAATCAGAATTATAT<br>AGGAATTAAGAACTCTAAGGCCACAGTAGAGTATAGTATC<br>TTGGAAGAAGAAAGCGGAGAATGTCTGACATTTTCACTGA<br>TCGTTTAGGCTGATGGCTTAAACCATTTCCACCCAAGTTT<br>CTTACAAGTTAGCATTTCCAGCCAACATTACCTACTGCAA<br>TTTCTCTATAATCTTAAGGGTATTGAGCCCCCAAATGAGA<br>GAGAGAAAAGAGATGTAAACTAAACAGGAGTCAGAGAAG<br>GGGAAACTGAGTCTGTTGCACATCATTTACCCTTTAACAT<br>GATTTTAAAGGTAATAATGCTTATAAAAATATTAGTAGTAG<br>TAAGGGATATCAGGTGACAAGCAGAAGTGCCCCTCTCCA<br>CAGATATGCCAGTGTATCTGTAGAAATACGGTGCTAAAAT<br>TAGAAAAGACTGAACATTTTAATTTATTAGGTAGACCC |
| 13 | ENSP00000351796 | >TCONS_00180770\|ENST00000358918<br>(SEQ ID NO: 13)<br>CGCCGCGCTCGGGCTCCGTCAGTTTCCTCGGCAGCGGT<br>AGGCGAGAGCACGCGGAGGAGCGTGCGCGGGGGCCCC<br>GGGAGACGGCGGCGGTGGCGGCGCGGGCAGAGCAAGG<br>ACGCGGCGGATCCCACTCGCACAGCAGCGCACTCGGTG<br>CCCCGCGCAGGGTCGCGATGCTGCCCGGTTTGGCACTG<br>CTCCTGCTGGCCGCCTGGACGGCTCGGGCGCTGGAGGT<br>ACCCACTGATGGTAATGCTGGCCTGCTGGCTGAACCCCA<br>GATTGCCATGTTCTGTGGCAGACTGAACATGCACATGAAT<br>GTCCAGAATGGGAAGTGGGATTCAGATCCATCAGGGACC<br>AAAACCTGCATTGATACCAAGGAAGGCATCCTGCAGTATT<br>GCCAAGAAGTCTACCCTGAACTGCAGATCACCAATGTGG<br>TAGAAGCCAACCAACCAGTGACCATCCAGAACTGGTGCA<br>AGCGGGGCCGCAAGCAGTGCAAGACCCATCCCCACTTT<br>GTGATTCCCTACCGCTGCTTAGTTGGTGAGTTTGTAAGTG<br>ATGCCCTTCTCGTTCCTGACAAGTGCAAATTCTTACACCA<br>GGAGAGGATGGATGTTTGCGAAACTCATCTTCACTGGCA<br>CACCGTCGCCAAAGAGACATGCAGTGAGAAGAGTACCAA<br>CTTGCATGACTACGGCATGTTGCTGCCCTGCGGAATTGA<br>CAAGTTCCGAGGGGTAGAGTTTGTGTGTTGCCCACTGGC<br>TGAAGAAAGTGACAATGTGGATTCTGCTGATGCGGAGGA<br>GGATGACTCGGATGTCTGGTGGGGCGGAGCAGACACAG<br>ACTATGCAGATGGGAGTGAAGACAAAGTAGTAGAAGTAG<br>CAGAGGAGGAAGAAGTGGCTGAGGTGGAAGAAGAAGAA |

TABLE 3-continued

APP_transcrips_final

| Number of variants | Ensembl_protein_id/ UniProt_id | Fasta_Formatted_DNA_sequences_with_cufflinks_ transcript_ids_and_corres-ponding_Ensembl_ids |
|---|---|---|
| | | GCCGATGATGACGAGGACGATGAGGATGGTGATGAGGT |
| | | AGAGGAAGAGGCTGAGGAACCCTACGAAGAAGCCACAG |
| | | AGAGAACCACCAGCATTGCCACCACCACCACCACCACCA |
| | | CAGAGTCTGTGGAAGAGGTGGTTCGAGAGGTGTGCTCTG |
| | | AACAAGCCGAGACGGGGCCGTGCCGAGCAATGATCTCC |
| | | CGCTGGTACTTTGATGTGACTGAAGGGAAGTGTGCCCCA |
| | | TTCTTTTACGGCGGATGTGGCGGCAACCGGAACAACTTT |
| | | GACACAGAAGAGTACTGCATGGCCGTGTGTGGCAGCGC |
| | | CATGTCCCAAAGTTTACTCAAGACTACCCAGGAACCTCTT |
| | | GCCCGAGATCCTGTTAAACTTCCTACAACAGCAGCCAGT |
| | | ACCCCTGATGCCGTTGACAAGTATCTCGAGACACCTGGG |
| | | GATGAGAATGAACATGCCCATTTCCAGAAAGCCAAAGAG |
| | | AGGCTTGAGGCCAAGCACCGAGAGAGAATGTCCCAGGT |
| | | CATGAGAGAATGGGAAGAGGCAGAACGTCAAGCAAAGAA |
| | | CTTGCCTAAAGCTGATAAGAAGGCAGTTATCCAGCATTTC |
| | | CAGGAGAAAGTGGAATCTTTGGAACAGGAAGCAGCCAAC |
| | | GAGAGACAGCAGCTGGTGGAGACACACATGGCCAGAGT |
| | | GGAAGCCATGCTCAATGACCGCCGCCGCCTGGCCCTGG |
| | | AGAACTACATCACCGCTCTGCAGGCTGTTCCTCCTCGGC |
| | | CTCGTCACGTGTTCAATATGCTAAAGAAGTATGTCCGCGC |
| | | AGAACAGAAGGACAGACAGCACACCCTAAAGCATTTCGA |
| | | GCATGTGCGCATGGTGGATCCCAAGAAAGCCGCTCAGAT |
| | | CCGGTCCCAGGTTATGACACACCTCCGTGTGATTTATGA |
| | | GCGCATGAATCAGTCTCTCTCCCTGCTCTACAACGTGCCT |
| | | GCAGTGGCCGAGGAGATTCAGGATGAAGTTGATGAGCTG |
| | | CTTCAGAAAGAGCAAAACTATTCAGATGACGTCTTGGCCA |
| | | ACATGATTAGTGAACCAAGGATCAGTTACGGAAACGATG |
| | | CTCTCATGCCATCTTTGACCGAAACGAAAACCACCGTGG |
| | | AGCTCCTTCCCGTGAATGGAGAGTTCAGCCTGGACGATC |
| | | TCCAGCCGTGGCATTCTTTTGGGGCTGACTCTGTGCCAG |
| | | CCAACACAGAAAACGAAGGTTCTGGGTTGACAAATATCAA |
| | | GACGGAGGAGATCTCTGAAGTGAAGATGGATGCAGAATT |
| | | CCGACATGACTCAGGATATGAAGTTCATCATCAAAAATTG |
| | | GTGTTCTTTGCAGAAGATGTGGGTTCAAACAAAGGTGCAA |
| | | TCATTGGACTCATGGTGGGCGGTGTTGTCATAGCGACAG |
| | | TGATCGTCATCACCTTGGTGATGCTGAAGAAGAAACAGTA |
| | | CACATCCATTCATCATGGTGTGGTGGAGGTTGACGCCGC |
| | | TGTCACCCCAGAGGAGCGCCACCTGTCCAAGATGCAGCA |
| | | GAACGGCTACGAAAATCCAACCTACAAGTTCTTTGAGCAG |
| | | ATGCAGAACTAGACCCCCGCCACAGCAGCCTCTGAAGTT |
| | | GGACAGCAAAACCATTGCTTCACTACCCATCGGTGTCCAT |
| | | TTATAGAATAATGTGGGAAGAAACAAACCCGTTTTATGAT |
| | | TTACTCATTATCGCCTTTTGACAGCTGTGCTGTAACACAA |
| | | GTAGATGCCTGAACTTGAATTAATCCACACATCAGTAATG |
| | | TATTCTATCTCTCTTTACATTTTGGTCTCTATACTACATTAT |
| | | TAATGGGTTTTGTGTACTGTAAAGAATTTAGCTGTATCAAA |
| | | CTAGTGCATGAATAGATTCTCTCCTGATTATTTATCACATA |
| | | GCCCCTTAGCCAGTTGTATATTATTCTTGTGGTTTGTGAC |
| | | CCAATTAAGTCCTACTTTACATATGCTTTAAGAATCGATGG |
| | | GGGATGCTTCATGTGAACGTGGGAGTTCAGCTGCTTCTC |
| | | TTGCCTAAGTATTCCTTTCCTGATCACTATGCATTTTAAAG |
| | | TTAAACATTTTTAAGTATTTCAGATGCTTTAGAGAGATTTT |
| | | TTTTCCATGACTGCATTTTACTGTACAGATTGCTGCTTCTG |
| | | CTATATTTGTGATATAGGAATTAAGAGGATACACACGTTT |
| | | GTTTCTTCGTGCCTGTTTTATGTGCACACATTAGGCATTG |
| | | AGACTTCAAGCTTTTCTTTTTTTGTCCACGTATCTTTGGGT |
| | | CTTTGATAAAGAAAAGAATCCCTGTTCATTGTAAGCACTTT |
| | | TACGGGGCGGGTGGGGAGGGGTGCTCTGCTGGTCTTCA |
| | | ATTACCAAGAATTCTCCAAAACAATTTTCTGCAGGATGATT |
| | | GTACAGAATCATTGCTTATGACATGATCGCTTTCTACACT |
| | | GTATTACATAAATAAATTAAATAAAATAACCCCGGGCAAG |
| | | ACTTTTCTTTGAAGGATGACTACAGACATTAAATAATCGAA |
| | | GTAATTTTGGGTGGGGAGAAGAGGCAGATTCAATTTTCTT |
| | | TAACCAGTCTGAAGTTTCATTTATGATACAAAAGAAGATG |
| | | AAAATGGAAGTGGCAATATAAGGGGATGAGGAAGGCATG |
| | | CCTGGACAAACCCTTCTTTTAAGATGTGTCTTCAATTTGTA |
| | | TAAAATGGTGTTTTCATGTAAATAAATACATTCTTGGAGGA |
| | | GCACCATTG |
| 14 | ENSP00000351796 | >TCONS_00180781\|ENST00000358918 |
| | | (SEQ ID NO: 14) |
| | | GATCCCACTCGCACAGCAGCGCACTCGGTGCCCCGCGC |
| | | AGGGTCGCGATGCTGCCCGGTTTGGCACTGCTCCTGCTG |
| | | GCCGCCTGGACGGCTCGGGCGCTGGAGGTACCCACTGA |
| | | TGGTAATGCTGGCCTGCTGGCTGAACCCCAGATTGCCAT |

TABLE 3-continued

| APP_transcrips_final | | |
|---|---|---|
| Number of variants | Ensembl_protein_id/ UniProt_id | Fasta_Formatted_DNA_sequences_with_cufflinks_ transcript_ids_and_corres-ponding_Ensembl_ids |
| | | GTTCTGTGGCAGACTGAACATGCACATGAATGTCCAGAAT<br>GGGAAGTGGGATTCAGATCCATCAGGGACCAAAACCTGC<br>ATTGATACCAAGGAAGGCATCCTGCAGTATTGCCAAGAA<br>GTCTACCCTGAACTGCAGATCACCAATGTGGTAGAAGCC<br>AACCAACCAGTGACCATCCAGAACTGGTGCAAGCGGGGC<br>CGCAAGCAGTGCAAGACCCATCCCCACTTTGTGATTCCC<br>TACCGCTGCTTAGTTGGTGAGTTTGTAAGTGATGCCCTTC<br>TCGTTCCTGACAAGTGCAAATTCTTACACCAGGAGAGGAT<br>GGATGTTTGCGAAACTCATCTTCACTGGCACACCGTCGC<br>CAAAGAGACATGCAGTGAGAAGAGTACCAACTTGCATGA<br>CTACGGCATGTTGCTGCCCTGCGGAATTGACAAGTTCCG<br>AGGGGTAGAGTTTGTGTGTTGCCCACTGGCTGAAGAAAG<br>TGACAATGTGGATTCTGCTGATGCGGAGGAGGATGACTC<br>GGATGTCTGGTGGGGCGGAGCAGACACAGACTATGCAG<br>ATGGGAGTGAAGACAAAGTAGTAGAAGTAGCAGAGGAGG<br>AAGAAGTGGCTGAGGTGGAAGAAGAAGAAGCCGATGATG<br>ACGAGGACGATGAGGATGGTGATGAGGTAGAGGAAGAG<br>GCTGAGGAACCCTACGAAGAAGCCACAGAGAGAACCACC<br>AGCATTGCCACCACCACCACCACCACCACAGAGTCTGTG<br>GAAGAGGTGGTTCGAGAGGTGTGCTCTGAACAAGCCGA<br>GACGGGGCCGTGCCGAGCAATGATCTCCCGCTGGTACTT<br>TGATGTGACTGAAGGGAAGTGTGCCCCATTCTTTTACGG<br>CGGATGTGGCGGCAACCGGAACAACTTTGACACAGAAGA<br>GTACTGCATGGCCGTGTGTGGCAGCGCCATGTCCCAAAG<br>TTTACTCAAGACTACCCAGGAACCTCTTGCCCGAGATCCT<br>GTTAAACTTCCTACAACAGCAGCCAGTACCCCTGATGCC<br>GTTGACAAGTATCTCGAGACACCTGGGGATGAGAATGAA<br>CATGCCCATTTCCAGAAAGCCAAAGAGAGGCTTGAGGCC<br>AAGCACCGAGAGAGAATGTCCCAGGTCATGAGAGAATGG<br>GAAGAGGCAGAACGTCAAGCAAAGAACTTGCCTAAAGCT<br>GATAAGAAGGCAGTTATCCAGCATTTCCAGGAGAAAGTG<br>GAATCTTTGGAACAGGAAGCAGCCAACGAGAGACAGCAG<br>CTGGTGGAGACACACATGGCCAGAGTGGAAGCCATGCTC<br>AATGACCGCCGCCGCCTGGCCCTGGAGAACTACATCACC<br>GCTCTGCAGGCTGTTCCTCCTCGGCCTCGTCACGTGTTC<br>AATATGCTAAAGAAGTATGTCCGCGCAGAACAGAAGGAC<br>AGACAGCACACCCTAAAGCATTTCGAGCATGTGCGCATG<br>GTGGATCCCAAGAAAGCCGCTCAGATCCGGTCCCAGGTT<br>ATGACACACCTCCGTGTGATTTATGAGCGCATGAATCAGT<br>CTCTCTCCCTGCTCTACAACGTGCCTGCAGTGGCCGAGG<br>AGATTCAGGATGAAGTTGATGAGCTGCTTCAGAAAGAGC<br>AAAACTATTCAGATGACGTCTTGGCCAACATGATTAGTGA<br>ACCAAGGATCAGTTACGGAAACGATGCTCTCATGCCATCT<br>TTGACCGAAACGAAAACCACCGTGGAGCTCCTTCCCGTG<br>AATGGAGAGTTCAGCCTGGACGATCTCCAGCCGTGGCAT<br>TCTTTTGGGGCTGACTCTGTGCCAGCCAACACAGAAAAC<br>GAAGGTTCTGGGTTGACAAATATCAAGACGGAGGAGATC<br>TCTGAAGTGAAGATGGATGCAGAATTCCGACATGACTCA<br>GGATATGAAGTTCATCATCAAAAATTGGTGTTCTTTGCAG<br>AAGATGTGGGTTCAAACAAAGGTGCAATCATTGGACTCAT<br>GGTGGGCGGTGTTGTCATAGCGACAGTGATCGTCATCAC<br>CTTGGTGATGCTGAAGAAGAAACAGTACACATCCATTCAT<br>CATGGTGTGGTGGAGGTTGACGCCGCTGTCACCCCAGA<br>GGAGCGCCACCTGTCCAAGATGCAGCAGAACGGCTACG<br>AAAATCCAACCTACAAGTTCTTTGAGCAGATGCAGAACTA<br>GACCCCCGCCACAGCAGCCTCTGAAGTTGGACAGCAAAA<br>CCATTGCTTCACTACCCATCGG |
| 15 | ENSP00000352760 | >TCONS_00180777\|ENST00000359726<br>(SEQ ID NO: 15)<br>GTCGGATGATTCAAGCTCACGGGGACGAGCAGGAGCGC<br>TCTCGACTTTTCTAGAGCCTCAGCGTCCTAGGACTCACCT<br>TTCCCTGATCCTGCACCGTCCCTCTCCTGGCCCCAGACT<br>CTCCCTCCCACTGTTCACGAAGCCCAGGTACCCACTGAT<br>GGTAATGCTGGCCTGCTGGCTGAACCCCAGATTGCCATG<br>TTCTGTGGCAGACTGAACATGCACATGAATGTCCAGAATG<br>GGAAGTGGGATTCAGATCCATCAGGGACCAAAACCTGCA<br>TTGATACCAAGGAAGGCATCCTGCAGTATTGCCAAGAAG<br>TCTACCCTGAACTGCAGATCACCAATGTGGTAGAAGCCA<br>ACCAACCAGTGACCATCCAGAACTGGTGCAAGCGGGGC<br>CGCAAGCAGTGCAAGACCCATCCCCACTTTGTGATTCCC<br>TACCGCTGCTTAGTTGGTGAGTTTGTAAGTGATGCCCTTC<br>TCGTTCCTGACAAGTGCAAATTCTTACACCAGGAGAGGAT<br>GGATGTTTGCGAAACTCATCTTCACTGGCACACCGTCGC<br>CAAAGAGACATGCAGTGAGAAGAGTACCAACTTGCATGA |

TABLE 3-continued

APP_transcrips_final

| Number of variants | Ensembl_protein_id/ UniProt_id | Fasta_Formatted_DNA_sequences_with_cufflinks_ transcript_ids_and_corres-ponding_Ensembl_ids |
|---|---|---|
| | | CTACGGCATGTTGCTGCCCTGCGGAATTGACAAGTTCCG<br>AGGGGTAGAGTTTGTGTGTTGCCCACTGGCTGAAGAAAG<br>TGACAATGTGGATTCTGCTGATGCGGAGGAGGATGACTC<br>GGATGTCTGGTGGGGCGGAGCAGACACAGACTATGCAG<br>ATGGGAGTGAAGACAAAGTAGTAGAAGTAGCAGAGGAGG<br>AAGAAGTGGCTGAGGTGGAAGAAGAAGAAGCCGATGATG<br>ACGAGGACGATGAGGATGGTGATGAGGTAGAGGAAGAG<br>GCTGAGGAACCCTACGAAGAAGCCACAGAGAGAACCACC<br>AGCATTGCCACCACCACCACCACCACCACAGAGTCTGTG<br>GAAGAGGTGGTTCGAGTTCCTACAACAGCAGCCAGTACC<br>CCTGATGCCGTTGACAAGTATCTCGAGACACCTGGGGAT<br>GAGAATGAACATGCCCATTTCCAGAAAGCCAAAGAGAGG<br>CTTGAGGCCAAGCACCGAGAGAGAATGTCCCAGGTCATG<br>AGAGAATGGGAAGAGGCAGAACGTCAAGCAAAGAACTTG<br>CCTAAAGCTGATAAGAAGGCAGTTATCCAGCATTTCCAGG<br>AGAAAGTGGAATCTTTGGAACAGGAAGCAGCCAACGAGA<br>GACAGCAGCTGGTGGAGACACACATGGCCAGAGTGGAA<br>GCCATGCTCAATGACCGCCGCCGCCTGGCCCTGGAGAA<br>CTACATCACCGCTCTGCAGGCTGTTCCTCCTCGGCCTCG<br>TCACGTGTTCAATATGCTAAAGAAGTATGTCCGCGCAGAA<br>CAGAAGGACAGACAGCACACCCTAAAGCATTTCGAGCAT<br>GTGCGCATGGTGGATCCCAAGAAAGCCGCTCAGATCCG<br>GTCCCAGGTTATGACACACCTCCGTGTGATTTATGAGCG<br>CATGAATCAGTCTCTCTCCCTGCTCTACAACGTGCCTGCA<br>GTGGCCGAGGAGATTCAGGATGAAGTTGATGAGCTGCTT<br>CAGAAAGAGCAAAACTATTCAGATGACGTCTTGGCCAACA<br>TGATTAGTGAACCAAGGATCAGTTACGGAAACGATGCTCT<br>CATGCCATCTTTGACCGAAACGAAAACCACCGTGGAGCT<br>CCTTCCCGTGAATGGAGAGTTCAGCCTGGACGATCTCCA<br>GCCGTGGCATTCTTTTGGGGCTGACTCTGTGCCAGCCAA<br>CACAGAAAACGAAGTTGAGCCTGTTGATGCCCGCCCTGC<br>TGCCGACCGAGGACTGACCACTCGACCAGGTTCTGGGTT<br>GACAAATATCAAGACGGAGGAGATCTCTGAAGTGAAGAT<br>GGATGCAGAATTCCGACATGACTCAGGATATGAAGTTCAT<br>CATCAAAAATTGGTGTTCTTTGCAGAAGATGTGGGTTCAA<br>ACAAAGGTGCAATCATTGGACTCATGGTGGGCGGTGTTG<br>TCATAGCGACAGTGATCGTCATCACCTTGGTGATGCTGAA<br>GAAGAAACAGTACACATCCATTCATCATGGTGTGGTGGA<br>GGTTGACGCCGCTGTCACCCCAGAGGAGCGCCACCTGT<br>CCAAGATGCAGCAGAACGGCTACGAAAATCCAACCTACA<br>AGTTCTTTGAGCAGATGCAGAACTAGACCCCCGCCACAG<br>CAGCCTCTGAAGTTGGACAGCAAAACCATTGCTTCACTAC<br>CCATCGGTGTCCATTTATAGAATAATGTGGGAAGAAACAA<br>ACCCGTTTTATGATTTACTCATTATCGCCTTTTGACAGCTG<br>TGCTGTAACACAAGTAGATGCCTGAACTTGAATTAATCCA<br>CACATCAGTAATGTATTCTATCTCTCTTTACATTTTGGTCT<br>CTATACTACATTATTAATGGGTTTTGTGTACTGTAAAGAAT<br>TTAGCTGTATCAAACTAGTGCATGAATAGATTCTCTCCTG<br>ATTATTTATCACATAGCCCCTTAGCCAGTTGTATATTATTC<br>TTGTGGTTTGTGACCCAATTAAGTCCTACTTTACATATGCT<br>TTAAGAATCGATGGGGGATGCTTCATGTGAACGTGGGAG<br>TTCAGCTGCTTCTCTTGCCTAAGTATTCCTTTCCTGATCAC<br>TATGCATTTTAAAGTTAAACATTTTTAAGTATTTCAGATGC<br>TTTAGAGAGATTTTTTTTCCATGACTGCATTTTACTGTACA<br>GATTGCTGCTTCTGCTATATTTGTGATATAGGAATTAAGA<br>GGATACACACGTTTGTTTCTTCGTGCCTGTTTTATGTGCA<br>CACATTAGGCATTGAGACTTCAAGCTTTTCTTTTTTTGTCC<br>ACGTATCTTTGGGTCTTTGATAAAGAAAAGAATCCCTGTT<br>CATTGTAAGCACTTTTACGGGGGGGTGGGGAGGGGTG<br>CTCTGCTGGTCTTCAATTACCAAGAATTCTCCAAAACAATT<br>TTCTGCAGGATGATTGTACAGAATCATTGCTTATGACATG<br>ATCGCTTTCTACACTGTATTACATAAATAAATTAAATAAAA<br>TAACCCCGGGCAAGACTTTTCTTTGAAGGATGACTACAGA<br>CATTAAATAATCGAAGTAATTTTGGGTGGGGAGAAGAGG<br>CAGATTCAATTTTCTTTAACCAGTCTGAAGTTTCATTTATG<br>ATACAAAAGAAGATGAAAATGGAAGTGGCAATATAAGGG<br>GATGAGGAAGGCATGCCTGGACAAACCCTTCTTTTAAGAT<br>GTGTCTTCAATTTGTATAAAATGGTGTTTTCATGTAAATAA<br>ATACATTCTTGGAGGAGC |
| 16 | ENSP00000387483 | >TCONS_00180766\|ENST00000440126<br>(SEQ ID NO: 16)<br>AGAGTTCCGGAGGCTTTGGTTGTCCATTGTTAGCTTAGAA<br>GTTGGCGCAGTGTGCGTGTGATCCACGCCTAAATAGCAC<br>AGCCTTGCTGTGCGTGGTAGAAGTTGGGTTAGTGTTGAC |

TABLE 3-continued

| APP_transcrips_final | | |
|---|---|---|
| Number of variants | Ensembl_protein_id/ UniProt_id | Fasta_Formatted_DNA_sequences_with_cufflinks_ transcript_ids_and_corres-ponding_Ensembl_ids |
| | | ATGCTGTTGACTCACCCTCCCGAGGATGGAAGCTCTGGC<br>CTGGGTCAAGTTGTGGTCACTGCAGTTAACAGTTTGTTGA<br>TCTCAGGGAGTATTCCACAGTTGCTGATGTAATTGACAAT<br>GATTGGAGCCAGCTCTTCCCCAGATTCAAATGGACCAATT<br>AGAGGACTTGTTGGTTCTGTTTATCAACTATGTACCCACT<br>GATGGTAATGCTGGCCTGCTGGCTGAACCCCAGATTGCC<br>ATGTTCTGTGGCAGACTGAACATGCACATGAATGTCCAGA<br>ATGGGAAGTGGGATTCAGATCCATCAGGGACCAAAACCT<br>GCATTGATACCAAGGAAGGCATCCTGCAGTATTGCCAAG<br>AAGTCTACCCTGAACTGCAGATCACCAATGTGGTAGAAG<br>CCAACCAACCAGTGACCATCCAGAACTGGTGCAAGCGGG<br>GCCGCAAGCAGTGCAAGACCCATCCCCACTTTGTGATTC<br>CCTACCGCTGCTTAGTTGGTGAGTTTGTAAGTGATGCCCT<br>TCTCGTTCCTGACAAGTGCAAATTCTTACACCAGGAGAGG<br>ATGGATGTTTGCGAAACTCATCTTCACTGGCACACCGTCG<br>CCAAAGAGACATGCAGTGAGAAGAGTACCAACTTGCATG<br>ACTACGGCATGTTGCTGCCCTGCGGAATTGACAAGTTCC<br>GAGGGGTAGAGTTTGTGTGTTGCCCACTGGCTGAAGAAA<br>GTGACAATGTGGATTCTGCTGATGCGGAGGAGGATGACT<br>CGGATGTCTGGTGGGGCGGAGCAGACACAGACTATGCA<br>GATGGGAGTGAAGACAAAGTAGTAGAAGTAGCAGAGGAG<br>GAAGAAGTGGCTGAGGTGGAAGAAGAAGAAGCCGATGAT<br>GACGAGGACGATGAGGATGGTGATGAGGTAGAGGAAGA<br>GGCTGAGGAACCCTACGAAGAAGCCACAGAGAGAACCA<br>CCAGCATTGCCACCACCACCACCACCACCACAGAGTCTG<br>TGGAAGAGGTGGTTCGAGAGGTGTGCTCTGAACAAGCCG<br>AGACGGGGCCGTGCCGAGCAATGATCTCCCGCTGGTAC<br>TTTGATGTGACTGAAGGGAAGTGTGCCCCATTCTTTTACG<br>GCGGATGTGGCGGCAACCGGAACAACTTTGACACAGAAG<br>AGTACTGCATGGCCGTGTGTGGCAGCGCCATTCCTACAA<br>CAGCAGCCAGTACCCCTGATGCCGTTGACAAGTATCTCG<br>AGACACCTGGGGATGAGAATGAACATGCCCATTTCCAGA<br>AAGCCAAAGAGAGGCTTGAGGCCAAGCACCGAGAGAGA<br>ATGTCCCAGGTCATGAGAGAATGGGAAGAGGCAGAACGT<br>CAAGCAAAGAACTTGCCTAAAGCTGATAAGAAGGCAGTTA<br>TCCAGCATTTCCAGGAGAAAGTGGAATCTTTGGAACAGG<br>AAGCAGCCAACGAGAGACAGCAGCTGGTGGAGACACAC<br>ATGGCCAGAGTGGAAGCCATGCTCAATGACCGCCGCCG<br>CCTGGCCCTGGAGAACTACATCACCGCTCTGCAGGCTGT<br>TCCTCCTCGGCCTCGTCACGTGTTCAATATGCTAAAGAAG<br>TATGTCCGCGCAGAACAGAAGGACAGACAGCACACCCTA<br>AAGCATTTCGAGCATGTGCGCATGGTGGATCCCAAGAAA<br>GCCGCTCAGATCCGGTCCCAGGTTATGACACACCTCCGT<br>GTGATTTATGAGCGCATGAATCAGTCTCTCTCCCTGCTCT<br>ACAACGTGCCTGCAGTGGCCGAGGAGATTCAGGATGAAG<br>TTGATGAGCTGCTTCAGAAAGAGCAAAACTATTCAGATGA<br>CGTCTTGGCCAACATGATTAGTGAACCAAGGATCAGTTAC<br>GGAAACGATGCTCTCATGCCATCTTTGACCGAAACGAAAA<br>CCACCGTGGAGCTCCTTCCCGTGAATGGAGAGTTCAGCC<br>TGGACGATCTCCAGCCGTGGCATTCTTTTGGGGCTGACT<br>CTGTGCCAGCCAACACAGAAAACGAAGTTGAGCCTGTTG<br>ATGCCCGCCCTGCTGCCGACCGAGGACTGACCACTCGA<br>CCAGGTTCTGGGTTGACAAATATCAAGACGGAGGAGATC<br>TCTGAAGTGAAGATGGATGCAGAATTCCGACATGACTCA<br>GGATATGAAGTTCATCATCAAAAATTGGTGTTCTTTGCAG<br>AAGATGTGGGTTCAAACAAAGGTGCAATCATTGGACTCAT<br>GGTGGGCGGTGTTGTCATAGCGACAGTGATCGTCATCAC<br>CTTGGTGATGCTGAAGAAGAAACAGTACACATCCATTCAT<br>CATGGTGTGGTGGAGGTTGACGCCGCTGTCACCCCAGA<br>GGAGCGCCACCTGTCCAAGATGCAGCAGAACGGCTACG<br>AAAATCCAACCTACAAGTTCTTTGAGCAGATGCAGAACTA<br>GACCCCCGCCACAGCAGCCTCTGAAGTTGGACAGCAAAA<br>CCATTGCTTCACTACCCATCGGTGTCCATTTATAGAATAA<br>TGTGGGAAGAAACAAACCCGTTTTATGATTTACTCATTAT<br>CGCCTTTTGACAGCTGTGCTGTAACACAAGTAGATGCCT<br>GAACTTGAATTAATCCACACATCAGTAATGTATTCTATCTC<br>TCTTTACATTTTGGTCTCTATACTACATTATTAATGGGTTTT<br>GTGTACTGTAAAGAATTTAGCTGTATCAAACTAGTGCATG<br>AATAGATTCTCTCCTGATTATTTATCACATAGCCCCTTAGC<br>CAGTTGTATATTATTCTTGTGGTTTGTGACCCAATTAAGTC<br>CTACTTTACATATGCTTTAAGAATCGATGGGGGATGCTTC<br>ATGTGAACGTGGGAGTTCAGCTGCTTCTCTTGCCTAAGTA<br>TTCCTTTCCTGATCACTATGCATTTTAAAGTTAAACATTTTT<br>AAGTATTTCAGATGCTTTAGAGAGATTTTTTTTCCATGACT<br>GCATTTTACTGTACAGATTGCTGCTTCTGCTATATTTGTGA |

TABLE 3-continued

| APP_transcrips_final | | |
|---|---|---|
| Number of variants | Ensembl_protein_id/ UniProt_id | Fasta_Formatted_DNA_sequences_with_cufflinks_ transcript_ids_and_corres-ponding_Ensembl_ids |
| | | TATAGGAATTAAGAGGATACACACGTTTGTTTCTTCGTGC CTGTTTTATGTGCACACATTAGGCATTGAGACTTCAAGCT TTTCTTTTTTTGTCCACGTATCTTTGGGTCTTTGATAAAGA AAAGAATCCCTGTTCATTGTAAGCACTTTTACGGGGCGG GTGGGGAGGGGTGCTCTGCTGGTCTTCAATTACCAAGAA TTCTCCAAAACAATTTTCTGCAGGATGATTGTACAGAATC ATTGCTTATGACATGATCGCTTTCTACACTGTATTACATAA ATAAATTAAATAAAATAACCCCGGGCAAGACTTTTCTTTGA AGGATGACTACAGACATTAAATAATCGAAGTAATTTTGGG TGGGGAGAAGAGGCAGATTCAATTTTCTTTAACCAGTCTG AAGTTTCATTTATGATACAAAAGAAGATGAAAATGGAAGT GGCAATATAAGGGGATGAGGAAGGCATGCCTGGACAAAC CCTTCTTTTAAGATGTGTCTTCAATTTGTATAAAATGGTGT TTTCATGTAAATAAATACATTCTTGGAGGAGCACCATTG |
| 17 | ENSP00000387483 | >TCONS_00180778\|ENST00000440126 (SEQ ID NO: 17) AGAGTTCCGGAGGCTTTGGTTGTCCATTGTTAGCTTAGAA GTTGGCGCAGTGTGCGTGTGATCCACGCCTAAATAGCAC AGCCTTGCTGTGCGTGGTAGAAGTTGGGTTAGTGTTGAC ATGCTGTTGACTCACCCTCCCGAGGATGGAAGCTCTGGC CTGGGTCAAGTTGTGGTCACTGCAGTTAACAGTTTGTTGA TCTCAGGGAGTATTCCACAGTTGCTGATGTAATTGACAAT GATTGGAGCCAGCTCTTCCCCAGATTCAAATGGACCAATT AGAGGACTTGTTGGTTCTGTTTATCAACTATGTACCCACT GATGGTAATGCTGGCCTGCTGGCTGAACCCCAGATTGCC ATGTTCTGTGGCAGACTGAACATGCACATGAATGTCCAGA ATGGGAAGTGGGATTCAGATCCATCAGGGACCAAAACCT GCATTGATACCAAGGAAGGCATCCTGCAGTATTGCCAAG AAGTCTACCCTGAACTGCAGATCACCAATGTGGTAGAAG CCAACCAACCAGTGACCATCCAGAACTGGTGCAAGCGGG GCCGCAAGCAGTGCAAGACCCATCCCCACTTTGTGATTC CCTACCGCTGCTTAGTTGGTGAGTTTGTAAGTGATGCCCT TCTCGTTCCTGACAAGTGCAAATTCTTACACCAGGAGAGG ATGGATGTTTGCGAAACTCATCTTCACTGGCACACCGTCG CCAAAGAGACATGCAGTGAGAAGAGTACCAACTTGCATG ACTACGGCATGTTGCTGCCCTGCGGAATTGACAAGTTCC GAGGGGTAGAGTTTGTGTGTTGCCCACTGGCTGAAGAAA GTGACAATGTGGATTCTGCTGATGCGGAGGAGGATGACT CGGATGTCTGGTGGGGCGGAGCAGACACAGACTATGCA GATGGGAGTGAAGACAAAGTAGTAGAAGTAGCAGAGGAG GAAGAAGTGGCTGAGGTGGAAGAAGAAGAAGCCGATGAT GACGAGGACGATGAGGATGGTGATGAGGTAGAGGAAGA GGCTGAGGAACCCTACGAAGAAGCCACAGAGAGAACCA CCAGCATTGCCACCACCACCACCACCACCACAGAGTCTG TGGAAGAGGTGGTTCGAGAGGTGTGCTCTGAACAAGCCG AGACGGGGCCGTGCCGAGCAATGATCTCCCGCTGGTAC TTTGATGTGACTGAAGGGAAGTGTGCCCCATTCTTTTACG GCGGATGTGGCGGCAACCGGAACAACTTTGACACAGAAG AGTACTGCATGGCCGTGTGTGGCAGCGCCATTCCTACAA CAGCAGCCAGTACCCCTGATGCCGTTGACAAGTATCTCG AGACACCTGGGGATGAGAATGAACATGCCCATTTCCAGA AAGCCAAAGAGAGGCTTGAGGCCAAGCACCGAGAGAGA ATGTCCCAGGTCATGAGAGAATGGGAAGAGGCAGAACGT CAAGCAAAGAACTTGCCTAAAGCTGATAAGAAGGCAGTTA TCCAGCATTTCCAGGAGAAAGTGGAATCTTTGGAACAGG AAGCAGCCAACGAGAGACAGCAGCTGGTGGAGACACAC ATGGCCAGAGTGGAAGCCATGCTCAATGACCGCCGCCG CCTGGCCCTGGAGAACTACATCACCGCTCTGCAGGCTGT TCCTCCTCGGCCTCGTCACGTGTTCAATATGCTAAAGAAG TATGTCCGCGCAGAACAGAAGGACAGACAGCACACCCTA AAGCATTTCGAGCATGTGCGCATGGTGGATCCCAAGAAA GCCGCTCAGATCCGGTCCCAGGTTATGACACACCTCCGT GTGATTTATGAGCGCATGAATCAGTCTCTCTCCCTGCTCT ACAACGTGCCTGCAGTGGCCGAGGAGATTCAGGATGAAG TTGATGAGCTGCTTCAGAAAGAGCAAAACTATTCAGATGA CGTCTTGGCCAACATGATTAGTGAACCAAGGATCAGTTAC GGAAACGATGCTCTCATGCCATCTTTGACCGAAACGAAAA CCACCGTGGAGCTCCTTCCCGTGAATGGAGAGTTCAGCC TGGACGATCTCCAGCCGTGGCATTCTTTTGGGGCTGACT CTGTGCCAGCCAACACAGAAAACGAAGTTGAGCCTGTTG ATGCCCGCCCTGCTGCCGACCGAGGACTGACCACTCGA CCAGGTTCTGGGTTGACAAATATCAAGACGGAGGAGATC TCTGAAGTGAAGATGGATGCAGAATTCCGACATGACTCA GGATATGAAGTTCATCATCAAAAATTGGTGTTCTTTGCAG |

TABLE 3-continued

| APP_transcrips_final | | |
|---|---|---|
| Number of variants | Ensembl_protein_id/ UniProt_id | Fasta_Formatted_DNA_sequences_with_cufflinks_ transcript_ids_and_corres-ponding_Ensembl_ids |
| | | AAGATGTGGGTTCAAACAAAGGTGCAATCATTGGACTCAT<br>GGTGGGCGGTGTTGTCATAGCGACAGTGATCGTCATCAC<br>CTTGGTGATGCTGAAGAAGAAACAGTACACATCCATTCAT<br>CATGGTGTGGTGGAGGTTGACGCCGCTGTCACCCCAGA<br>GGAGCGCCACCTGTCCAAGATGCAGCAGAACGGCTACG<br>AAAATCCAACCTACAAGTTCTTTGAGCAGATGCAGAACTA<br>GACCCCCGCCACAGCAGCCTCTGAAGTTGGACAGCAAAA<br>CCATTGCTTCACTACCCATCGGTGTCCATTTATAGAATAA<br>TGTGGGAAGAAACAAACCCGTTTTATGATTTACTCATTAT<br>CGCCTTTTGACAGCTGTGCTGTAACACAAGTAGATGCCT<br>GAACTTGAATTAATCCACACATCAGTAATGTATTCTATCTC<br>TCTTTACATTTTGGTCTCTATACTACATTATTAATGGGTTTT<br>GTGTACTGTAAAGAATTTAGCTGTATCAAACTAGTGCATG<br>AATAGATTCTCTCCTGATTATTTATCACATAGCCCCTTAGC<br>CAGTTGTATATTATTCTT |
| 18 | ENSP00000396923 | >TCONS_00180783\|ENST00000448850<br>(SEQ ID NO: 18)<br>ACTGCAGATCACCAATGTGGTAGAAGCCAACCAACCAGT<br>GACCATCCAGAACTGGTGCAAGCGGGGCCGCAAGCAGT<br>GCAAGACCCATCCCCACTTTGTGATTCCCTACCGCTGCTT<br>AGTTGGTGAGTTTGTAAGTGATGCCCTTCTCGTTCCTGAC<br>AAGTGCAAATTCTTACACCAGGAGAGGATGGATGTTTGC<br>GAAACTCATCTTCACTGGCACACCGTCGCCAAAGAGACA<br>TGCAGTGAGAAGAGTACCAACTTGCATGACTACGGCATG<br>TTGCTGCCCTGCGGAATTGACAAGTTCCGAGGGGTAGAG<br>TTTGTGTGTTGCCCACTGGCTGAAGAAAGTGACAATGTG<br>GATTCTGCTGATGCGGAGGAGGATGACTCGGATGTCTGG<br>TGGGGCGGAGCAGACACAGACTATGCAGATGGGAGTGA<br>AGACAAAGTAGTAGAAGTAGCAGAGGAGGAAGAAGTGGC<br>TGAGGTGGAAGAAGAAGAAGCCGATGATGACGAGGACG<br>ATGAGGATGGTGATGAGGTAGAGGAAGAGGCTGAGGAA<br>CCCTACGAAGAAGCCACAGAGAGAACCACCAGCATTGCC<br>ACCACCACCACCACCACCACCACAGAGTCTGTGGAAGAGGTG<br>GTTCGAGAGGTGTGCTCTGAACAAGCCGAGACGGGGCC<br>GTGCCGAGCAATGATCTCCCGCTGGTACTTTGATGTGAC<br>TGAAGGGAAGTGTGCCCCATTCTTTTACGGCGGATGTGG<br>CGGCAACCGGAACAACTTTGACACAGAAGAGTACTGCAT<br>GGCCGTGTGTGGCAGCGCCATTCCTACAACAGCAGCCA<br>GTACCCCTGATGCCGTTGACAAGTATCTCGAGACACCTG<br>GGGATGAGAATGAACATGCCCATTTCCAGAAAGCCAAAG<br>AGAGGCTTGAGGCCAAGCACCGAGAGAGAATGTCCCAG<br>GTCATGAGAGAATGGGAAGAGGCAGAACGTCAAGCAAAG<br>AACTTGCCTAAAGCTGATAAGAAGGCAGTTATCCAGCATT<br>TCCAGGAGAAAGTGGAATCTTTGGAACAGGAAGCAGCCA<br>ACGAGAGACAGCAGCTGGTGGAGACACACATGGCCAGA<br>GTGGAAGCCATGCTCAATGACCGCCGCCGCCTGGCCCT<br>GGAGAACTACATCACCGCTCTGCAGGCTGTTCCTCCTCG<br>GCCTCGTCACGTGTTCAATATGCTAAAGAAGTATGTCCGC<br>GCAGAACAGAAGGACAGACAGCACACCCTAAAGCATTTC<br>GAGCATGTGCGCATGGTGGATCCCAAGAAAGCCGCTCAG<br>ATCCGGTCCCAGGTTATGACACACCTCCGTGTGATTTATG<br>AGCGCATGAATCAGTCTCTCTCCCTGCTCTACAACGTGC<br>CTGCAGTGGCCGAGGAGATTCAGGATGAAGTTGGTGCAG<br>TGGCTCATGCCTGTAATTCCAGCATTTTGGGAGGCCAAG<br>GTGGGCAGATGACTTGAGCCCAGAAGTTCAAGACCAGAA<br>TGGGAAACATGGCAAGACCACATTTCTACAAAAAAATTAT<br>CCAGGCATGATAACATCTATTTGTAGTCCCAGCTACTCAG<br>GAGGCTGTGGTGGGAGGATCTCCTGAGCCTGGGGTGGC<br>TGAGGCTGCAGTGAGCCTTGATCACGCCACCTGGGCAAT<br>AGAGCAAGACCCTGTCTCAAAAAAAGGAAGAAAAAGACT<br>ATTATTTCCCCCATTGAATGGTCTTGGCACTATTACACAAA<br>ATCAATTGTCCATAGATAATATGGGTTTATTTCTTAATTCT<br>TAGTTCTTTTCTTTGATCTGTGTGCCTGTGCTTACTGTAGT<br>ACCACACTGTTTTGATTATTGTAGCTTTGTAGTAAATTTTG<br>AAATCAGC |
| 19 | ENSP00000398879 | >TCONS_00180779\|ENST00000439274<br>(SEQ ID NO: 19)<br>CAGCAGCGCACTCGGTGCCCCGCGCAGGGTCGCGATGC<br>TGCCCGGTTTGGCACTGCTCCTGCTGGCCGCCTGGACG<br>GCTCGGGCGCTGGAGGTCTACCCTGAACTGCAGATCACC<br>AATGTGGTAGAAGCCAACCAACCAGTGACCATCCAGAAC<br>TGGTGCAAGCGGGGCCGCAAGCAGTGCAAGACCCATCC<br>CCACTTTGTGATTCCCTACCGCTGCTTAGTTGGTGAGTTT |

TABLE 3-continued

APP_transcrips_final

| Number of variants | Ensembl_protein_id/ UniProt_id | Fasta_Formatted_DNA_sequences_with_cufflinks_ transcript_ids_and_corres-ponding_Ensembl_ids |
|---|---|---|
| | | GTAAGTGATGCCCTTCTCGTTCCTGACAAGTGCAAATTCT<br>TACACCAGGAGAGGATGGATGTTTGCGAAACTCATCTTCA<br>CTGGCACACCGTCGCCAAAGAGACATGCAGTGAGAAGAG<br>TACCAACTTGCATGACTACGGCATGTTGCTGCCCTGCGG<br>AATTGACAAGTTCCGAGGGGTAGAGTTTGTGTGTTGCCC<br>ACTGGCTGAAGAAAGTGACAATGTGGATTCTGCTGATGC<br>GGAGGAGGATGACTCGGATGTCTGGTGGGGCGGAGCAG<br>ACACAGACTATGCAGATGGGAGTGAAGACAAAGTAGTAG<br>AAGTAGCAGAGGAGGAAGAAGTGGCTGAGGTGGAAGAA<br>GAAGAAGCCGATGATGACGAGGACGATGAGGATGGTGAT<br>GAGGTAGAGGAAGAGGCTGAGGAACCCTACGAAGAAGC<br>CACAGAGAGAACCACCAGCATTGCCACCACCACCACCAC<br>CACCACAGAGTCTGTGGAAGAGGTGGTTCGAGAGGTGTG<br>CTCTGAACAAGCCGAGACGGGGCCGTGCCGAGCAATGA<br>TCTCCCGCTGGTACTTTGATGTGACTGAAGGGAAGTGTG<br>CCCCATTCTTTTACGGCGGATGTGGCGGCAACCGGAACA<br>ACTTTGACACAGAAGAGTACTGCATGGCCGTGTGTGGCA<br>GCGCCATGTCCCAAAGTTTACTCAAGACTACCCAGGAAC<br>CTCTTGCCCGAGATCCTGTTAAACTTCCTACAACAGCAGC<br>CAGTACCCCTGATGCCGTTGACAAGTATCTCGAGACACC<br>TGGGGATGAGAATGAACATGCCCATTTCCAGAAAGCCAA<br>AGAGAGGCTTGAGGCCAAGCACCGAGAGAGAATGTCCC<br>AGGTCATGAGAGAATGGGAAGAGGCAGAACGTCAAGCAA<br>AGAACTTGCCTAAAGCTGATAAGAAGGCAGTTATCCAGCA<br>TTTCCAGGAGAAAGTGGAATCTTTGGAACAGGAAGCAGC<br>CAACGAGAGACAGCAGCTGGTGGAGACACACATGGCCA<br>GAGTGGAAGCCATGCTCAATGACCGCCGCCGCCTGGCC<br>CTGGAGAACTACATCACCGCTCTGCAGGCTGTTCCTCCT<br>CGGCCTCGTCACGTGTTCAATATGCTAAAGAAGTATGTCC<br>GCGCAGAACAGAAGGACAGACAGCACACCCTAAAGCATT<br>TCGAGCATGTGCGCATGGTGGATCCCAAGAAAGCCGCTC<br>AGATCCGGTCCCAGGTTATGACACACCTCCGTGTGATTTA<br>TGAGCGCATGAATCAGTCTCTCTCCCTGCTCTACAACGTG<br>CCTGCAGTGGCCGAGGAGATTCAGGATGAAGTTGATGAG<br>CTGCTTCAGAAAGAGCAAAACTATTCAGATGACGTCTTGG<br>CCAACATGATTAGTGAACCAAGGATCAGTTACGGAAACG<br>ATGCTCTCATGCCATCTTTGACCGAAACGAAAACCACCGT<br>GGAGCTCCTTCCCGTGAATGGAGAGTTCAGCCTGGACGA<br>TCTCCAGCCGTGGCATTCTTTTGGGGCTGACTCTGTGCC<br>AGCCAACACAGAAAACGAAGTTGAGCCTGTTGATGCCCG<br>CCCTGCTGCCGACCGAGGACTGACCACTCGACCAGGTTC<br>TGGGTTGACAAATATCAAGACGGAGGAGATCTCTGAAGT<br>GAAGATGGATGCAGAATTCCGACATGACTCAGGATATGA<br>AGTTCATCATCAAAAATTGGTGTTCTTTGCAGAAGATGTG<br>GGTTCAAACAAAGGTGCAATCATTGGACTCATGGTGGGC<br>GGTGTTGTCATAGCGACAGTGATCGTCATCACCTTGGTG<br>ATGCTGAAGAAGAAACAGTACACATCCATTCATCATGGTG<br>TGGTGGAGGTTGACGCCGCTGTCACCCCAGAGGAGCGC<br>CACCTGTCCAAGATGCAGCAGAACGGCTACGAAAATCCA<br>ACCTACAAGTTCTTTGAGCAGATGCAGAACTAGACCCCC<br>GCCACAGCAGCCTCTGAAGTTGGACAGCAAAACCATTGC<br>TTCACTACCCATCGGTGTCCATTTATAGAATAATGTGGGA<br>AGAAACAAACCCGTTTTATGATTTACTCATTATCGCCTTTT<br>GACAGCTGTGCTGTAACACAAGTAGATGCCTGAACTTGA<br>ATTAATCCACACATCAGTAATGTATTCTATCTCTCTTTACA<br>TTTTGGTCTCTATACTACATTATTAATGGGTTTTGTGTACT<br>GTAAAGAATTTAGCTGTATCAAACTAGTGCATGAATAGAT<br>TCTCTCCTGATTATTTATCACATAGCCCCTTAGCCAGTTGT<br>ATATTATTCT |
| 20 | ENSP00000406539 | >TCONS_00180784\|ENST00000415997<br>(SEQ ID NO: 20)<br>GGGCGGAGCAGACACAGACTATGCAGATGGGAGTGAAG<br>ACAAAGTAGTAGAAGTAGCAGAGGAGGAAGAAGTGGCTG<br>AGGTGGAAGAAGAAGAAGCCGATGATGACGAGGACGAT<br>GAGGATGGTGATGAGGTAGAGGAAGAGGCTGAGGAACC<br>CTACGAAGAAGCCACAGAGAGAACCACCAGCATTGCCAC<br>CACCACCACCACCACCACAGAGTCTGTGGAAGAGGTGGT<br>TCGAGTGTCCCAAAGTTTACTCAAGACTACCCAGGAACCT<br>CTTGCCCGAGATCCTGTTAAACTTCCTACAACAGCAGCCA<br>GTACCCCTGATGCCGTTGACAAGTATCTCGAGACACCTG<br>GGGATGAGAATGAACATGCCCATTTCCAGAAAGCCAAAG<br>AGAGGCTTGAGGCCAAGCACCGAGAGAGAATGTCCCAG<br>GTCATGAGAGAATGGGAAGAGGCAGAACGTCAAGCAAAG |

TABLE 3-continued

| APP_transcrips_final | | |
|---|---|---|
| Number of variants | Ensembl_protein_id/ UniProt_id | Fasta_Formatted_DNA_sequences_with_cufflinks_ transcript_ids_and_corres-ponding_Ensembl_ids |
| | | AACTTGCCTAAAGCTGATAAGAAGGCAGTTATCCAGCATT TCCAGGAGAAAGTGGAATCTTTGGAACAGGAAGCA |
| 21 | Uniprot_id: P05067 | >TCONS_00180780\|ENST00000464867 (SEQ ID NO: 21) ATCCTTGCCAACCTCTCAACCAGGATTTAACTTCTGCTTTT CCCCCATTTTCAAAAATTATAGCATGTATTTAAAGGCAGC AGAAGCCTTACTTTCAGGTTTCCCTTACCCTTTCATTTCTT TTTGTTCAAAATAGGTAGTAATTGAAGTTTTAAATATAGGG TATCATTTTTCTTTAAGAGTCATTTATCAATTTTCTTCTAAC TTCAGGCCTAGAAAGAAGTTTTGGGTAGGCTTTGTCTTAC AGTGTTATTATTTATGAGTAAAACTAATTGGTTGTCCTGCA TACTTTAATTATGATGTAATACAGGTTCTGGGTTGACAAAT ATCAAGACGGAGGAGATCTCTGAAGTGAAGATGGATGCA GAATTCCGACATGACTCAGGATATGAAGTTCATCATCAAA AATTGGTGTTCTTTGCAGAAGATGTGGGTTCAAACAAAGG TGCAATCATTGGACTCATGGTGGGCGGTGTTGTCATAGC GACAGTGATCGTCATCACCTTGGTGATGCTGAAGAAGAA ACAGTACACATCCATTCATCATGGTGTGGTGGAGGTTGA CGCCGCTGTCACCCCAGAGGAGCGCCACCTGTCCAAGA TGCAGCAGAACGGCTACGAAAATCCAACCTACAAGTTCTT TGAGCAGATGCAGAACTAGACCCCCGCCACAGCAGCCTC TGAAGTTGGACAGCAAAACCATTGCTTCACTACCCATCGG TGTCCATTTATAGAATAATGTGGGAAGAAACAAACCCGTT TTATGATTTACTCATTATCGCCTTTTGACAGCTGTGCTGTA ACACAAGTAGATGCC |
| 22 | Uniprot_id: P05067 | >TCONS_00180785\|ENST00000491395 (SEQ ID NO: 22) CAGACTATGCAGATGGGAGTGAAGACAAAGTAGTAGAAG TAGCAGAGGAGGAAGAAGTGGCTGAGGTGGAAGAAGAA GAAGCCGATGATGACGAGGACGATGAGGATGGTGATGA GGTAGAGGAAGAGGCTGAGGAACCCTACGAAGAAGCCA CAGAGAGAACCACCAGCATTGCCACCACCACCACCACCA CCACAGAGTCTGTGGAAGAGGTGGTTCGAGAGGTGTGCT CTGAACAAGCCGAGACGGGGCCGTGCCGAGCAATGATC TCCCGCTGGTACTTTGATGTGACTGAAGGGAAGTGTGCC CCATTCTTTTACGGCGGATGTGGCGGCAACCGGAACAAC TTTGACACAGAAGAGTACTGCATGGCCGTGTGTGGCAGC GCCATGTCCCAAAGTTTACTCAAGACTACCCAGGAACCTC TTGCCCGAGATCCTGTTAAACGTACGTTGTCATTCACCTG AGGGAAGGGAAGAGGGGAGGAGGATGCTGCTTGGTTCA CATAACTCCAGCATCATCACCTTCTTTGCATGGTTTTGTG TTTCTTGAACACCTGTCTTAGTAAAATGTTTCTTCCCATTA CCTTGCTTGTAATTACATCTGATTTTGCCAGACA |
| 23 | Uniprot_id: P05067 | >TCONS_00180786\|ENST00000474136 (SEQ ID NO: 23) CGAGAGCACGCGGAGGAGCGTGCGCGGGGGCCCCGGG AGACGGCGGCGGTGGCGGCGCGGGCAGAGCAAGGACG CGGCGGATCCCACTCGCACAGCAGCGCACTCGGTGCCC CGCGCAGGGTCGCGATGCTGCCCGGTTTGGCACTGCTC CTGCTGGCCGCCTGGACGGCTCGGGCGCTGGAGGTACC CACTGATGGTAATGCTGGCCTGCTGGCTGAACCCCAGAT TGCCATGTTCTGTGGCAGACTGAACATGCACATGAATGTC CAGAATGGGAAGTGGGATTCAGATCCATCAGGGACCAAA ACCTGCATTGATACCAAGGAAGGCATCCTGCAGTATTGC CAAGAAGTCTACCCTGAACTGCAGATCACCAATGTGGTA GAAGCCAACCAACCAGTGACCATCCAGAACTGGTGCAAG CGGGGCCGCAAGCAGTGCAAGACCCATCCCCACTTTGTG ATTCCCTACCGCTGCTTAGTTGGTGAGTTTGTAAGTGATG CCCTTCTCGTTCCTGACAAGTGCAAATTCTTACACCAGGA GAGGATGGATGTTTGCGAAACTCATCTTCACTGGCACAC CGTCGCCAAAGAGACATGCAGTGAGAAGAGTACCAACTT GCATGACTACGGCATGTTGCTGCCCTGCGGAATTGACAA GTTCCGAGGGGTAGAGTTTGTGTGTTGCCCACTGGCTGA AGAAAGTGACAATGTGGATTCTGCTGATGCGGAGGAGGA TGACTCGGATGTCTGGTGGGGCGGAGCAGACACAGACT ATGCAGATGGGAGTGAAGACAAAGTAGTAGAAGTAGCAG AGGAGGAAGAAGTGGCTGAGGTGGAAGAAGAAGAAGCC GATGATGACGAGGACGATGAGGATGGTGATGAGGTAGA GGAAGAGGCTGAGGAACCCTACGAAGAAGCCACAGAGA GAACCACCAGCATTGCCACCACCACCACCACCACCACAG AGTCTGTGGAAGAGGTGGTTCGAGAGAAGTGGTATAAGG AAGTACATTCTGGCCAGGCACGATGGCTCATGCTGTAAT |

TABLE 3-continued

| APP_transcrips_final | | |
|---|---|---|
| Number of variants | Ensembl_protein_id/ UniProt_id | Fasta_Formatted_DNA_sequences_with_cufflinks_ transcript_ids_and_corres-ponding_Ensembl_ids |
| | | CCCAGCACTTTGGGAGGCCGAGGTGGGTGCATCACCTG<br>AGGTCAGGAGTTTGAGACCAGCCTGGCCAACATGGTGAA<br>ACCCCTCGCTACTAAAAATACAAAAATTAGCCGGGCGTG<br>GTGGCACACACCTGTGGTCCCAGCTACTCGGGAGGCTG<br>AAGCAGGAGAATCGCTTGAACCCGGGAGACGGAGGTTG<br>CAGTAAGCCGAGTTCACTCCATTGTACTCTAGCCTGGGT<br>GACAGAGCGAGATTCGTCTCAAAAAAAAAAAAA |
| 24 | Uniprot_id: P05067 | >TCONS_00180787\|ENST00000463070<br>(SEQ ID NO: 24)<br>GTAACATTCTAAAGGTAGTAGGGTCTTGATTGGGTTGCTT<br>AGGCATTAAAAGGCTGTTTAACTTGTCTTGAAGTCTATCTT<br>TCCTTGATGTCTTCTGCGGTAAGAACACTGTGATACAGAT<br>GGAATGACGGGAAGTGGTTTTCCTTTCTTTCAGTTGGTGA<br>GTTTGTAAGTGATGCCCTTCTCGTTCCTGACAAGTGCAAA<br>TTCTTACACCAGGAGAGGATGGATGTTTGCGAAACTCATC<br>TTCACTGGCACACCGTCGCCAAAGAGACATGCAGTGAGA<br>AGAGTACCAACTTGCATGACTACGGCATGTTGCTGCCCT<br>GCGGAATTGACAAGTTCCGAGGGGTAGAGTTTGTGTGTT<br>GCCCACTGGCTGAAGAAAGTGACAATGTGGATTCTGCTG<br>ATGCGGAGGAGGATGACTCGGATGTCTGGTGGGGCGGA<br>GCAGACACAGACTATGCAGATGGGAGTGAAGACAAAGTA<br>GTAGAAGTAGCAGAGGAGGAAGAAGTGGCTGAGGTGGA<br>AGAAGAAGAAGCCGATGATGACGAGGACGATGAGGATG<br>GTGATGAGGTAGAGGAAGAGGCTGAGGAACCC |
| 25 | Uniprot_id: P05067 | >TCONS_00180788\|ENST00000548570<br>(SEQ ID NO: 25)<br>ACTGGAGGGCTGAGAAGAGACTGATGGCATTTGTTGTTC<br>TTGACCTTGAAAGAAGAGTTGCAGATTGTTGGAGCAAGG<br>CCAGATGGTAATAGGTTGGAAAGAACAAGTGAGGGGCGT<br>GAGAGTGACAGTCTACAACCCCGTTAAGAAGTTATCTGTG<br>AAAATGCCTCTTCCTGTCTTGATTATAGCCTCCCTCGCAC<br>ATGGCTTTCTGAGTATGTTGGTGAGTTTGTAAGTGATGCC<br>CTTCTCGTTCCTGACAAGTGCAAATTCTTACACCAGGAGA<br>GGATGGATGTTTGCGAAACTCATCTTCACTGGCACACCG<br>TCGCCAAAGAGACATGCAGTGAGAAGAGTACCAACTTGC<br>ATGACT |
| 26 | Uniprot_id: P05067 | >TCONS_00180789\|ENST00000462267<br>(SEQ ID NO: 26)<br>CTGAACATGCACATGAATGTCCAGAATGGGAAGTGGGAT<br>TCAGATCCATCAGGGACCAAAACCTGCATTGATACCAAG<br>GAAGGCATCCTGCAGTATTGCCAAGAAGTCTACCCTGAA<br>CTGCAGATCACCAATGTGGTAGAAGCCAACCAACCAGTG<br>ACCATCCAGAACTGGTGCAAGCGGGGCCGCAAGCAGTG<br>CAAGACCCATCCCCACTTTGTGATTCCCTACCGCTGCTTA<br>GGTGAGCCGGCCGGCCGTGGGGCTGGTGTTGATTGGGG<br>GCCTGGTCTTGAGGGAAGAAAAAGAGGATGCTCCTGTTA<br>GGTCACATACACAGACTTGTTCTTCAGCACATTGCCACTC<br>TGTGTTGTACTGTGTTTTGGACTCTTGCAGTTACATTCTGT<br>GCACTGACCCTATAGGAGCAGTATTTTTGAGTTCCCTGCC<br>TCAGAATGAATTTACCCAGGGTGTATATTGAAATTACAAAT<br>TCCTGGGCCAGTTCCAGGACTCCTGAATGAAAAATGCCT<br>ATAGTAGCGGATCCGGGAATTCTTATTTTACCGTATCGCA<br>TAGATGATTCTCATGAACAGGGGCCTTGTGTGTTTCTTCA<br>CATAGACTTTCTAGAAGAAAGAATCTAATGTGAAGCTGCA<br>GCATTTTGTTAATTTCTAAAAAAAAAAAAAAAAA |
| 27 | Uniprot_id: P05067 | >TCONS_00180790\|ENST00000466453<br>(SEQ ID NO: 27)<br>GGCGCGGCCTCTTCCCTGGCAGCTCTGGGGACTCTGGT<br>TTAGTTCCCCTGGGGGCACAGGATGCTGGGGAGGGTCC<br>GAAGGGTCTTTTTTTTAGGGTGCAGATAAAAGGATCGAAT<br>TGAGTGAAGATTAAGACGGAGAAGATGGCGCCTCTGCAG<br>TGCAGCAAAGAAAAGCTGTGTGGAGGCTGCAGCCTAGTG<br>AAATCCACCCACCACTAGGTACCCACTGATGGTAATGCT<br>GGCCTGCTGGCTGAACCCCAGATTGCCATGTTCTGTGGC<br>AGACTGAACATGCACATGAATGTCCAGAATGGGAAGTGG<br>GATTCAGATCCATCAGGGACCAAAACCTGCATTGATACCA<br>AGGAAGGCATCCTGCAGTATTGC |

REFERENCES

1. Hartley J L, Davenport M, Kelly D A. Biliary atresia. Lancet. 2009; 374 (9702): 1704-13.
2. Wong K K, Chung P H, Chan I H, Lan L C, Tam P K. Performing Kasai portoenterostomy beyond 60 days of life is not necessarily associated with a worse outcome. Journal of pediatric gastroenterology and nutrition. 2010; 51 (5): 631-4.
3. Chung P H, Wong K K, Tam P K. Predictors for failure after Kasai operation. Journal of pediatric surgery. 2015; 50 (2): 293-6.
4. Ernest van Heurn L W, Saing H, Tam P K. Cholangitis after hepatic portoenterostomy for biliary atresia: a multivariate analysis of risk factors. The Journal of pediatrics. 2003; 142 (5): 566-71.
5. Khong P L, Ooi C G, Saing H, Chan K L, Wong W H, Tam P K, et al. Portal venous velocity in the follow-up of patients with biliary atresia after Kasai portoenterostomy. Journal of pediatric surgery. 2002; 37 (6): 873-6.
6. van Heurn L W, Saing H, Tam P K. Portoenterostomy for biliary atresia: Long-term survival and prognosis after esophageal variceal bleeding. Journal of pediatric surgery. 2004; 39 (1): 6-9.
7. Wong K K, Fan A H, Lan L C, Lin S C, Tam P K. Effective antibiotic regime for postoperative acute cholangitis in biliary atresia—an evolving scene. Journal of pediatric surgery. 2004; 39 (12): 1800-2.
8. Picelli S, Faridani O R, Bjorklund A K, Winberg G, Sagasser S, Sandberg R. Full-length RNA-seq from single cells using Smart-seq2. Nature protocols. 2014; 9 (1): 171-81.

What is claimed is:

1. A method for diagnosing biliary atresia (BA) or assessing risk of developing BA in an infant, comprising:

(i) determining expression level of amyloid precursor protein (APP) in a liver sample taken from the infant;

(ii) detecting an increase in the APP expression level from step (i) when compared with a standard control value; and (iii) determining the infant as having BA or at risk of developing BA.

2. The method of claim 1, wherein the APP expression level is APP mRNA level.

3. The method of claim 1, wherein the APP expression level is APP protein level.

4. The method of claim 2, wherein step (i) comprises a reverse transcription polymerase chain reaction (RT-PCR).

5. The method of claim 3, wherein step (i) comprises an immunoassay.

6. The method of claim 1, wherein the liver sample is a liver biopsy.

7. The method of claim 1, further comprising a step, following step (iii), of performing at least one additional diagnostic test for BA.

8. The method of claim 7, further comprising a step, following step (iii), of treating the infant with Kasai procedure.

9. A method for assessing effectiveness of Kasai procedure in an infant who has BA and has undergone Kasai procedure, comprising:

(i) determining expression level of amyloid precursor protein (APP) in a liver sample taken from the infant;

(ii) detecting an increase in the APP expression level from step (i) when compared with a standard control value; and (iii) determining the Kasai procedure as ineffective.

10. The method of claim 9, wherein the APP expression level is APP mRNA level.

11. The method of claim 9, wherein the APP expression level is APP protein level.

12. The method of claim 10, wherein step (i) comprises an RT-PCR.

13. The method of claim 11, wherein step (i) comprises an immunoassay.

14. The method of claim 9, wherein the liver sample is a liver biopsy.

15. The method of claim 9, further comprising a step, following step (iii), of performing liver transplant.

* * * * *

SEQUENCE LISTING

<160> NUMBER OF SEQ ID NOS: 27

<210> SEQ ID NO 1
<211> LENGTH: 3383
<212> TYPE: DNA
<213> ORGANISM: Artificial sequence
<220> FEATURE:
<223> OTHER INFORMATION: Description of sequence: amyloid precursor protein coding sequence

<400> SEQUENCE: 1
ggtacccact gatggtaatg ctggcctgct ggctgaaccc cagattgcca tgttctgtgg 60
cagactgaac atgcacatga atgtccagaa tgggaagtgg gattcagatc catcagggac 120
caaaacctgc attgatacca aggaaggcat cctgcagtat tgccaagaag tctaccctga 180
actgcagatc accaatgtgg tagaagccaa ccaaccagtg accatccaga actggtgcaa 240
gcggggccgc aagcagtgca agacccatcc ccactttgtg attccctacc gctgcttagt 300
tggtgagttt gtaagtgatg cccttctcgt tcctgacaag tgcaaattct tacaccagga 360
gaggatggat gtttgcgaaa ctcatcttca ctggcacacc gtcgccaaag agacatgcag 420
tgagaagagt accaacttgc atgactacgg catgttgctg ccctgcggaa ttgacaagtt 480
ccgaggggta gagtttgtgt gttgcccact ggctgaagaa agtgacaatg tggattctgc 540
tgatgcggag gaggatgact cggatgtctg gtggggcgga gcagacacag actatgcaga 600
tgggagtgaa gacaaagtag tagaagtagc agaggaggaa gaagtggctg aggtggaaga 660
agaagaagcc gatgatgacg aggacgatga ggatggtgat gaggtagagg aagaggctga 720
ggaaccctac gaagaagcca cagagagaac caccagcatt gccaccacca ccaccaccac 780
cacagagtct gtggaagagg tggttcgaga ggtgtgctct gaacaagccg agacggggcc 840
gtgccgagca atgatctccc gctggtactt tgatgtgact gaagggaagt gtgccccatt 900
cttttacggc ggatgtggcg gcaaccggaa caactttgac acagaagagt actgcatggc 960
cgtgtgtggc agcgccatgt cccaaagttt actcaagact acccaggaac ctcttgcccg 1020
agatcctgtt aaacttccta caacagcagc cagtacccct gatgccgttg acaagtatct 1080
cgagacacct ggggatgaga atgaacatgc ccatttccag aaagccaaag agaggcttga 1140
ggccaagcac cgagagagaa tgtcccaggt catgagagaa tgggaagagg cagaacgtca 1200
agcaaagaac ttgcctaaag ctgataagaa ggcagttatc cagcatttcc aggagaaagt 1260
ggaatctttg gaacaggaag cagccaacga gagacagcag ctggtggaga cacacatggc 1320
cagagtggaa gccatgctca atgaccgccg ccgcctggcc ctggagaact acatcaccgc 1380

```
tctgcaggct gttcctcctc ggcctcgtca cgtgttcaat atgctaaaga agtatgtccg   1440
cgcagaacag aaggacagac agcacaccct aaagcatttc gagcatgtgc gcatggtgga   1500
tcccaagaaa gccgctcaga tccggtccca ggttatgaca cacctccgtg tgatttatga   1560
gcgcatgaat cagtctctct ccctgctcta caacgtgcct gcagtggccg aggagattca   1620
ggatgaagtt gatgagctgc ttcagaaaga gcaaaactat tcagatgacg tcttggccaa   1680
catgattagt gaaccaagga tcagttacgg aaacgatgct ctcatgccat ctttgaccga   1740
aacgaaaacc accgtggagc tccttcccgt gaatggagag ttcagcctgg acgatctcca   1800
gccgtggcat tcttttgggg ctgactctgt gccagccaac acagaaaacg aagttgagcc   1860
tgttgatgcc cgccctgctg ccgaccgagg actgaccact cgaccaggtt ctgggttgac   1920
aaatatcaag acggaggaga tctctgaagt gaagatggat gcagaattcc gacatgactc   1980
aggatatgaa gttcatcatc aaaaattggt gttctttgca gaagatgtgg gttcaaacaa   2040
aggtgcaatc attggactca tggtgggcgg tgttgtcata gcgacagtga tcgtcatcac   2100
cttggtgatg ctgaagaaga aacagtacac atccattcat catggtgtgg tggaggttga   2160
cgccgctgtc accccagagg agcgccacct gtccaagatg cagcagaacg gctacgaaaa   2220
tccaacctac aagttctttg agcagatgca gaactagacc cccgccacag cagcctctga   2280
agttggacag caaaaccatt gcttcactac ccatcggtgt ccatttatag aataatgtgg   2340
gaagaaacaa acccgtttta tgatttactc attatcgcct tttgacagct gtgctgtaac   2400
acaagtagat gcctgaactt gaattaatcc acacatcagt aatgtattct atctctcttt   2460
acattttggt ctctatacta cattattaat gggttttgtg tactgtaaag aatttagctg   2520
tatcaaacta gtgcatgaat agattctctc ctgattattt atcacatagc cccttagcca   2580
gttgtatatt attcttgtgg tttgtgaccc aattaagtcc tactttacat atgctttaag   2640
aatcgatggg ggatgcttca tgtgaacgtg ggagttcagc tgcttctctt gcctaagtat   2700
tcctttcctg atcactatgc attttaaagt taaacatttt taagtatttc agatgcttta   2760
gagagatttt ttttccatga ctgcatttta ctgtacagat tgctgcttct gctatatttg   2820
tgatatagga attaagagga tacacacgtt tgtttcttcg tgcctgtttt atgtgcacac   2880
attaggcatt gagacttcaa gcttttcttt ttttgtccac gtatctttgg gtctttgata   2940
aagaaaagaa tccctgttca ttgtaagcac ttttacgggg cgggtgggga ggggtgctct   3000
gctggtcttc aattaccaag aattctccaa aacaattttc tgcaggatga ttgtacagaa   3060
tcattgctta tgacatgatc gctttctaca ctgtattaca taaataaatt aaataaaata   3120
accccgggca agacttttct ttgaaggatg actacagaca ttaaataatc gaagtaattt   3180
tgggtgggga gaagaggcag attcaatttt ctttaaccag tctgaagttt catttatgat   3240
acaaaagaag atgaaaatgg aagtggcaat ataaggggat gaggaaggca tgcctggaca   3300
aacccttctt ttaagatgtg tcttcaattt gtataaaatg gtgttttcat gtaaataaat   3360
acattcttgg aggagcacca ttg                                           3383
```

<210> SEQ ID NO 2
<211> LENGTH: 3423
<212> TYPE: DNA
<213> ORGANISM: Artificial sequence
<220> FEATURE:
<223> OTHER INFORMATION: Description of sequence: amyloid precursor protein coding sequence

<400> SEQUENCE: 2

```
attgagtgaa gattaagacg gagaagatgg cgcctctgca gtgcagcaaa gaaaagctgt     60
gtggaggctg cagcctagtg aaatccaccc accactaggt acccactgat ggtaatgctg    120
gcctgctggc tgaaccccag attgccatgt tctgtggcag actgaacatg cacatgaatg    180
tccagaatgg gaagtgggat tcagatccat cagggaccaa aacctgcatt gataccaagg    240
aaggcatcct gcagtattgc caagaagtct accctgaact gcagatcacc aatgtggtag    300
aagccaacca accagtgacc atccagaact ggtgcaagcg gggccgcaag cagtgcaaga    360
cccatcccca ctttgtgatt ccctaccgct gcttagttgg tgagtttgta agtgatgccc    420
ttctcgttcc tgacaagtgc aaattcttac accaggagag gatggatgtt tgcgaaactc    480
atcttcactg gcacaccgtc gccaaagaga catgcagtga gaagagtacc aacttgcatg    540
actacggcat gttgctgccc tgcggaattg acaagttccg aggggtagag tttgtgtgtt    600
gcccactggc tgaagaaagt gacaatgtgg attctgctga tgcggaggag gatgactcgg    660
atgtctggtg gggcggagca gacacagact atgcagatgg gagtgaagac aaagtagtag    720
aagtagcaga ggaggaagaa gtggctgagg tggaagaaga agaagccgat gatgacgagg    780
acgatgagga tggtgatgag gtagaggaag aggctgagga accctacgaa gaagccacag    840
agagaaccac cagcattgcc accaccacca ccaccaccac agagtctgtg gaagaggtgg    900
ttcgagaggt gtgctctgaa caagccgaga cggggccgtg ccgagcaatg atctcccgct    960
ggtactttga tgtgactgaa gggaagtgtg ccccattctt ttacggcgga tgtggcggca   1020
accggaacaa ctttgacaca gaagagtact gcatggccgt gtgtggcagc gccattccta   1080
caacagcagc cagtacccct gatgccgttg acaagtatct cgagacacct ggggatgaga   1140
atgaacatgc ccatttccag aaagccaaag agaggcttga ggccaagcac cgagagagaa   1200
tgtcccaggt catgagagaa tgggaagagg cagaacgtca agcaaagaac ttgcctaaag   1260
ctgataagaa ggcagttatc cagcatttcc aggagaaagt ggaatctttg gaacaggaag   1320
cagccaacga gagacagcag ctggtggaga cacacatggc cagagtggaa gccatgctca   1380
atgaccgccg ccgcctggcc ctggagaact acatcaccgc tctgcaggct gttcctcctc   1440
ggcctcgtca cgtgttcaat atgctaaaga agtatgtccg cgcagaacag aaggacagac   1500
agcacaccct aaagcatttc gagcatgtgc gcatggtgga tcccaagaaa gccgctcaga   1560
tccggtccca ggttatgaca cacctccgtg tgatttatga gcgcatgaat cagtctctct   1620
ccctgctcta caacgtgcct gcagtggccg aggagattca ggatgaagtt gatgagctgc   1680
ttcagaaaga gcaaaactat tcagatgacg tcttggccaa catgattagt gaaccaagga   1740
tcagttacgg aaacgatgct ctcatgccat ctttgaccga aacgaaaacc accgtggagc   1800
tccttcccgt gaatggagag ttcagcctgg acgatctcca gccgtggcat tcttttgggg   1860
ctgactctgt gccagccaac acagaaaacg aagttgagcc tgttgatgcc cgccctgctg   1920
ccgaccgagg actgaccact cgaccaggtt ctgggttgac aaatatcaag acggaggaga   1980
tctctgaagt gaagatggat gcagaattcc gacatgactc aggatatgaa gttcatcatc   2040
aaaaattggt gttctttgca gaagatgtgg gttcaaacaa aggtgcaatc attggactca   2100
tggtgggcgg tgttgtcata gcgacagtga tcgtcatcac cttggtgatg ctgaagaaga   2160
aacagtacac atccattcat catggtgtgg tggaggttga cgccgctgtc accccagagg   2220
agcgccacct gtccaagatg cagcagaacg gctacgaaaa tccaacctac aagttctttg   2280
agcagatgca gaactagacc cccgccacag cagcctctga agttggacag caaaaccatt   2340
```

```
gcttcactac ccatcggtgt ccatttatag aataatgtgg gaagaaacaa acccgtttta   2400

tgatttactc attatcgcct tttgacagct gtgctgtaac acaagtagat gcctgaactt   2460

gaattaatcc acacatcagt aatgtattct atctctcttt acattttggt ctctatacta   2520

cattattaat gggttttgtg tactgtaaag aatttagctg tatcaaacta gtgcatgaat   2580

agattctctc ctgattattt atcacatagc cccttagcca gttgtatatt attcttgtgg   2640

tttgtgaccc aattaagtcc tactttacat atgctttaag aatcgatggg ggatgcttca   2700

tgtgaacgtg ggagttcagc tgcttctctt gcctaagtat tcctttcctg atcactatgc   2760

atttaaagt taaacatttt taagtatttc agatgcttta gagagatttt ttttccatga   2820

ctgcatttta ctgtacagat tgctgcttct gctatatttg tgatatagga attaagagga   2880

tacacacgtt tgtttcttcg tgcctgtttt atgtgcacac attaggcatt gagacttcaa   2940

gcttttcttt ttttgtccac gtatctttgg gtctttgata aagaaaagaa tccctgttca   3000

ttgtaagcac ttttacgggg cgggtgggga ggggtgctct gctggtcttc aattaccaag   3060

aattctccaa aacaatttc tgcaggatga ttgtacagaa tcattgctta tgacatgatc   3120

gctttctaca ctgtattaca taaataaatt aaataaaata accccgggca agacttttct   3180

ttgaaggatg actacagaca ttaaataatc gaagtaattt tgggtgggga gaagaggcag   3240

attcaatttt ctttaaccag tctgaagttt catttatgat acaaaagaag atgaaaatgg   3300

aagtggcaat ataaggggat gaggaaggca tgcctggaca aacccttctt ttaagatgtg   3360

tcttcaattt gtataaaatg gtgttttcat gtaaataaat acattcttgg aggagcacca   3420

ttg                                                                3423
```

```
<210> SEQ ID NO 3
<211> LENGTH: 3204
<212> TYPE: DNA
<213> ORGANISM: Artificial sequence
<220> FEATURE:
<223> OTHER INFORMATION: Description of sequence: amyloid precursor
      protein coding sequence

<400> SEQUENCE: 3

cgccgcgctc gggctccgtc agtttcctcg gcagcggtag gcgagagcac gcggaggagc     60

gtgcgcgggg gccccgggag acggcggcgg tggcggcgcg ggcagagcaa ggacgcggcg    120

gatcccactc gcacagcagc gcactcggtg ccccgcgcag ggtcgcgatg ctgcccggtt    180

tggcactgct cctgctggcc gcctggacgg ctcgggcgct ggaggtctac cctgaactgc    240

agatcaccaa tgtggtagaa gccaaccaac cagtgaccat ccagaactgg tgcaagcggg    300

gccgcaagca gtgcaagacc catccccact ttgtgattcc ctaccgctgc ttagttggtg    360

agtttgtaag tgatgccctt ctcgttcctg acaagtgcaa attcttacac caggagagga    420

tggatgtttg cgaaactcat cttcactggc acaccgtcgc caaagagaca tgcagtgaga    480

agagtaccaa cttgcatgac tacggcatgt tgctgccctg cggaattgac aagttccgag    540

gggtagagtt tgtgtgttgc ccactggctg aagaaagtga caatgtggat tctgctgatg    600

cggaggagga tgactcggat gtctggtggg gcggagcaga cacagactat gcagatggga    660

gtgaagacaa agtagtagaa gtagcagagg aggaagaagt ggctgaggtg gaagaagaag    720

aagccgatga tgacgaggac gatgaggatg gtgatgaggt agaggaagag gctgaggaac    780

cctacgaaga agccacagag agaaccacca gcattgccac caccaccacc accaccacag    840

agtctgtgga agaggtggtt cgagaggtgt gctctgaaca agccgagacg ggccgtgcc    900
```

-continued

```
gagcaatgat ctcccgctgg tactttgatg tgactgaagg gaagtgtgcc ccattctttt    960
acggcggatg tggcggcaac cggaacaact ttgacacaga agagtactgc atggccgtgt   1020
gtggcagcgc catgtcccaa agtttactca agactaccca ggaacctctt gcccgagatc   1080
ctgttaaact tcctacaaca gcagccagta cccctgatgc cgttgacaag tatctcgaga   1140
cacctgggga tgagaatgaa catgcccatt tccagaaagc caaagagagg cttgaggcca   1200
agcaccgaga gagaatgtcc cagcctcgtc acgtgttcaa tatgctaaag aagtatgtcc   1260
gcgcagaaca gaaggacaga cagcacaccc taaagcattt cgagcatgtg cgcatggtgg   1320
atcccaagaa agccgctcag atccggtccc aggttatgac acacctccgt gtgatttatg   1380
agcgcatgaa tcagtctctc tccctgctct acaacgtgcc tgcagtggcc gaggagattc   1440
aggatgaagt tgatgagctg cttcagaaag agcaaaacta ttcagatgac gtcttggcca   1500
acatgattag tgaaccaagg atcagttacg gaaacgatgc tctcatgcca tctttgaccg   1560
aaacgaaaac caccgtggag ctccttcccg tgaatggaga gttcagcctg gacgatctcc   1620
agccgtggca ttcttttggg gctgactctg tgccagccaa cacagaaaac gaagttgagc   1680
ctgttgatgc ccgccctgct gccgaccgag gactgaccac tcgaccaggt tctgggttga   1740
caaatatcaa gacggaggag atctctgaag tgaagatgga tgcagaattc cgacatgact   1800
caggatatga agttcatcat caaaaattgg tgttctttgc agaagatgtg ggttcaaaca   1860
aaggtgcaat cattggactc atggtgggcg gtgttgtcat agcgacagtg atcgtcatca   1920
ccttggtgat gctgaagaag aaacagtaca catccattca tcatggtgtg gtggaggttg   1980
acgccgctgt caccccagag gagcgccacc tgtccaagat gcagcagaac ggctacgaaa   2040
atccaaccta caagttcttt gagcagatgc agaactagac cccgccacag cagcctctg    2100
aagttggaca gcaaaaccat tgcttcacta cccatcggtg tccatttata gaataatgtg   2160
ggaagaaaca aacccgtttt atgatttact cattatcgcc ttttgacagc tgtgctgtaa   2220
cacaagtaga tgcctgaact tgaattaatc cacacatcag taatgtattc tatctctctt   2280
tacattttgg tctctatact acattattaa tgggttttgt gtactgtaaa gaatttagct   2340
gtatcaaact agtgcatgaa tagattctct cctgattatt tatcacatag ccccttagcc   2400
agttgtatat tattcttgtg gtttgtgacc caattaagtc ctactttaca tatgctttaa   2460
gaatcgatgg gggatgcttc atgtgaacgt gggagttcag ctgcttctct tgcctaagta   2520
ttcctttcct gatcactatg cattttaaag ttaaacattt ttaagtattt cagatgcttt   2580
agagagattt tttttccatg actgcatttt actgtacaga ttgctgcttc tgctatattt   2640
gtgatatagg aattaagagg atacacacgt ttgtttcttc gtgcctgttt tatgtgcaca   2700
cattaggcat tgagacttca agcttttctt tttttgtcca cgtatctttg ggtctttgat   2760
aaagaaaaga atccctgttc attgtaagca cttttacggg gcgggtgggg aggggtgctc   2820
tgctggtctt caattaccaa gaattctcca aaacaatttt ctgcaggatg attgtacaga   2880
atcattgctt atgacatgat cgctttctac actgtattac ataaataaat taaataaaat   2940
aaccccgggc aagacttttc tttgaaggat gactacagac attaaataat cgaagtaatt   3000
ttgggtgggg agaagaggca gattcaattt tctttaacca gtctgaagtt tcatttatga   3060
tacaaaagaa gatgaaaatg gaagtggcaa tataaggga tgaggaaggc atgcctggac    3120
aaacccttct tttaagatgt gtcttcaatt tgtataaaat ggtgttttca tgtaaataaa   3180
tacattcttg gaggagcacc attg                                          3204
```

```
<210> SEQ ID NO 4
<211> LENGTH: 3495
<212> TYPE: DNA
<213> ORGANISM: Artificial sequence
<220> FEATURE:
<223> OTHER INFORMATION: Description of sequence: amyloid precursor
      protein coding sequence

<400> SEQUENCE: 4

cgccgcgctc gggctccgtc agtttcctcg gcagcggtag gcgagagcac gcggaggagc     60

gtgcgcgggg gccccgggag acggcggcgg tggcggcgcg ggcagagcaa ggacgcggcg    120

gatcccactc gcacagcagc gcactcggtg ccccgcgcag ggtcgcgatg ctgcccggtt    180

tggcactgct cctgctggcc gcctggacgg ctcgggcgct ggaggtaccc actgatggta    240

atgctggcct gctggctgaa ccccagattg ccatgttctg tggcagactg aacatgcaca    300

tgaatgtcca gaatgggaag tgggattcag atccatcagg gaccaaaacc tgcattgata    360

ccaaggaagg catcctgcag tattgccaag aagtctaccc tgaactgcag atcaccaatg    420

tggtagaagc caaccaacca gtgaccatcc agaactggtg caagcggggc cgcaagcagt    480

gcaagaccca tccccacttt gtgattccct accgctgctt agttggtgag tttgtaagtg    540

atgcccttct cgttcctgac aagtgcaaat tcttacacca ggagaggatg gatgtttgcg    600

aaactcatct tcactggcac accgtcgcca aagagacatg cagtgagaag agtaccaact    660

tgcatgacta cggcatgttg ctgccctgcg gaattgacaa gttccgaggg gtagagtttg    720

tgtgttgccc actggctgaa gaaagtgaca atgtggattc tgctgatgcg gaggaggatg    780

actcggatgt ctggtggggc ggagcagaca cagactatgc agatgggagt gaagacaaag    840

tagtagaagt agcagaggag gaagaagtgg ctgaggtgga agaagaagaa gccgatgatg    900

acgaggacga tgaggatggt gatgaggtag aggaagaggc tgaggaaccc tacgaagaag    960

ccacagagag aaccaccagc attgccacca ccaccaccac caccacagag tctgtggaag   1020

aggtggttcg agaggtgtgc tctgaacaag ccgagacggg gccgtgccga gcaatgatct   1080

cccgctggta ctttgatgtg actgaaggga agtgtgcccc attcttttac ggcggatgtg   1140

gcggcaaccg gaacaacttt gacacagaag agtactgcat ggccgtgtgt ggcagcgcca   1200

ttcctacaac agcagccagt acccctgatg ccgttgacaa gtatctcgag acacctgggg   1260

atgagaatga acatgcccat ttccagaaag ccaaagagag gcttgaggcc aagcaccgag   1320

agagaatgtc ccaggtcatg agagaatggg aagaggcaga acgtcaagca aagaacttgc   1380

ctaaagctga taagaaggca gttatccagc atttccagga gaaagtggaa tctttggaac   1440

aggaagcagc caacgagaga cagcagctgg tggagacaca catggccaga gtggaagcca   1500

tgctcaatga ccgccgccgc ctggccctgg agaactacat caccgctctg caggctgttc   1560

ctcctcggcc tcgtcacgtg ttcaatatgc taaagaagta tgtccgcgca gaacagaagg   1620

acagacagca caccctaaag catttcgagc atgtgcgcat ggtggatccc aagaaagccg   1680

ctcagatccg gtcccaggtt atgacacacc tccgtgtgat ttatgagcgc atgaatcagt   1740

ctctctccct gctctacaac gtgcctgcag tggccgagga gattcaggat gaagttgatg   1800

agctgcttca gaaagagcaa aactattcag atgacgtctt ggccaacatg attagtgaac   1860

caaggatcag ttacggaaac gatgctctca tgccatcttt gaccgaaacg aaaaccaccg   1920

tggagctcct tcccgtgaat ggagagttca gcctggacga tctccagccg tggcattctt   1980

ttggggctga ctctgtgcca gccaacacag aaaacgaagg ttctgggttg acaaatatca   2040

agacggagga gatctctgaa gtgaagatgg atgcagaatt ccgacatgac tcaggatatg   2100
```

```
aagttcatca tcaaaaattg gtgttctttg cagaagatgt gggttcaaac aaaggtgcaa   2160

tcattggact catggtgggc ggtgttgtca tagcgacagt gatcgtcatc accttggtga   2220

tgctgaagaa gaaacagtac acatccattc atcatggtgt ggtggaggtt gacgccgctg   2280

tcaccccaga ggagcgccac ctgtccaaga tgcagcagaa cggctacgaa aatccaacct   2340

acaagttctt tgagcagatg cagaactaga cccccgccac agcagcctct gaagttggac   2400

agcaaaacca ttgcttcact acccatcggt gtccatttat agaataatgt gggaagaaac   2460

aaacccgttt tatgatttac tcattatcgc cttttgacag ctgtgctgta acacaagtag   2520

atgcctgaac ttgaattaat ccacacatca gtaatgtatt ctatctctct ttacattttg   2580

gtctctatac tacattatta atgggttttg tgtactgtaa agaatttagc tgtatcaaac   2640

tagtgcatga atagattctc tcctgattat ttatcacata gccccttagc cagttgtata   2700

ttattcttgt ggtttgtgac ccaattaagt cctactttac atatgcttta agaatcgatg   2760

ggggatgctt catgtgaacg tgggagttca gctgcttctc ttgcctaagt attcctttcc   2820

tgatcactat gcattttaaa gttaaacatt tttaagtatt tcagatgctt tagagagatt   2880

tttttccat gactgcattt tactgtacag attgctgctt ctgctatatt tgtgatatag   2940

gaattaagag gatacacacg tttgtttctt cgtgcctgtt ttatgtgcac acattaggca   3000

ttgagacttc aagcttttct ttttttgtcc acgtatcttt gggtctttga taaagaaaag   3060

aatccctgtt cattgtaagc acttttacgg ggcgggtggg gaggggtgct ctgctggtct   3120

tcaattacca agaattctcc aaaacaattt tctgcaggat gattgtacag aatcattgct   3180

tatgacatga tcgctttcta cactgtatta cataaataaa ttaaataaaa taaccccggg   3240

caagactttt ctttgaagga tgactacaga cattaaataa tcgaagtaat tttgggtggg   3300

gagaagaggc agattcaatt ttctttaacc agtctgaagt ttcatttatg atacaaaaga   3360

agatgaaaat ggaagtggca atataagggg atgaggaagg catgcctgga caaacccttc   3420

ttttaagatg tgtcttcaat ttgtataaaa tggtgttttc atgtaaataa atacattctt   3480

ggaggagcac cattg                                                    3495
```

```
<210> SEQ ID NO 5
<211> LENGTH: 3254
<212> TYPE: DNA
<213> ORGANISM: Artificial sequence
<220> FEATURE:
<223> OTHER INFORMATION: Description of sequence: amyloid precursor
      protein coding sequence

<400> SEQUENCE: 5

cgccgcgctc gggctccgtc agtttcctcg gcagcggtag gcgagagcac gcggaggagc     60

gtgcgcgggg gccccgggag acggcggcgg tggcggcgcg ggcagagcaa ggacgcggcg    120

gatcccactc gcacagcagc gcactcggtg ccccgcgcag ggtcgcgatg ctgcccggtt    180

tggcactgct cctgctggcc gcctggacgg ctcgggcgct ggaggtaccc actgatggta    240

atgctggcct gctggctgaa ccccagattg ccatgttctg tggcagactg aacatgcaca    300

tgaatgtcca gaatgggaag tgggattcag atccatcagg gaccaaaacc tgcattgata    360

ccaaggaagg catcctgcag tattgccaag aagtctaccc tgaactgcag atcaccaatg    420

tggtagaagc caaccaacca gtgaccatcc agaactggtg caagcggggc cgcaagcagt    480

gcaagaccca tccccacttt gtgattccct accgctgctt agttggtgag tttgtaagtg    540

atgcccttct cgttcctgac aagtgcaaat tcttacacca ggagaggatg gatgtttgcg    600
```

```
aaactcatct tcactggcac accgtcgcca aagagacatg cagtgagaag agtaccaact    660
tgcatgacta cggcatgttg ctgccctgcg gaattgacaa gttccgaggg gtagagtttg    720
tgtgttgccc actggctgaa gaaagtgaca atgtggattc tgctgatgcg gaggaggatg    780
actcggatgt ctggtggggc ggagcagaca cagactatgc agatgggagt gaagacaaag    840
tagtagaagt agcagaggag gaagaagtgg ctgaggtgga agaagaagaa gccgatgatg    900
acgaggacga tgaggatggt gatgaggtag aggaagaggc tgaggaaccc tacgaagaag    960
ccacagagag aaccaccagc attgccacca ccaccaccac caccacagag tctgtggaag   1020
aggtggttcg agaggtgtgc tctgaacaag ccgagacggg gccgtgccga gcaatgatct   1080
cccgctggta ctttgatgtg actgaaggga agtgtgcccc attcttttac ggcggatgtg   1140
gcggcaaccg gaacaacttt gacacagaag agtactgcat ggccgtgtgt ggcagcgcca   1200
tgtcccaaag tttactcaag actacccagg aacctcttgc ccgagatcct gttaaacttc   1260
ctacaacagc agccagtacc cctgatgccg ttgacaagta tctcgagaca cctggggatg   1320
agaatgaaca tgcccatttc cagaaagcca aagagaggct tgaggccaag caccgagaga   1380
gaatgtccca ggtcatgaga gaatgggaag aggcagaacg tcaagcaaag aacttgccta   1440
aagctgataa gaaggcagtt atccagcatt tccaggagaa agtggaatct ttggaacagg   1500
aagcagccaa cgagagacag cagctggtgg agacacacat ggccagagtg gaagccatgc   1560
tcaatgaccg ccgccgcctg gccctggaga actacatcac cgctctgcag gctgttcctc   1620
ctcggcctcg tcacgtgttc aatatgctaa agaagtatgt ccgcgcagaa cagaaggaca   1680
gacagcacac cctaaagcat ttcgagcatg tgcgcatggt ggatcccaag aaagccgctc   1740
agatccggtc ccaggttatg acacacctcc gtgtgattta tgagcgcatg aatcagtctc   1800
tctccctgct ctacaacgtg cctgcagtgg ccgaggagat tcaggatgaa gttgatgagc   1860
tgcttcagaa agagcaaaac tattcagatg acgtcttggc caacatgatt agtgaaccaa   1920
ggatcagtta cggaaacgat gctctcatgc catctttgac cgaaacgaaa accaccgtgg   1980
agctccttcc cgtgaatgga gagttcagcc tggacgatct ccagccgtgg cattcttttg   2040
gggctgactc tgtgccagcc aacacagaaa acgaaggttc tgggttgaca aatatcaaga   2100
cggaggagat ctctgaagtg aagatggatg cagaattccg acatgactca ggatatgaag   2160
ttcatcatca aaaattggtg ttctttgcag aagatgtggg ttcaaacaaa ggtgcaatca   2220
ttggactcat ggtgggcggt gttgtcatag cgacagtgat cgtcatcacc ttggtgatgc   2280
tgaagaagaa acagtacaca tccattcatc atggtgtggt ggaggttgac gccgctgtca   2340
ccccagagga gcgccacctg tccaagatgc agcagaacgg ctacgaaaat ccaacctaca   2400
agttctttga gcagatgcag aactagaccc ccgccacagc agcctctgaa gttggacagc   2460
aaaaccattg cttcactacc catcggtgtc catttataga ataatgtggg aagaaacaaa   2520
cccgttttat gatttactca ttatcgcctt ttgacagctg tgctgtaaca caagtagatg   2580
cctgaacttg aattaatcca cacatcagta atgtattcta tctctcttta cattttggtc   2640
tctatactac attattaatg ggttttgtgt actgtaaaga atttagctgt atcaaactag   2700
tgcatgaata gattctctcc tgattattta tcacatagcc ccttagccag ttgtatatta   2760
ttcttgtggt ttgtgaccca attaagtcct actttacata tgctttaaga atcgatgggg   2820
gatgcttcat gtgaacgtgg gagttcagct gcttctcttg cctaagtatt cctttcctga   2880
tcactatgca ttttaaagtt aaacattttt aagtatttca gatgctttag agagattttt   2940
```

```
tttccatgat cgctttctac actgtattac ataaataaat taaataaaat aaccccgggc   3000

aagacttttc tttgaaggat gactacagac attaaataat cgaagtaatt ttgggtgggg   3060

agaagaggca gattcaattt tctttaacca gtctgaagtt tcatttatga tacaaaagaa   3120

gatgaaaatg gaagtggcaa tataagggga tgaggaaggc atgcctggac aaacccttct   3180

tttaagatgt gtcttcaatt tgtataaaat ggtgttttca tgtaaataaa tacattcttg   3240

gaggagcacc attg                                                      3254


<210> SEQ ID NO 6
<211> LENGTH: 3467
<212> TYPE: DNA
<213> ORGANISM: Artificial sequence
<220> FEATURE:
<223> OTHER INFORMATION: Description of sequence: amyloid precursor
      protein coding sequence

<400> SEQUENCE: 6

cagcagcgca ctcggtgccc cgcgcagggt cgcgatgctg cccggtttgg cactgctcct     60

gctggccgcc tggacggctc gggcgctgga ggtacccact gatggtaatg ctggcctgct    120

ggctgaaccc cagattgcca tgttctgtgg cagactgaac atgcacatga atgtccagaa    180

tgggaagtgg gattcagatc catcagggac caaaacctgc attgatacca aggaaggcat    240

cctgcagtat tgccaagaag tctaccctga actgcagatc accaatgtgg tagaagccaa    300

ccaaccagtg accatccaga actggtgcaa gcggggccgc aagcagtgca agacccatcc    360

ccactttgtg attccctacc gctgcttagt tggtgagttt gtaagtgatg cccttctcgt    420

tcctgacaag tgcaaattct tacaccagga gaggatggat gtttgcgaaa ctcatcttca    480

ctggcacacc gtcgccaaag agacatgcag tgagaagagt accaacttgc atgactacgg    540

catgttgctg ccctgcggaa ttgacaagtt ccgaggggta gagtttgtgt gttgcccact    600

ggctgaagaa agtgacaatg tggattctgc tgatgcggag gaggatgact cggatgtctg    660

gtggggcgga gcagacacag actatgcaga tgggagtgaa gacaaagtag tagaagtagc    720

agaggaggaa gaagtggctg aggtggaaga agaagaagcc gatgatgacg aggacgatga    780

ggatggtgat gaggtagagg aagaggctga ggaaccctac gaagaagcca cagagagaac    840

caccagcatt gccaccacca ccaccaccac cacagagtct gtggaagagg tggttcgaga    900

ggtgtgctct gaacaagccg agacggggcc gtgccgagca atgatctccc gctggtactt    960

tgatgtgact gaagggaagt gtgccccatt cttttacggc ggatgtggcg gcaaccggaa   1020

caactttgac acagaagagt actgcatggc cgtgtgtggc agcgccatgt cccaaagttt   1080

actcaagact acccaggaac ctcttgcccg agatcctgtt aaacttccta caacagcagc   1140

cagtacccct gatgccgttg acaagtatct cgagacacct ggggatgaga atgaacatgc   1200

ccatttccag aaagccaaag agaggcttga ggccaagcac cgagagagaa tgtcccaggt   1260

catgagagaa tgggaagagg cagaacgtca agcaaagaac ttgcctaaag ctgataagaa   1320

ggcagttatc cagcatttcc aggagaaagt ggaatctttg gaacaggaag cagccaacga   1380

gagacagcag ctggtggaga cacacatggc cagagtggaa gccatgctca atgaccgccg   1440

ccgcctggcc ctggagaact acatcaccgc tctgcaggct gttcctcctc ggcctcgtca   1500

cgtgttcaat atgctaaaga agtatgtccg cgcagaacag aaggacagac agcacaccct   1560

aaagcatttc gagcatgtgc gcatggtgga tcccaagaaa gccgctcaga tccggtccca   1620

ggttatgaca cacctccgtg tgatttatga gcgcatgaat cagtctctct ccctgctcta   1680
```

```
caacgtgcct gcagtggccg aggagattca ggatgaagtt gatgagctgc ttcagaaaga   1740

gcaaaactat tcagatgacg tcttggccaa catgattagt gaaccaagga tcagttacgg   1800

aaacgatgct ctcatgccat ctttgaccga aacgaaaacc accgtggagc tccttcccgt   1860

gaatggagag ttcagcctgg acgatctcca gccgtggcat tcttttgggg ctgactctgt   1920

gccagccaac acagaaaacg aagttgagcc tgttgatgcc cgccctgctg ccgaccgagg   1980

actgaccact cgaccaggtt ctgggttgac aaatatcaag acggaggaga tctctgaagt   2040

gaagatggat gcagaattcc gacatgactc aggatatgaa gttcatcatc aaaaattggt   2100

gttctttgca gaagatgtgg gttcaaacaa aggtgcaatc attggactca tggtgggcgg   2160

tgttgtcata gcgacagtga tcgtcatcac cttggtgatg ctgaagaaga aacagtacac   2220

atccattcat catggtgtgg tggaggttga cgccgctgtc accccagagg agcgccacct   2280

gtccaagatg cagcagaacg gctacgaaaa tccaacctac aagttctttg agcagatgca   2340

gaactagacc cccgccacag cagcctctga agttggacag caaaaccatt gcttcactac   2400

ccatcggtgt ccatttatag aataatgtgg gaagaaacaa acccgtttta tgatttactc   2460

attatcgcct tttgacagct gtgctgtaac acaagtagat gcctgaactt gaattaatcc   2520

acacatcagt aatgtattct atctctcttt acattttggt ctctatacta cattattaat   2580

gggttttgtg tactgtaaag aatttagctg tatcaaacta gtgcatgaat agattctctc   2640

ctgattattt atcacatagc cccttagcca gttgtatatt attcttgtgg tttgtgaccc   2700

aattaagtcc tactttacat atgctttaag aatcgatggg ggatgcttca tgtgaacgtg   2760

ggagttcagc tgcttctctt gcctaagtat tcctttcctg atcactatgc attttaaagt   2820

taaacatttt taagtatttc agatgcttta gagagatttt ttttccatga ctgcatttta   2880

ctgtacagat tgctgcttct gctatatttg tgatatagga attaagagga tacacacgtt   2940

tgtttcttcg tgcctgtttt atgtgcacac attaggcatt gagacttcaa gcttttcttt   3000

ttttgtccac gtatctttgg gtctttgata aagaaaagaa tccctgttca ttgtaagcac   3060

ttttacgggg cgggtgggga ggggtgctct gctggtcttc aattaccaag aattctccaa   3120

aacaattttc tgcaggatga ttgtacagaa tcattgctta tgacatgatc gctttctaca   3180

ctgtattaca taaataaatt aaataaaata accccgggca agacttttct ttgaaggatg   3240

actacagaca ttaaataatc gaagtaattt tgggtgggga gaagaggcag attcaatttt   3300

ctttaaccag tctgaagttt catttatgat acaaaagaag atgaaaatgg aagtggcaat   3360

ataaggggat gaggaaggca tgcctggaca aacccttctt ttaagatgtg tcttcaattt   3420

gtataaaatg gtgttttcat gtaaataaat acattcttgg aggagca                3467


<210> SEQ ID NO 7
<211> LENGTH: 3355
<212> TYPE: DNA
<213> ORGANISM: Artificial sequence
<220> FEATURE:
<223> OTHER INFORMATION: Description of sequence: amyloid precursor
      protein coding sequence

<400> SEQUENCE: 7

agtttcctcg gcagcggtag gcgagagcac gcggaggagc gtgcgcgggg gccccgggag     60

acggcggcgg tggcggcgcg ggcagagcaa ggacgcggcg gatcccactc gcacagcagc    120

gcactcggtg ccccgcgcag ggtcgcgatg ctgcccggtt tggcactgct cctgctggcc    180

gcctggacgg ctcgggcgct ggaggtaccc actgatggta atgctggcct gctggctgaa    240
```

-continued

```
ccccagattg ccatgttctg tggcagactg aacatgcaca tgaatgtcca gaatgggaag    300
tgggattcag atccatcagg gaccaaaacc tgcattgata ccaaggaagg catcctgcag    360
tattgccaag aagtctaccc tgaactgcag atcaccaatg tggtagaagc caaccaacca    420
gtgaccatcc agaactggtg caagcggggc cgcaagcagt gcaagaccca tccccacttt    480
gtgattccct accgctgctt agttggtgag tttgtaagtg atgcccttct cgttcctgac    540
aagtgcaaat tcttacacca ggagaggatg gatgtttgcg aaactcatct tcactggcac    600
accgtcgcca aagagacatg cagtgagaag agtaccaact tgcatgacta cggcatgttg    660
ctgccctgcg gaattgacaa gttccgaggg gtagagtttg tgtgttgccc actggctgaa    720
gaaagtgaca atgtggattc tgctgatgcg gaggaggatg actcggatgt ctggtggggc    780
ggagcagaca cagactatgc agatgggagt gaagacaaag tagtagaagt agcagaggag    840
gaagaagtgg ctgaggtgga agaagaagaa gccgatgatg acgaggacga tgaggatggt    900
gatgaggtag aggaagaggc tgaggaaccc tacgaagaag ccacagagag aaccaccagc    960
attgccacca ccaccaccac caccacagag tctgtggaag aggtggttcg agttcctaca   1020
acagcagcca gtacccctga tgccgttgac aagtatctcg agacacctgg ggatgagaat   1080
gaacatgccc atttccagaa agccaaagag aggcttgagg ccaagcaccg agagagaatg   1140
tcccaggtca tgagagaatg ggaagaggca gaacgtcaag caaagaactt gcctaaagct   1200
gataagaagg cagttatcca gcatttccag gagaaagtgg aatctttgga acaggaagca   1260
gccaacgaga gacagcagct ggtggagaca cacatggcca gagtggaagc catgctcaat   1320
gaccgccgcc gcctggccct ggagaactac atcaccgctc tgcaggctgt tcctcctcgg   1380
cctcgtcacg tgttcaatat gctaaagaag tatgtccgcg cagaacagaa ggacagacag   1440
cacaccctaa agcatttcga gcatgtgcgc atggtggatc ccaagaaagc cgctcagatc   1500
cggtcccagg ttatgacaca cctccgtgtg atttatgagc gcatgaatca gtctctctcc   1560
ctgctctaca acgtgcctgc agtggccgag gagattcagg atgaagttga tgagctgctt   1620
cagaaagagc aaaactattc agatgacgtc ttggccaaca tgattagtga accaaggatc   1680
agttacggaa acgatgctct catgccatct ttgaccgaaa cgaaaaccac cgtggagctc   1740
cttcccgtga atggagagtt cagcctggac gatctccagc cgtggcattc ttttggggct   1800
gactctgtgc cagccaacac agaaaacgaa gttgagcctg ttgatgcccg ccctgctgcc   1860
gaccgaggac tgaccactcg accaggttct gggttgacaa atatcaagac ggaggagatc   1920
tctgaagtga agatggatgc agaattccga catgactcag gatatgaagt tcatcatcaa   1980
aaattggtgt tctttgcaga agatgtgggt tcaaacaaag gtgcaatcat tggactcatg   2040
gtgggcggtg ttgtcatagc gacagtgatc gtcatcacct tggtgatgct gaagaagaaa   2100
cagtacacat ccattcatca tggtgtggtg gaggttgacg ccgctgtcac cccagaggag   2160
cgccacctgt ccaagatgca gcagaacggc tacgaaaatc caacctacaa gttctttgag   2220
cagatgcaga actagacccc cgccacagca gcctctgaag ttggacagca aaaccattgc   2280
ttcactaccc atcggtgtcc atttatagaa taatgtggga agaaacaaac ccgttttatg   2340
atttactcat tatcgccttt tgacagctgt gctgtaacac aagtagatgc ctgaacttga   2400
attaatccac acatcagtaa tgtattctat ctctctttac attttggtct ctatactaca   2460
ttattaatgg gttttgtgta ctgtaaagaa tttagctgta tcaaactagt gcatgaatag   2520
attctctcct gattatttat cacatagccc cttagccagt tgtatattat tcttgtggtt   2580
tgtgacccaa ttaagtccta ctttacatat gctttaagaa tcgatggggg atgcttcatg   2640
```

```
tgaacgtggg agttcagctg cttctcttgc ctaagtattc ctttcctgat cactatgcat   2700

tttaaagtta aacattttta agtatttcag atgctttaga gagatttttt ttccatgact   2760

gcattttact gtacagattg ctgcttctgc tatatttgtg atataggaat taagaggata   2820

cacacgtttg tttcttcgtg cctgttttat gtgcacacat taggcattga gacttcaagc   2880

ttttcttttt ttgtccacgt atctttgggt ctttgataaa gaaaagaatc cctgttcatt   2940

gtaagcactt ttacggggcg ggtggggagg ggtgctctgc tggtcttcaa ttaccaagaa   3000

ttctccaaaa caattttctg caggatgatt gtacagaatc attgcttatg acatgatcgc   3060

tttctacact gtattacata aataaattaa ataaaataac cccgggcaag acttttcttt   3120

gaaggatgac tacagacatt aaataatcga agtaatttg ggtggggaga agaggcagat   3180

tcaattttct ttaaccagtc tgaagtttca tttatgatac aaaagaagat gaaaatggaa   3240

gtggcaatat aaggggatga ggaaggcatg cctggacaaa cccttctttt aagatgtgtc   3300

ttcaatttgt ataaaatggt gttttcatgt aaataaatac attcttggag gagca        3355
```

<210> SEQ ID NO 8
<211> LENGTH: 3167
<212> TYPE: DNA
<213> ORGANISM: Artificial sequence
<220> FEATURE:
<223> OTHER INFORMATION: Description of sequence: amyloid precursor protein coding sequence

<400> SEQUENCE: 8

```
gcgagagcac gcggaggagc gtgcgcgggg gccccgggag acggcggcgg tggcggcgcg     60

ggcagagcaa ggacgcggcg gatcccactc gcacagcagc gcactcggtg ccccgcgcag    120

ggtcgcgatg ctgcccggtt tggcactgct cctgctggcc gcctggacgg ctcgggcgct    180

ggaggtctac cctgaactgc agatcaccaa tgtggtagaa gccaaccaac cagtgaccat    240

ccagaactgg tgcaagcggg gccgcaagca gtgcaagacc catccccact ttgtgattcc    300

ctaccgctgc ttagttggtg agtttgtaag tgatgccctt ctcgttcctg acaagtgcaa    360

attcttacac caggagagga tggatgtttg cgaaactcat cttcactggc acaccgtcgc    420

caaagagaca tgcagtgaga agagtaccaa cttgcatgac tacggcatgt tgctgccctg    480

cggaattgac aagttccgag ggtagagtt tgtgtgttgc ccactggctg aagaaagtga    540

caatgtggat tctgctgatg cggaggagga tgactcggat gtctggtggg gcggagcaga    600

cacagactat gcagatggga gtgaagacaa agtagtagaa gtagcagagg aggaagaagt    660

ggctgaggtg gaagaagaag aagccgatga tgacgaggac gatgaggatg gtgatgaggt    720

agaggaagag gctgaggaac cctacgaaga agccacagag agaaccacca gcattgccac    780

caccaccacc accaccacag agtctgtgga agaggtggtt cgagttccta caacagcagc    840

cagtacccct gatgccgttg acaagtatct cgagacacct ggggatgaga atgaacatgc    900

ccatttccag aaagccaaag agaggcttga ggccaagcac cgagagagaa tgtcccaggt    960

catgagagaa tgggaagagg cagaacgtca agcaaagaac ttgcctaaag ctgataagaa   1020

ggcagttatc cagcatttcc aggagaaagt ggaatctttg gaacaggaag cagccaacga   1080

gagacagcag ctggtggaga cacacatggc cagagtggaa gccatgctca atgaccgccg   1140

ccgcctggcc ctggagaact acatcaccgc tctgcaggct gttcctcctc ggcctcgtca   1200

cgtgttcaat atgctaaaga agtatgtccg cgcagaacag aaggacagac agcacaccct   1260

aaagcatttc gagcatgtgc gcatggtgga tcccaagaaa gccgctcaga tccggtccca   1320
```

ggttatgaca cacctccgtg tgatttatga gcgcatgaat cagtctctct ccctgctcta 1380
caacgtgcct gcagtggccg aggagattca ggatgaagtt gatgagctgc ttcagaaaga 1440
gcaaaactat tcagatgacg tcttggccaa catgattagt gaaccaagga tcagttacgg 1500
aaacgatgct ctcatgccat ctttgaccga aacgaaaacc accgtggagc tccttcccgt 1560
gaatggagag ttcagcctgg acgatctcca gccgtggcat tcttttgggg ctgactctgt 1620
gccagccaac acagaaaacg aagttgagcc tgttgatgcc cgccctgctg ccgaccgagg 1680
actgaccact cgaccaggtt ctgggttgac aaatatcaag acggaggaga tctctgaagt 1740
gaagatggat gcagaattcc gacatgactc aggatatgaa gttcatcatc aaaaattggt 1800
gttctttgca gaagatgtgg gttcaaacaa aggtgcaatc attggactca tggtgggcgg 1860
tgttgtcata gcgacagtga tcgtcatcac cttggtgatg ctgaagaaga aacagtacac 1920
atccattcat catggtgtgg tggaggttga cgccgctgtc accccagagg agcgccacct 1980
gtccaagatg cagcagaacg gctacgaaaa tccaacctac aagttctttg agcagatgca 2040
gaactagacc cccgccacag cagcctctga agttggacag caaaaccatt gcttcactac 2100
ccatcggtgt ccatttatag aataatgtgg gaagaaacaa acccgtttta tgatttactc 2160
attatcgcct tttgacagct gtgctgtaac acaagtagat gcctgaactt gaattaatcc 2220
acacatcagt aatgtattct atctctcttt acattttggt ctctatacta cattattaat 2280
gggttttgtg tactgtaaag aatttagctg tatcaaacta gtgcatgaat agattctctc 2340
ctgattattt atcacatagc cccttagcca gttgtatatt attcttgtgg tttgtgaccc 2400
aattaagtcc tactttacat atgctttaag aatcgatggg ggatgcttca tgtgaacgtg 2460
ggagttcagc tgcttctctt gcctaagtat tcctttcctg atcactatgc attttaaagt 2520
taaacatttt taagtatttc agatgcttta gagagatttt ttttccatga ctgcatttta 2580
ctgtacagat tgctgcttct gctatatttg tgatatagga attaagagga tacacacgtt 2640
tgtttcttcg tgcctgtttt atgtgcacac attaggcatt gagacttcaa gcttttcttt 2700
ttttgtccac gtatctttgg gtctttgata aagaaaagaa tccctgttca ttgtaagcac 2760
ttttacgggg cgggtgggga ggggtgctct gctggtcttc aattaccaag aattctccaa 2820
aacaattttc tgcaggatga ttgtacagaa tcattgctta tgacatgatc gctttctaca 2880
ctgtattaca taaataaatt aaataaaata accccgggca agacttttct ttgaaggatg 2940
actacagaca ttaaataatc gaagtaattt tgggtgggga gaagaggcag attcaatttt 3000
ctttaaccag tctgaagttt catttatgat acaaaagaag atgaaaatgg aagtggcaat 3060
ataaggggat gaggaaggca tgcctggaca aacccttctt ttaagatgtg tcttcaattt 3120
gtataaaatg gtgttttcat gtaaataaat acattcttgg aggagca 3167

<210> SEQ ID NO 9
<211> LENGTH: 3543
<212> TYPE: DNA
<213> ORGANISM: Artificial sequence
<220> FEATURE:
<223> OTHER INFORMATION: Description of sequence: amyloid precursor protein coding sequence

<400> SEQUENCE: 9
cgccgcgctc gggctccgtc agtttcctcg gcagcggtag gcgagagcac gcggaggagc 60
gtgcgcgggg gccccgggag acggcggcgg tggcggcgcg ggcagagcaa ggacgcggcg 120
gatcccactc gcacagcagc gcactcggtg ccccgcgcag ggtcgcgatg ctgcccggtt 180

```
tggcactgct cctgctggcc gcctggacgg ctcgggcgct ggaggtaccc actgatggta    240
atgctggcct gctggctgaa ccccagattg ccatgttctg tggcagactg aacatgcaca    300
tgaatgtcca gaatgggaag tgggattcag atccatcagg gaccaaaacc tgcattgata    360
ccaaggaagg catcctgcag tattgccaag aagtctaccc tgaactgcag atcaccaatg    420
tggtagaagc caaccaacca gtgaccatcc agaactggtg caagcggggc cgcaagcagt    480
gcaagaccca tccccacttt gtgattccct accgctgctt agttggtgag tttgtaagtg    540
atgcccttct cgttcctgac aagtgcaaat tcttacacca ggagaggatg gatgtttgcg    600
aaactcatct tcactggcac accgtcgcca aagagacatg cagtgagaag agtaccaact    660
tgcatgacta cggcatgttg ctgccctgcg gaattgacaa gttccgaggg gtagagtttg    720
tgtgttgccc actggctgaa gaaagtgaca atgtggattc tgctgatgcg gaggaggatg    780
actcggatgt ctggtggggc ggagcagaca cagactatgc agatgggagt gaagacaaag    840
tagtagaagt agcagaggag gaagaagtgg ctgaggtgga agaagaagaa gccgatgatg    900
acgaggacga tgaggatggt gatgaggtag aggaagaggc tgaggaaccc tacgaagaag    960
ccacagagag aaccaccagc attgccacca ccaccaccac caccacagag tctgtggaag   1020
aggtggttcg agaggtgtgc tctgaacaag ccgagacggg gccgtgccga gcaatgatct   1080
cccgctggta ctttgatgtg actgaaggga agtgtgcccc attcttttac ggcggatgtg   1140
gcggcaaccg gaacaacttt gacacagaag agtactgcat ggccgtgtgt ggcagcgcca   1200
ttcctacaac agcagccagt acccctgatg ccgttgacaa gtatctcgag acacctgggg   1260
atgagaatga acatgcccat ttccagaaag ccaaagagag gcttgaggcc aagcaccgag   1320
agagaatgtc ccaggtcatg agagaatggg aagaggcaga acgtcaagca aagaacttgc   1380
ctaaagctga taagaaggca gttatccagc atttccagga gaaagtggaa tctttggaac   1440
aggaagcagc caacgagaga cagcagctgg tggagacaca catggccaga gtggaagcca   1500
tgctcaatga ccgccgccgc ctggccctgg agaactacat caccgctctg caggctgttc   1560
ctcctcggcc tcgtcacgtg ttcaatatgc taaagaagta tgtccgcgca gaacagaagg   1620
acagacagca caccctaaag catttcgagc atgtgcgcat ggtggatccc aagaaagccg   1680
ctcagatccg gtcccaggtt atgacacacc tccgtgtgat ttatgagcgc atgaatcagt   1740
ctctctccct gctctacaac gtgcctgcag tggccgagga gattcaggat gaagttgatg   1800
agctgcttca gaaagagcaa aactattcag atgacgtctt ggccaacatg attagtgaac   1860
caaggatcag ttacggaaac gatgctctca tgccatcttt gaccgaaacg aaaaccaccg   1920
tggagctcct tcccgtgaat ggagagttca gcctggacga tctccagccg tggcattctt   1980
ttggggctga ctctgtgcca gccaacacag aaaacgaagt tgagcctgtt gatgcccgcc   2040
ctgctgccga ccgaggactg accactcgac caggttctgg gttgacaaat atcaagacgg   2100
aggagatctc tgaagtgaag atggatgcag aattccgaca tgactcagga tatgaagttc   2160
atcatcaaaa attggtgttc tttgcagaag atgtgggttc aaacaaaggt gcaatcattg   2220
gactcatggt gggcggtgtt gtcatagcga cagtgatcgt catcaccttg gtgatgctga   2280
agaagaaaca gtacacatcc attcatcatg gtgtggtgga ggttgacgcc gctgtcaccc   2340
cagaggagcg ccacctgtcc aagatgcagc agaacggcta cgaaaatcca acctacaagt   2400
tctttgagca gatgcagaac tagacccccg ccacagcagc ctctgaagtt ggacagcaaa   2460
accattgctt cactacccat cggtgtccat ttatagaata atgtgggaag aaacaaaccc   2520
```

```
gttttatgat ttactcatta tcgccttttg acagctgtgc tgtaacacaa gtagatgcct   2580

gaacttgaat taatccacac atcagtaatg tattctatct ctctttacat tttggtctct   2640

atactacatt attaatgggt tttgtgtact gtaaagaatt tagctgtatc aaactagtgc   2700

atgaatagat tctctcctga ttatttatca catagcccct tagccagttg tatattattc   2760

ttgtggtttg tgacccaatt aagtcctact ttacatatgc tttaagaatc gatgggggat   2820

gcttcatgtg aacgtgggag ttcagctgct tctcttgcct aagtattcct ttcctgatca   2880

ctatgcattt taaagttaaa catttttaag tatttcagat gctttagaga gatttttttt   2940

ccatgactgc attttactgt acagattgct gcttctgcta tatttgtgat ataggaatta   3000

agaggataca cacgtttgtt tcttcgtgcc tgttttatgt gcacacatta ggcattgaga   3060

cttcaagctt ttcttttttt gtccacgtat ctttgggtct ttgataaaga aaagaatccc   3120

tgttcattgt aagcactttt acggggcggg tggggagggg tgctctgctg gtcttcaatt   3180

accaagaatt ctccaaaaca attttctgca ggatgattgt acagaatcat tgcttatgac   3240

atgatcgctt tctacactgt attacataaa taaattaaat aaaataaccc cgggcaagac   3300

ttttctttga aggatgacta cagacattaa ataatcgaag taattttggg tggggagaag   3360

aggcagattc aatttttcttt aaccagtctg aagtttcatt tatgatacaa aagaagatga   3420

aaatggaagt ggcaatataa ggggatgagg aaggcatgcc tggacaaacc cttcttttaa   3480

gatgtgtctt caatttgtat aaaatggtgt tttcatgtaa ataaatacat tcttggagga   3540

gca                                                                3543
```

<210> SEQ ID NO 10
<211> LENGTH: 690
<212> TYPE: DNA
<213> ORGANISM: Artificial sequence
<220> FEATURE:
<223> OTHER INFORMATION: Description of sequence: amyloid precursor protein coding sequence

<400> SEQUENCE: 10

```
ctttatcact ttactatgca atttttatga ctatgcttaa ggagagtaaa tttttcgaag     60

ttattgaggc aatggagagt ctttggaatg aggataatta ggcctgagga cacagaggaa    120

tcatgaggaa gaattctcca gtttcattcc tttttctggg tacagtttgt ttctccttct    180

aagtaagttc ctagatatag aatgaattgg aaaaaatgaa acgtgaggtt tgctacgtct    240

ataacagtat cacatttcat tttttaaaac tgccaatgct ttcagtgagg accagaaagt    300

acagtgagaa aaaaaaattc ctcaaatatt agttttcatg ctcttgcacg catttttata    360

aaggcaaaag tcattctggt gcctgtatac aatctaaagg cataatctcc tggagccttc    420

agtgctggtt ttggggtttt ctggagatca atccacagtg tcccattttt tctgctggag    480

ctctgaaccc actaagagag agcaagaaga gatgtaaacc tctcctttgc ttctgataaa    540

gccaagccct tactagtcca catgatgctt tctctgggga gtgagtcaca tacaggagac    600

atggcttgtc cagctgcgtg ctggactgaa tttcagctcc aacctgaacc ttccaacagg    660

acaagggagg gaggagaatg ggccgtagca                                     690
```

<210> SEQ ID NO 11
<211> LENGTH: 905
<212> TYPE: DNA
<213> ORGANISM: Artificial sequence
<220> FEATURE:
<223> OTHER INFORMATION: Description of sequence: amyloid precursor protein coding sequence

<400> SEQUENCE: 11

```
gtgtgtaccc ctaaacccag cttattattt ttttgacttt ttgtagaaac agggtctccc     60
catgttgccc aggctggtct taaactcctg ggctcaaatg atcctcctgc ctcagcctcc    120
catagggcta ggattacagg tgtgagccac catgcctggc cttttatact gtttattccc    180
tttagataca gttaatggac attaataagc agtttatgcc aatccctttt catagctaat    240
aagaagtctt atcttggata aataaaacct agccactaat gctgccacac ccaaataaac    300
tctctatgca tctgaacttc ttgaggttaa taatgcttca ttgtaatatt ttataaaatc    360
accactttgg aagtgaacac cactagaaat tcacatggcc agtttataga tggggactgg    420
gggaagcagg gaggatctct gcaatccagt agttaggctc tgccagaatg tatttagagt    480
tgtctctaaa tacattctga gtctctgctt cattttttt ttcaatgaaa atgacaatgt    540
ctgtcatccc atgttcaaga caaatataac aagtttctaa gaatccttat atttttgtta    600
ttgcatataa gcatgagttt taaaaacctc tgaatgttta aaggatcacc tgggggaata    660
agaaaaatgc agatctctgt aggtctgagg tagagcccaa gaatctgtat ttttaactag    720
aattcctcta aattactgtg cttcacttgg ccccaattac acattaggag acaatgattt    780
caggatgaca atcagccttt tccatccaag gacttaaagc agctaaaccg aagacaccga    840
caaataccag atacttttct cagtctactg gctgatggca caaaagtgca gaagtcacgt    900
agggc                                                                905
```

<210> SEQ ID NO 12
<211> LENGTH: 1320
<212> TYPE: DNA
<213> ORGANISM: Artificial sequence
<220> FEATURE:
<223> OTHER INFORMATION: Description of sequence: amyloid precursor protein coding sequence

<400> SEQUENCE: 12

```
catgaggaac tccttgggcc ttgaccattt ttagcacttt cacagtttct gattttgatc     60
aagccactta atcacccagg attctgaatc tgaaaaccag gagggtttaa ttccactttc    120
atgttccctt gaggagctgt tggcagcagg atgaaggcag gtccatacag aacatgggaa    180
ggaagccagg aagccagctt ttcctttcac atcaaagaga tctagaaagc aaaacctgtc    240
tcacatttgc atacaatatt agacttacat atggatgcca tgtctgtcaa aagacaggct    300
aattagggca ttagtttctt taatggttgc gatttagtaa ttcacaaata gtcccactta    360
atttttcatc ctatacctaa aggatctact tcacacttga agtttaagaa ggcttctccc    420
ttaagataga aagaaggcat tcaagtatca aaatactggt ttcctgccaa aaaataaggg    480
atgagaaaaa gcagacactt agcttatcaa tcaaaatgct ggcagggaaa gactactgga    540
ttaccaagtt cattccccta gcctgcactg attcctcttt ttctctaaag tttcttattt    600
tttcagtttt tctcatgata ctgacattgc caaccagcag tctggaaact gttcaggttg    660
attcttagca gaaaatcgag gggctctcct gttactgtta atatccttaa aacacttaaa    720
tttggttagt ttgcttcaag cattctcagt atattacaaa aaaaaaaagt actcaagaat    780
ttctagactt tattttgact gacatcagct accctaatga acaggagggg acaacagcaa    840
ggtatattag gagcatctcc ttcctttta atcagaatta tataggaatt aagaactcta    900
aggccacagt agagtatagt atcttggaag aagaaagcgg agaatgtctg acattttcac    960
tgatcgttta ggctgatggc ttaaaccatt tccacccaag tttcttacaa gttagcattt   1020
```

```
ccagccaaca ttacctactg caatttctct ataatcttaa gggtattgag cccccaaatg   1080

agagagagaa aagagatgta aactaaacag gagtcagaga aggggaaact gagtctgttg   1140

cacatcattt accctttaac atgattttaa aggtaataat gcttataaaa atattagtag   1200

tagtaaggga tatcaggtga caagcagaag tgcccctctc cacagatatg ccagtgtatc   1260

tgtagaaata cggtgctaaa attagaaaag actgaacatt ttaatttatt aggtagaccc   1320


<210> SEQ ID NO 13
<211> LENGTH: 3552
<212> TYPE: DNA
<213> ORGANISM: Artificial sequence
<220> FEATURE:
<223> OTHER INFORMATION: Description of sequence: amyloid precursor
      protein coding sequence

<400> SEQUENCE: 13

cgccgcgctc gggctccgtc agtttcctcg gcagcggtag gcgagagcac gcggaggagc     60

gtgcgcgggg gccccgggag acggcggcgg tggcggcgcg ggcagagcaa ggacgcggcg    120

gatcccactc gcacagcagc gcactcggtg ccccgcgcag ggtcgcgatg ctgcccggtt    180

tggcactgct cctgctggcc gcctggacgg ctcgggcgct ggaggtaccc actgatggta    240

atgctggcct gctggctgaa ccccagattg ccatgttctg tggcagactg aacatgcaca    300

tgaatgtcca gaatgggaag tgggattcag atccatcagg gaccaaaacc tgcattgata    360

ccaaggaagg catcctgcag tattgccaag aagtctaccc tgaactgcag atcaccaatg    420

tggtagaagc caaccaacca gtgaccatcc agaactggtg caagcggggc cgcaagcagt    480

gcaagaccca tccccacttt gtgattccct accgctgctt agttggtgag tttgtaagtg    540

atgcccttct cgttcctgac aagtgcaaat tcttacacca ggagaggatg gatgtttgcg    600

aaactcatct tcactggcac accgtcgcca aagagacatg cagtgagaag agtaccaact    660

tgcatgacta cggcatgttg ctgccctgcg gaattgacaa gttccgaggg gtagagtttg    720

tgtgttgccc actggctgaa gaaagtgaca atgtggattc tgctgatgcg gaggaggatg    780

actcggatgt ctggtggggc ggagcagaca cagactatgc agatgggagt gaagacaaag    840

tagtagaagt agcagaggag gaagaagtgg ctgaggtgga agaagaagaa gccgatgatg    900

acgaggacga tgaggatggt gatgaggtag aggaagaggc tgaggaaccc tacgaagaag    960

ccacagagag aaccaccagc attgccacca ccaccaccac caccacagag tctgtggaag   1020

aggtggttcg agaggtgtgc tctgaacaag ccgagacggg gccgtgccga gcaatgatct   1080

cccgctggta ctttgatgtg actgaaggga agtgtgcccc attcttttac ggcggatgtg   1140

gcggcaaccg gaacaacttt gacacagaag agtactgcat ggccgtgtgt ggcagcgcca   1200

tgtcccaaag tttactcaag actacccagg aacctcttgc ccgagatcct gttaaacttc   1260

ctacaacagc agccagtacc cctgatgccg ttgacaagta tctcgagaca cctggggatg   1320

agaatgaaca tgcccatttc cagaaagcca aagagaggct tgaggccaag caccgagaga   1380

gaatgtccca ggtcatgaga gaatgggaag aggcagaacg tcaagcaaag aacttgccta   1440

aagctgataa gaaggcagtt atccagcatt tccaggagaa agtggaatct ttggaacagg   1500

aagcagccaa cgagagacag cagctggtgg agacacacat ggccagagtg gaagccatgc   1560

tcaatgaccg ccgccgcctg gccctggaga actacatcac cgctctgcag gctgttcctc   1620

ctcggcctcg tcacgtgttc aatatgctaa agaagtatgt ccgcgcagaa cagaaggaca   1680

gacagcacac cctaaagcat ttcgagcatg tgcgcatggt ggatcccaag aaagccgctc   1740
```

agatccggtc ccaggttatg acacacctcc gtgtgattta tgagcgcatg aatcagtctc 1800
tctccctgct ctacaacgtg cctgcagtgg ccgaggagat tcaggatgaa gttgatgagc 1860
tgcttcagaa agagcaaaac tattcagatg acgtcttggc caacatgatt agtgaaccaa 1920
ggatcagtta cggaaacgat gctctcatgc catctttgac cgaaacgaaa accaccgtgg 1980
agctccttcc cgtgaatgga gagttcagcc tggacgatct ccagccgtgg cattcttttg 2040
gggctgactc tgtgccagcc aacacagaaa acgaaggttc tgggttgaca aatatcaaga 2100
cggaggagat ctctgaagtg aagatggatg cagaattccg acatgactca ggatatgaag 2160
ttcatcatca aaaattggtg ttctttgcag aagatgtggg ttcaaacaaa ggtgcaatca 2220
ttggactcat ggtgggcggt gttgtcatag cgacagtgat cgtcatcacc ttggtgatgc 2280
tgaagaagaa acagtacaca tccattcatc atggtgtggt ggaggttgac gccgctgtca 2340
ccccagagga gcgccacctg tccaagatgc agcagaacgg ctacgaaaat ccaacctaca 2400
agttctttga gcagatgcag aactagaccc ccgccacagc agcctctgaa gttggacagc 2460
aaaaccattg cttcactacc catcggtgtc catttataga ataatgtggg aagaaacaaa 2520
cccgttttat gatttactca ttatcgcctt ttgacagctg tgctgtaaca caagtagatg 2580
cctgaacttg aattaatcca cacatcagta atgtattcta tctctcttta cattttggtc 2640
tctatactac attattaatg ggttttgtgt actgtaaaga atttagctgt atcaaactag 2700
tgcatgaata gattctctcc tgattattta tcacatagcc ccttagccag ttgtatatta 2760
ttcttgtggt ttgtgaccca attaagtcct actttacata tgctttaaga atcgatgggg 2820
gatgcttcat gtgaacgtgg gagttcagct gcttctcttg cctaagtatt cctttcctga 2880
tcactatgca ttttaaagtt aaacattttt aagtatttca gatgctttag agagattttt 2940
tttccatgac tgcattttac tgtacagatt gctgcttctg ctatatttgt gatataggaa 3000
ttaagaggat acacacgttt gtttcttcgt gcctgtttta tgtgcacaca ttaggcattg 3060
agacttcaag cttttctttt tttgtccacg tatctttggg tctttgataa agaaaagaat 3120
ccctgttcat tgtaagcact tttacggggc gggtggggag gggtgctctg ctggtcttca 3180
attaccaaga attctccaaa acaattttct gcaggatgat tgtacagaat cattgcttat 3240
gacatgatcg ctttctacac tgtattacat aaataaatta aataaaataa ccccgggcaa 3300
gacttttctt tgaaggatga ctacagacat taaataatcg aagtaatttt gggtggggag 3360
aagaggcaga ttcaattttc tttaaccagt ctgaagtttc atttatgata caaaagaaga 3420
tgaaaatgga agtggcaata taaggggatg aggaaggcat gcctggacaa acccttcttt 3480
taagatgtgt cttcaatttg tataaaatgg tgttttcatg taaataaata cattcttgga 3540
ggagcaccat tg 3552

<210> SEQ ID NO 14
<211> LENGTH: 2366
<212> TYPE: DNA
<213> ORGANISM: Artificial sequence
<220> FEATURE:
<223> OTHER INFORMATION: Description of sequence: amyloid precursor
protein coding sequence

<400> SEQUENCE: 14
gatcccactc gcacagcagc gcactcggtg ccccgcgcag ggtcgcgatg ctgcccggtt 60
tggcactgct cctgctggcc gcctggacgg ctcgggcgct ggaggtaccc actgatggta 120
atgctggcct gctggctgaa ccccagattg ccatgttctg tggcagactg aacatgcaca 180

```
tgaatgtcca gaatgggaag tgggattcag atccatcagg gaccaaaacc tgcattgata    240
ccaaggaagg catcctgcag tattgccaag aagtctaccc tgaactgcag atcaccaatg    300
tggtagaagc caaccaacca gtgaccatcc agaactggtg caagcggggc cgcaagcagt    360
gcaagaccca tccccacttt gtgattccct accgctgctt agttggtgag tttgtaagtg    420
atgcccttct cgttcctgac aagtgcaaat tcttacacca ggagaggatg gatgtttgcg    480
aaactcatct tcactggcac accgtcgcca aagagacatg cagtgagaag agtaccaact    540
tgcatgacta cggcatgttg ctgccctgcg gaattgacaa gttccgaggg gtagagtttg    600
tgtgttgccc actggctgaa gaaagtgaca atgtggattc tgctgatgcg gaggaggatg    660
actcggatgt ctggtggggc ggagcagaca cagactatgc agatgggagt gaagacaaag    720
tagtagaagt agcagaggag gaagaagtgg ctgaggtgga agaagaagaa gccgatgatg    780
acgaggacga tgaggatggt gatgaggtag aggaagaggc tgaggaaccc tacgaagaag    840
ccacagagag aaccaccagc attgccacca ccaccaccac caccacagag tctgtggaag    900
aggtggttcg agaggtgtgc tctgaacaag ccgagacggg gccgtgccga gcaatgatct    960
cccgctggta ctttgatgtg actgaaggga agtgtgcccc attcttttac ggcggatgtg   1020
gcggcaaccg gaacaacttt gacacagaag agtactgcat ggccgtgtgt ggcagcgcca   1080
tgtcccaaag tttactcaag actacccagg aacctcttgc ccgagatcct gttaaacttc   1140
ctacaacagc agccagtacc cctgatgccg ttgacaagta tctcgagaca cctggggatg   1200
agaatgaaca tgcccatttc cagaaagcca aagagaggct tgaggccaag caccgagaga   1260
gaatgtccca ggtcatgaga gaatgggaag aggcagaacg tcaagcaaag aacttgccta   1320
aagctgataa gaaggcagtt atccagcatt tccaggagaa agtggaatct ttggaacagg   1380
aagcagccaa cgagagacag cagctggtgg agacacacat ggccagagtg gaagccatgc   1440
tcaatgaccg ccgccgcctg gccctggaga actacatcac cgctctgcag gctgttcctc   1500
ctcggcctcg tcacgtgttc aatatgctaa agaagtatgt ccgcgcagaa cagaaggaca   1560
gacagcacac cctaaagcat ttcgagcatg tgcgcatggt ggatcccaag aaagccgctc   1620
agatccggtc ccaggttatg acacacctcc gtgtgattta tgagcgcatg aatcagtctc   1680
tctccctgct ctacaacgtg cctgcagtgg ccgaggagat tcaggatgaa gttgatgagc   1740
tgcttcagaa agagcaaaac tattcagatg acgtcttggc caacatgatt agtgaaccaa   1800
ggatcagtta cggaaacgat gctctcatgc catctttgac cgaaacgaaa accaccgtgg   1860
agctccttcc cgtgaatgga gagttcagcc tggacgatct ccagccgtgg cattcttttg   1920
gggctgactc tgtgccagcc aacacagaaa acgaaggttc tgggttgaca aatatcaaga   1980
cggaggagat ctctgaagtg aagatggatg cagaattccg acatgactca ggatatgaag   2040
ttcatcatca aaaattggtg ttctttgcag aagatgtggg ttcaaacaaa ggtgcaatca   2100
ttggactcat ggtgggcggt gttgtcatag cgacagtgat cgtcatcacc ttggtgatgc   2160
tgaagaagaa acagtacaca tccattcatc atggtgtggt ggaggttgac gccgctgtca   2220
ccccagagga gcgccacctg tccaagatgc agcagaacgg ctacgaaaat ccaacctaca   2280
agttctttga gcagatgcag aactagaccc ccgccacagc agcctctgaa gttggacagc   2340
aaaaccattg cttcactacc catcgg                                        2366
```

<210> SEQ ID NO 15
<211> LENGTH: 3294
<212> TYPE: DNA

```
<213> ORGANISM: Artificial sequence
<220> FEATURE:
<223> OTHER INFORMATION: Description of sequence: amyloid precursor
      protein coding sequence

<400> SEQUENCE: 15

gtcggatgat tcaagctcac ggggacgagc aggagcgctc tcgacttttc tagagcctca     60

gcgtcctagg actcaccttt ccctgatcct gcaccgtccc tctcctggcc ccagactctc    120

cctcccactg ttcacgaagc ccaggtaccc actgatggta atgctggcct gctggctgaa    180

ccccagattg ccatgttctg tggcagactg aacatgcaca tgaatgtcca gaatgggaag    240

tgggattcag atccatcagg gaccaaaacc tgcattgata ccaaggaagg catcctgcag    300

tattgccaag aagtctaccc tgaactgcag atcaccaatg tggtagaagc caaccaacca    360

gtgaccatcc agaactggtg caagcggggc cgcaagcagt gcaagaccca tccccacttt    420

gtgattccct accgctgctt agttggtgag tttgtaagtg atgcccttct cgttcctgac    480

aagtgcaaat tcttacacca ggagaggatg gatgtttgcg aaactcatct tcactggcac    540

accgtcgcca aagagacatg cagtgagaag agtaccaact tgcatgacta cggcatgttg    600

ctgccctgcg gaattgacaa gttccgaggg gtagagtttg tgtgttgccc actggctgaa    660

gaaagtgaca atgtggattc tgctgatgcg gaggaggatg actcggatgt ctggtggggc    720

ggagcagaca cagactatgc agatgggagt gaagacaaag tagtagaagt agcagaggag    780

gaagaagtgg ctgaggtgga agaagaagaa gccgatgatg acgaggacga tgaggatggt    840

gatgaggtag aggaagaggc tgaggaaccc tacgaagaag ccacagagag aaccaccagc    900

attgccacca ccaccaccac caccacagag tctgtggaag aggtggttcg agttcctaca    960

acagcagcca gtacccctga tgccgttgac aagtatctcg agacacctgg ggatgagaat   1020

gaacatgccc atttccagaa agccaaagag aggcttgagg ccaagcaccg agagagaatg   1080

tcccaggtca tgagagaatg ggaagaggca gaacgtcaag caaagaactt gcctaaagct   1140

gataagaagg cagttatcca gcatttccag gagaaagtgg aatctttgga acaggaagca   1200

gccaacgaga gacagcagct ggtggagaca cacatggcca gagtggaagc catgctcaat   1260

gaccgccgcc gcctggccct ggagaactac atcaccgctc tgcaggctgt tcctcctcgg   1320

cctcgtcacg tgttcaatat gctaaagaag tatgtccgcg cagaacagaa ggacagacag   1380

cacaccctaa agcatttcga gcatgtgcgc atggtggatc ccaagaaagc cgctcagatc   1440

cggtcccagg ttatgacaca cctccgtgtg atttatgagc gcatgaatca gtctctctcc   1500

ctgctctaca acgtgcctgc agtggccgag gagattcagg atgaagttga tgagctgctt   1560

cagaaagagc aaaactattc agatgacgtc ttggccaaca tgattagtga accaaggatc   1620

agttacggaa acgatgctct catgccatct ttgaccgaaa cgaaaaccac cgtggagctc   1680

cttcccgtga atggagagtt cagcctggac gatctccagc cgtggcattc ttttggggct   1740

gactctgtgc cagccaacac agaaaacgaa gttgagcctg ttgatgcccg ccctgctgcc   1800

gaccgaggac tgaccactcg accaggttct gggttgacaa atatcaagac ggaggagatc   1860

tctgaagtga agatggatgc agaattccga catgactcag gatatgaagt tcatcatcaa   1920

aaattggtgt tctttgcaga agatgtgggt tcaaacaaag gtgcaatcat tggactcatg   1980

gtgggcggtg ttgtcatagc gacagtgatc gtcatcacct tggtgatgct gaagaagaaa   2040

cagtacacat ccattcatca tggtgtggtg gaggttgacg ccgctgtcac cccagaggag   2100

cgccacctgt ccaagatgca gcagaacggc tacgaaaatc caacctacaa gttctttgag   2160
```

```
cagatgcaga actagacccc cgccacagca gcctctgaag ttggacagca aaaccattgc   2220

ttcactaccc atcggtgtcc atttatagaa taatgtggga agaaacaaac ccgttttatg   2280

atttactcat tatcgccttt tgacagctgt gctgtaacac aagtagatgc ctgaacttga   2340

attaatccac acatcagtaa tgtattctat ctctctttac attttggtct ctatactaca   2400

ttattaatgg gttttgtgta ctgtaaagaa tttagctgta tcaaactagt gcatgaatag   2460

attctctcct gattatttat cacatagccc cttagccagt tgtatattat tcttgtggtt   2520

tgtgacccaa ttaagtccta ctttacatat gctttaagaa tcgatggggg atgcttcatg   2580

tgaacgtggg agttcagctg cttctcttgc ctaagtattc ctttcctgat cactatgcat   2640

tttaaagtta aacattttta agtatttcag atgctttaga gagatttttt ttccatgact   2700

gcattttact gtacagattg ctgcttctgc tatatttgtg atataggaat taagaggata   2760

cacacgtttg tttcttcgtg cctgttttat gtgcacacat taggcattga gacttcaagc   2820

ttttcttttt ttgtccacgt atctttgggt ctttgataaa gaaaagaatc cctgttcatt   2880

gtaagcactt ttacggggcg ggtggggagg ggtgctctgc tggtcttcaa ttaccaagaa   2940

ttctccaaaa caattttctg caggatgatt gtacagaatc attgcttatg acatgatcgc   3000

tttctacact gtattacata aataaattaa ataaaataac cccgggcaag acttttcttt   3060

gaaggatgac tacagacatt aaataatcga agtaattttg ggtggggaga agaggcagat   3120

tcaattttct ttaaccagtc tgaagtttca tttatgatac aaaagaagat gaaaatggaa   3180

gtggcaatat aaggggatga ggaaggcatg cctggacaaa cccttctttt aagatgtgtc   3240

ttcaatttgt ataaaatggt gttttcatgt aaataaatac attcttggag gagc         3294
```

<210> SEQ ID NO 16
<211> LENGTH: 3633
<212> TYPE: DNA
<213> ORGANISM: Artificial sequence
<220> FEATURE:
<223> OTHER INFORMATION: Description of sequence: amyloid precursor protein coding sequence

<400> SEQUENCE: 16

```
agagttccgg aggctttggt tgtccattgt tagcttagaa gttggcgcag tgtgcgtgtg     60

atccacgcct aaatagcaca gccttgctgt gcgtggtaga agttgggtta gtgttgacat    120

gctgttgact caccctcccg aggatggaag ctctggcctg ggtcaagttg tggtcactgc    180

agttaacagt ttgttgatct cagggagtat tccacagttg ctgatgtaat tgacaatgat    240

tggagccagc tcttccccag attcaaatgg accaattaga ggacttgttg gttctgttta    300

tcaactatgt acccactgat ggtaatgctg gcctgctggc tgaaccccag attgccatgt    360

tctgtggcag actgaacatg cacatgaatg tccagaatgg gaagtgggat tcagatccat    420

cagggaccaa aacctgcatt gataccaagg aaggcatcct gcagtattgc caagaagtct    480

accctgaact gcagatcacc aatgtggtag aagccaacca accagtgacc atccagaact    540

ggtgcaagcg gggccgcaag cagtgcaaga cccatcccca ctttgtgatt ccctaccgct    600

gcttagttgg tgagtttgta agtgatgccc ttctcgttcc tgacaagtgc aaattcttac    660

accaggagag gatggatgtt tgcgaaactc atcttcactg gcacaccgtc gccaaagaga    720

catgcagtga gaagagtacc aacttgcatg actacggcat gttgctgccc tgcggaattg    780

acaagttccg aggggtagag tttgtgtgtt gcccactggc tgaagaaagt gacaatgtgg    840

attctgctga tgcggaggag gatgactcgg atgtctggtg ggcggagca gacacagact     900
```

```
atgcagatgg gagtgaagac aaagtagtag aagtagcaga ggaggaagaa gtggctgagg    960
tggaagaaga agaagccgat gatgacgagg acgatgagga tggtgatgag gtagaggaag   1020
aggctgagga accctacgaa gaagccacag agagaaccac cagcattgcc accaccacca   1080
ccaccaccac agagtctgtg gaagaggtgg ttcgagaggt gtgctctgaa caagccgaga   1140
cggggccgtg ccgagcaatg atctcccgct ggtactttga tgtgactgaa gggaagtgtg   1200
ccccattctt ttacggcgga tgtggcggca accggaacaa ctttgacaca gaagagtact   1260
gcatggccgt gtgtggcagc gccattccta caacagcagc cagtacccct gatgccgttg   1320
acaagtatct cgagacacct ggggatgaga atgaacatgc ccatttccag aaagccaaag   1380
agaggcttga ggccaagcac cgagagagaa tgtcccaggt catgagagaa tgggaagagg   1440
cagaacgtca agcaaagaac ttgcctaaag ctgataagaa ggcagttatc cagcatttcc   1500
aggagaaagt ggaatctttg gaacaggaag cagccaacga gagacagcag ctggtggaga   1560
cacacatggc cagagtggaa gccatgctca atgaccgccg ccgcctggcc ctggagaact   1620
acatcaccgc tctgcaggct gttcctcctc ggcctcgtca cgtgttcaat atgctaaaga   1680
agtatgtccg cgcagaacag aaggacagac agcacaccct aaagcatttc gagcatgtgc   1740
gcatggtgga tcccaagaaa gccgctcaga tccggtccca ggttatgaca cacctccgtg   1800
tgatttatga gcgcatgaat cagtctctct ccctgctcta caacgtgcct gcagtggccg   1860
aggagattca ggatgaagtt gatgagctgc ttcagaaaga gcaaaactat tcagatgacg   1920
tcttggccaa catgattagt gaaccaagga tcagttacgg aaacgatgct ctcatgccat   1980
ctttgaccga aacgaaaacc accgtggagc tccttcccgt gaatggagag ttcagcctgg   2040
acgatctcca gccgtggcat tcttttgggg ctgactctgt gccagccaac acagaaaacg   2100
aagttgagcc tgttgatgcc cgccctgctg ccgaccgagg actgaccact cgaccaggtt   2160
ctgggttgac aaatatcaag acggaggaga tctctgaagt gaagatggat gcagaattcc   2220
gacatgactc aggatatgaa gttcatcatc aaaaattggt gttctttgca gaagatgtgg   2280
gttcaaacaa aggtgcaatc attggactca tggtgggcgg tgttgtcata gcgacagtga   2340
tcgtcatcac cttggtgatg ctgaagaaga aacagtacac atccattcat catggtgtgg   2400
tggaggttga cgccgctgtc accccagagg agcgccacct gtccaagatg cagcagaacg   2460
gctacgaaaa tccaacctac aagttctttg agcagatgca gaactagacc cccgccacag   2520
cagcctctga agttggacag caaaaccatt gcttcactac ccatcggtgt ccatttatag   2580
aataatgtgg gaagaaacaa acccgtttta tgatttactc attatcgcct tttgacagct   2640
gtgctgtaac acaagtagat gcctgaactt gaattaatcc acacatcagt aatgtattct   2700
atctctcttt acattttggt ctctatacta cattattaat gggttttgtg tactgtaaag   2760
aatttagctg tatcaaacta gtgcatgaat agattctctc ctgattattt atcacatagc   2820
cccttagcca gttgtatatt attcttgtgg tttgtgaccc aattaagtcc tactttacat   2880
atgctttaag aatcgatggg ggatgcttca tgtgaacgtg ggagttcagc tgcttctctt   2940
gcctaagtat tcctttcctg atcactatgc attttaaagt taaacatttt taagtatttc   3000
agatgcttta gagagatttt ttttccatga ctgcatttta ctgtacagat tgctgcttct   3060
gctatatttg tgatatagga attaagagga tacacacgtt tgtttcttcg tgcctgtttt   3120
atgtgcacac attaggcatt gagacttcaa gcttttcttt ttttgtccac gtatctttgg   3180
gtctttgata aagaaaagaa tccctgttca ttgtaagcac ttttacgggg cgggtgggga   3240
ggggtgctct gctggtcttc aattaccaag aattctccaa aacaattttc tgcaggatga   3300
```

```
ttgtacagaa tcattgctta tgacatgatc gctttctaca ctgtattaca taaataaatt   3360

aaataaaata accccgggca agacttttct ttgaaggatg actacagaca ttaaataatc   3420

gaagtaattt tgggtgggga gaagaggcag attcaatttt ctttaaccag tctgaagttt   3480

catttatgat acaaaagaag atgaaaatgg aagtggcaat ataaggggat gaggaaggca   3540

tgcctggaca aacccttctt ttaagatgtg tcttcaattt gtataaaatg gtgttttcat   3600

gtaaataaat acattcttgg aggagcacca ttg                                 3633


<210> SEQ ID NO 17
<211> LENGTH: 2846
<212> TYPE: DNA
<213> ORGANISM: Artificial sequence
<220> FEATURE:
<223> OTHER INFORMATION: Description of sequence: amyloid precursor
      protein coding sequence

<400> SEQUENCE: 17

agagttccgg aggctttggt tgtccattgt tagcttagaa gttggcgcag tgtgcgtgtg     60

atccacgcct aaatagcaca gccttgctgt gcgtggtaga agttgggtta gtgttgacat    120

gctgttgact caccctcccg aggatggaag ctctggcctg ggtcaagttg tggtcactgc    180

agttaacagt ttgttgatct cagggagtat tccacagttg ctgatgtaat tgacaatgat    240

tggagccagc tcttccccag attcaaatgg accaattaga ggacttgttg gttctgttta    300

tcaactatgt acccactgat ggtaatgctg gcctgctggc tgaaccccag attgccatgt    360

tctgtggcag actgaacatg cacatgaatg tccagaatgg gaagtgggat tcagatccat    420

cagggaccaa aacctgcatt gataccaagg aaggcatcct gcagtattgc caagaagtct    480

accctgaact gcagatcacc aatgtggtag aagccaacca accagtgacc atccagaact    540

ggtgcaagcg gggccgcaag cagtgcaaga cccatcccca ctttgtgatt ccctaccgct    600

gcttagttgg tgagtttgta agtgatgccc ttctcgttcc tgacaagtgc aaattcttac    660

accaggagag gatggatgtt tgcgaaactc atcttcactg gcacaccgtc gccaaagaga    720

catgcagtga gaagagtacc aacttgcatg actacggcat gttgctgccc tgcggaattg    780

acaagttccg aggggtagag tttgtgtgtt gcccactggc tgaagaaagt gacaatgtgg    840

attctgctga tgcggaggag gatgactcgg atgtctggtg gggcggagca gacacagact    900

atgcagatgg gagtgaagac aaagtagtag aagtagcaga ggaggaagaa gtggctgagg    960

tggaagaaga agaagccgat gatgacgagg acgatgagga tggtgatgag gtagaggaag   1020

aggctgagga accctacgaa gaagccacag agagaaccac cagcattgcc accaccacca   1080

ccaccaccac agagtctgtg gaagaggtgg ttcgagaggt gtgctctgaa caagccgaga   1140

cggggccgtg ccgagcaatg atctcccgct ggtactttga tgtgactgaa gggaagtgtg   1200

ccccattctt ttacggcgga tgtggcggca accggaacaa ctttgacaca gaagagtact   1260

gcatggccgt gtgtggcagc gccattccta caacagcagc cagtacccct gatgccgttg   1320

acaagtatct cgagacacct ggggatgaga atgaacatgc ccatttccag aaagccaaag   1380

agaggcttga ggccaagcac cgagagagaa tgtcccaggt catgagagaa tgggaagagg   1440

cagaacgtca agcaaagaac ttgcctaaag ctgataagaa ggcagttatc cagcatttcc   1500

aggagaaagt ggaatctttg gaacaggaag cagccaacga gagacagcag ctggtggaga   1560

cacacatggc cagagtggaa gccatgctca atgaccgccg ccgcctggcc ctggagaact   1620

acatcaccgc tctgcaggct gttcctcctc ggcctcgtca cgtgttcaat atgctaaaga   1680
```

```
agtatgtccg cgcagaacag aaggacagac agcacaccct aaagcatttc gagcatgtgc   1740

gcatggtgga tcccaagaaa gccgctcaga tccggtccca ggttatgaca cacctccgtg   1800

tgatttatga gcgcatgaat cagtctctct ccctgctcta caacgtgcct gcagtggccg   1860

aggagattca ggatgaagtt gatgagctgc ttcagaaaga gcaaaactat tcagatgacg   1920

tcttggccaa catgattagt gaaccaagga tcagttacgg aaacgatgct ctcatgccat   1980

ctttgaccga aacgaaaacc accgtggagc tccttcccgt gaatggagag ttcagcctgg   2040

acgatctcca gccgtggcat tcttttgggg ctgactctgt gccagccaac acagaaaacg   2100

aagttgagcc tgttgatgcc cgccctgctg ccgaccgagg actgaccact cgaccaggtt   2160

ctgggttgac aaatatcaag acggaggaga tctctgaagt gaagatggat gcagaattcc   2220

gacatgactc aggatatgaa gttcatcatc aaaaattggt gttctttgca gaagatgtgg   2280

gttcaaacaa aggtgcaatc attggactca tggtgggcgg tgttgtcata gcgacagtga   2340

tcgtcatcac cttggtgatg ctgaagaaga aacagtacac atccattcat catggtgtgg   2400

tggaggttga cgccgctgtc accccagagg agcgccacct gtccaagatg cagcagaacg   2460

gctacgaaaa tccaacctac aagttctttg agcagatgca gaactagacc cccgccacag   2520

cagcctctga agttggacag caaaaccatt gcttcactac ccatcggtgt ccatttatag   2580

aataatgtgg gaagaaacaa acccgtttta tgatttactc attatcgcct tttgacagct   2640

gtgctgtaac acaagtagat gcctgaactt gaattaatcc acacatcagt aatgtattct   2700

atctctcttt acattttggt ctctatacta cattattaat gggttttgtg tactgtaaag   2760

aatttagctg tatcaaacta gtgcatgaat agattctctc ctgattattt atcacatagc   2820

cccttagcca gttgtatatt attctt                                        2846
```

<210> SEQ ID NO 18
<211> LENGTH: 1846
<212> TYPE: DNA
<213> ORGANISM: Artificial sequence
<220> FEATURE:
<223> OTHER INFORMATION: Description of sequence: amyloid precursor protein coding sequence

<400> SEQUENCE: 18

```
actgcagatc accaatgtgg tagaagccaa ccaaccagtg accatccaga actggtgcaa     60

gcggggccgc aagcagtgca agacccatcc ccactttgtg attccctacc gctgcttagt    120

tggtgagttt gtaagtgatg cccttctcgt tcctgacaag tgcaaattct tacaccagga    180

gaggatggat gtttgcgaaa ctcatcttca ctggcacacc gtcgccaaag agacatgcag    240

tgagaagagt accaacttgc atgactacgg catgttgctg ccctgcggaa ttgacaagtt    300

ccgaggggta gagtttgtgt gttgcccact ggctgaagaa agtgacaatg tggattctgc    360

tgatgcggag gaggatgact cggatgtctg gtggggcgga gcagacacag actatgcaga    420

tgggagtgaa gacaaagtag tagaagtagc agaggaggaa gaagtggctg aggtggaaga    480

agaagaagcc gatgatgacg aggacgatga ggatggtgat gaggtagagg aagaggctga    540

ggaaccctac gaagaagcca cagagagaac caccagcatt gccaccacca ccaccaccac    600

cacagagtct gtggaagagg tggttcgaga ggtgtgctct gaacaagccg agacggggcc    660

gtgccgagca atgatctccc gctggtactt tgatgtgact gaagggaagt gtgccccatt    720

cttttacggc ggatgtggcg gcaaccggaa caactttgac acagaagagt actgcatggc    780

cgtgtgtggc agcgccattc ctacaacagc agccagtacc cctgatgccg ttgacaagta    840
```

```
tctcgagaca cctggggatg agaatgaaca tgcccatttc cagaaagcca aagagaggct    900

tgaggccaag caccgagaga gaatgtccca ggtcatgaga gaatgggaag aggcagaacg    960

tcaagcaaag aacttgccta aagctgataa gaaggcagtt atccagcatt tccaggagaa   1020

agtggaatct ttggaacagg aagcagccaa cgagagacag cagctggtgg agacacacat   1080

ggccagagtg gaagccatgc tcaatgaccg ccgccgcctg gccctggaga actacatcac   1140

cgctctgcag gctgttcctc ctcggcctcg tcacgtgttc aatatgctaa agaagtatgt   1200

ccgcgcagaa cagaaggaca gacagcacac cctaaagcat ttcgagcatg tgcgcatggt   1260

ggatcccaag aaagccgctc agatccggtc ccaggttatg acacacctcc gtgtgattta   1320

tgagcgcatg aatcagtctc tctccctgct ctacaacgtg cctgcagtgg ccgaggagat   1380

tcaggatgaa gttggtgcag tggctcatgc ctgtaattcc agcattttgg gaggccaagg   1440

tgggcagatg acttgagccc agaagttcaa gaccagaatg ggaaacatgg caagaccaca   1500

tttctacaaa aaaattatcc aggcatgata acatctattt gtagtcccag ctactcagga   1560

ggctgtggtg ggaggatctc ctgagcctgg ggtggctgag gctgcagtga gccttgatca   1620

cgccacctgg gcaatagagc aagaccctgt ctcaaaaaaa ggaagaaaaa gactattatt   1680

tcccccattg aatggtcttg gcactattac acaaaatcaa ttgtccatag ataatatggg   1740

tttatttctt aattcttagt tcttttcttt gatctgtgtg cctgtgctta ctgtagtacc   1800

acactgtttt gattattgta gctttgtagt aaattttgaa atcagc                 1846
```

```
<210> SEQ ID NO 19
<211> LENGTH: 2517
<212> TYPE: DNA
<213> ORGANISM: Artificial sequence
<220> FEATURE:
<223> OTHER INFORMATION: Description of sequence: amyloid precursor
      protein coding sequence

<400> SEQUENCE: 19

cagcagcgca ctcggtgccc cgcgcagggt cgcgatgctg cccggtttgg cactgctcct     60

gctggccgcc tggacggctc gggcgctgga ggtctaccct gaactgcaga tcaccaatgt    120

ggtagaagcc aaccaaccag tgaccatcca gaactggtgc aagcggggcc gcaagcagtg    180

caagacccat ccccactttg tgattcccta ccgctgctta gttggtgagt ttgtaagtga    240

tgcccttctc gttcctgaca agtgcaaatt cttacaccag gagaggatgg atgtttgcga    300

aactcatctt cactggcaca ccgtcgccaa agagacatgc agtgagaaga gtaccaactt    360

gcatgactac ggcatgttgc tgccctgcgg aattgacaag ttccgagggg tagagtttgt    420

gtgttgccca ctggctgaag aaagtgacaa tgtggattct gctgatgcgg aggaggatga    480

ctcggatgtc tggtggggcg gagcagacac agactatgca gatgggagtg aagacaaagt    540

agtagaagta gcagaggagg aagaagtggc tgaggtggaa gaagaagaag ccgatgatga    600

cgaggacgat gaggatggtg atgaggtaga ggaagaggct gaggaaccct acgaagaagc    660

cacagagaga accaccagca ttgccaccac caccaccacc accacagagt ctgtggaaga    720

ggtggttcga gaggtgtgct ctgaacaagc cgagacgggg ccgtgccgag caatgatctc    780

ccgctggtac tttgatgtga ctgaagggaa gtgtgcccca ttcttttacg gcggatgtgg    840

cggcaaccgg aacaactttg acacagaaga gtactgcatg gccgtgtgtg gcagcgccat    900

gtcccaaagt ttactcaaga ctacccagga acctcttgcc cgagatcctg ttaaacttcc    960

tacaacagca gccagtaccc ctgatgccgt tgacaagtat ctcgagacac ctggggatga   1020
```

```
gaatgaacat gcccatttcc agaaagccaa agagaggctt gaggccaagc accgagagag   1080

aatgtcccag gtcatgagag aatgggaaga ggcagaacgt caagcaaaga acttgcctaa   1140

agctgataag aaggcagtta tccagcattt ccaggagaaa gtggaatctt tggaacagga   1200

agcagccaac gagagacagc agctggtgga gacacacatg gccagagtgg aagccatgct   1260

caatgaccgc cgccgcctgg ccctggagaa ctacatcacc gctctgcagg ctgttcctcc   1320

tcggcctcgt cacgtgttca atatgctaaa gaagtatgtc cgcgcagaac agaaggacag   1380

acagcacacc ctaaagcatt tcgagcatgt gcgcatggtg gatcccaaga aagccgctca   1440

gatccggtcc caggttatga cacacctccg tgtgatttat gagcgcatga atcagtctct   1500

ctccctgctc tacaacgtgc ctgcagtggc cgaggagatt caggatgaag ttgatgagct   1560

gcttcagaaa gagcaaaact attcagatga cgtcttggcc aacatgatta gtgaaccaag   1620

gatcagttac ggaaacgatg ctctcatgcc atctttgacc gaaacgaaaa ccaccgtgga   1680

gctccttccc gtgaatggag agttcagcct ggacgatctc cagccgtggc attcttttgg   1740

ggctgactct gtgccagcca acacagaaaa cgaagttgag cctgttgatg cccgccctgc   1800

tgccgaccga ggactgacca ctcgaccagg ttctgggttg acaaatatca agacggagga   1860

gatctctgaa gtgaagatgg atgcagaatt ccgacatgac tcaggatatg aagttcatca   1920

tcaaaaattg gtgttctttg cagaagatgt gggttcaaac aaaggtgcaa tcattggact   1980

catggtgggc ggtgttgtca tagcgacagt gatcgtcatc accttggtga tgctgaagaa   2040

gaaacagtac acatccattc atcatggtgt ggtggaggtt gacgccgctg tcaccccaga   2100

ggagcgccac ctgtccaaga tgcagcagaa cggctacgaa aatccaacct acaagttctt   2160

tgagcagatg cagaactaga cccccgccac agcagcctct gaagttggac agcaaaacca   2220

ttgcttcact acccatcggt gtccatttat agaataatgt gggaagaaac aaacccgttt   2280

tatgatttac tcattatcgc cttttgacag ctgtgctgta acacaagtag atgcctgaac   2340

ttgaattaat ccacacatca gtaatgtatt ctatctctct ttacattttg gtctctatac   2400

tacattatta atgggttttg tgtactgtaa agaatttagc tgtatcaaac tagtgcatga   2460

atagattctc tcctgattat ttatcacata gcccttagc cagttgtata ttattct       2517
```

```
<210> SEQ ID NO 20
<211> LENGTH: 541
<212> TYPE: DNA
<213> ORGANISM: Artificial sequence
<220> FEATURE:
<223> OTHER INFORMATION: Description of sequence: amyloid precursor
      protein coding sequence

<400> SEQUENCE: 20

gggcggagca gacacagact atgcagatgg gagtgaagac aaagtagtag aagtagcaga     60

ggaggaagaa gtggctgagg tggaagaaga agaagccgat gatgacgagg acgatgagga    120

tggtgatgag gtagaggaag aggctgagga accctacgaa gaagccacag agagaaccac    180

cagcattgcc accaccacca ccaccaccac agagtctgtg gaagaggtgg ttcgagtgtc    240

ccaaagttta ctcaagacta cccaggaacc tcttgcccga gatcctgtta aacttcctac    300

aacagcagcc agtacccctg atgccgttga caagtatctc gagacacctg gggatgagaa    360

tgaacatgcc catttccaga aagccaaaga gaggcttgag gccaagcacc gagagagaat    420

gtcccaggtc atgagagaat gggaagaggc agaacgtcaa gcaaagaact tgcctaaagc    480

tgataagaag gcagttatcc agcatttcca ggagaaagtg gaatctttgg aacaggaagc    540
```

a 541

<210> SEQ ID NO 21
<211> LENGTH: 816
<212> TYPE: DNA
<213> ORGANISM: Artificial sequence
<220> FEATURE:
<223> OTHER INFORMATION: Description of sequence: amyloid precursor protein coding sequence

<400> SEQUENCE: 21
atccttgcca acctctcaac caggatttaa cttctgcttt tcccccattt tcaaaaatta 60
tagcatgtat ttaaaggcag cagaagcctt actttcaggt ttcccttacc ctttcatttc 120
tttttgttca aaataggtag taattgaagt tttaaatata gggtatcatt tttctttaag 180
agtcatttat caattttctt ctaacttcag gcctagaaag aagttttggg taggctttgt 240
cttacagtgt tattatttat gagtaaaact aattggttgt cctgcatact ttaattatga 300
tgtaatacag gttctgggtt gacaaatatc aagacggagg agatctctga agtgaagatg 360
gatgcagaat tccgacatga ctcaggatat gaagttcatc atcaaaaatt ggtgttcttt 420
gcagaagatg tgggttcaaa caaaggtgca atcattggac tcatggtggg cggtgttgtc 480
atagcgacag tgatcgtcat caccttggtg atgctgaaga agaaacagta cacatccatt 540
catcatggtg tggtggaggt tgacgccgct gtcaccccag aggagcgcca cctgtccaag 600
atgcagcaga acggctacga aaatccaacc tacaagttct ttgagcagat gcagaactag 660
acccccgcca cagcagcctc tgaagttgga cagcaaaacc attgcttcac tacccatcgg 720
tgtccattta tagaataatg tgggaagaaa caaacccgtt ttatgattta ctcattatcg 780
ccttttgaca gctgtgctgt aacacaagta gatgcc 816

<210> SEQ ID NO 22
<211> LENGTH: 619
<212> TYPE: DNA
<213> ORGANISM: Artificial sequence
<220> FEATURE:
<223> OTHER INFORMATION: Description of sequence: amyloid precursor protein coding sequence

<400> SEQUENCE: 22
cagactatgc agatgggagt gaagacaaag tagtagaagt agcagaggag gaagaagtgg 60
ctgaggtgga agaagaagaa gccgatgatg acgaggacga tgaggatggt gatgaggtag 120
aggaagaggc tgaggaaccc tacgaagaag ccacagagag aaccaccagc attgccacca 180
ccaccaccac caccacagag tctgtggaag aggtggttcg agaggtgtgc tctgaacaag 240
ccgagacggg gccgtgccga gcaatgatct cccgctggta ctttgatgtg actgaaggga 300
agtgtgcccc attcttttac ggcggatgtg gcggcaaccg gaacaacttt gacacagaag 360
agtactgcat ggccgtgtgt ggcagcgcca tgtcccaaag tttactcaag actacccagg 420
aacctcttgc ccgagatcct gttaaacgta cgttgtcatt cacctgaggg aagggaagag 480
gggaggagga tgctgcttgg ttcacataac tccagcatca tcaccttctt tgcatggttt 540
tgtgtttctt gaacacctgt cttagtaaaa tgtttcttcc cattaccttg cttgtaatta 600
catctgattt tgccagaca 619

<210> SEQ ID NO 23
<211> LENGTH: 1309
<212> TYPE: DNA

<213> ORGANISM: Artificial sequence
<220> FEATURE:
<223> OTHER INFORMATION: Description of sequence: amyloid precursor protein coding sequence

<400> SEQUENCE: 23

```
cgagagcacg cggaggagcg tgcgcggggg ccccgggaga cggcggcggt ggcggcgcgg     60

gcagagcaag gacgcggcgg atcccactcg cacagcagcg cactcggtgc cccgcgcagg    120

gtcgcgatgc tgcccggttt ggcactgctc ctgctggccg cctggacggc tcgggcgctg    180

gaggtaccca ctgatggtaa tgctggcctg ctggctgaac cccagattgc catgttctgt    240

ggcagactga acatgcacat gaatgtccag aatgggaagt gggattcaga tccatcaggg    300

accaaaacct gcattgatac caaggaaggc atcctgcagt attgccaaga agtctaccct    360

gaactgcaga tcaccaatgt ggtagaagcc aaccaaccag tgaccatcca gaactggtgc    420

aagcggggcc gcaagcagtg caagacccat ccccactttg tgattcccta ccgctgctta    480

gttggtgagt ttgtaagtga tgcccttctc gttcctgaca agtgcaaatt cttacaccag    540

gagaggatgg atgtttgcga aactcatctt cactggcaca ccgtcgccaa agagacatgc    600

agtgagaaga gtaccaactt gcatgactac ggcatgttgc tgccctgcgg aattgacaag    660

ttccgagggg tagagtttgt gtgttgccca ctggctgaag aaagtgacaa tgtggattct    720

gctgatgcgg aggaggatga ctcggatgtc tggtggggcg gagcagacac agactatgca    780

gatgggagtg aagacaaagt agtagaagta gcagaggagg aagaagtggc tgaggtggaa    840

gaagaagaag ccgatgatga cgaggacgat gaggatggtg atgaggtaga ggaagaggct    900

gaggaaccct acgaagaagc cacagagaga accaccagca ttgccaccac caccaccacc    960

accacagagt ctgtggaaga ggtggttcga gagaagtggt ataaggaagt acattctggc   1020

caggcacgat ggctcatgct gtaatcccag cactttggga ggccgaggtg ggtgcatcac   1080

ctgaggtcag gagtttgaga ccagcctggc caacatggtg aaacccctcg ctactaaaaa   1140

tacaaaaatt agccgggcgt ggtggcacac acctgtggtc ccagctactc gggaggctga   1200

agcaggagaa tcgcttgaac ccgggagacg gaggttgcag taagccgagt tcactccatt   1260

gtactctagc ctgggtgaca gagcgagatt cgtctcaaaa aaaaaaaaa               1309
```

<210> SEQ ID NO 24
<211> LENGTH: 582
<212> TYPE: DNA
<213> ORGANISM: Artificial sequence
<220> FEATURE:
<223> OTHER INFORMATION: Description of sequence: amyloid precursor protein coding sequence

<400> SEQUENCE: 24

```
gtaacattct aaaggtagta gggtcttgat tgggttgctt aggcattaaa aggctgttta     60

acttgtcttg aagtctatct ttccttgatg tcttctgcgg taagaacact gtgatacaga    120

tggaatgacg ggaagtggtt ttcctttctt tcagttggtg agtttgtaag tgatgccctt    180

ctcgttcctg acaagtgcaa attcttacac caggagagga tggatgtttg cgaaactcat    240

cttcactggc acaccgtcgc caaagagaca tgcagtgaga agagtaccaa cttgcatgac    300

tacggcatgt tgctgccctg cggaattgac aagttccgag ggtagagtt tgtgtgttgc    360

ccactggctg aagaaagtga caatgtggat tctgctgatg cggaggagga tgactcggat    420

gtctggtggg gcggagcaga cacagactat gcagatggga gtgaagacaa agtagtagaa    480

gtagcagagg aggaagaagt ggctgaggtg gaagaagaag aagccgatga tgacgaggac    540
```

```
gatgaggatg gtgatgaggt agaggaagag gctgaggaac cc                 582


<210> SEQ ID NO 25
<211> LENGTH: 361
<212> TYPE: DNA
<213> ORGANISM: Artificial sequence
<220> FEATURE:
<223> OTHER INFORMATION: Description of sequence: amyloid precursor
      protein coding sequence

<400> SEQUENCE: 25

actggagggc tgagaagaga ctgatggcat ttgttgttct tgaccttgaa agaagagttg     60

cagattgttg gagcaaggcc agatggtaat aggttggaaa gaacaagtga ggggcgtgag    120

agtgacagtc tacaaccccg ttaagaagtt atctgtgaaa atgcctcttc ctgtcttgat    180

tatagcctcc ctcgcacatg gctttctgag tatgttggtg agtttgtaag tgatgccctt    240

ctcgttcctg acaagtgcaa attcttacac caggagagga tggatgtttg cgaaactcat    300

cttcactggc acaccgtcgc caaagagaca tgcagtgaga agagtaccaa cttgcatgac    360

t                                                                    361


<210> SEQ ID NO 26
<211> LENGTH: 667
<212> TYPE: DNA
<213> ORGANISM: Artificial sequence
<220> FEATURE:
<223> OTHER INFORMATION: Description of sequence: amyloid precursor
      protein coding sequence

<400> SEQUENCE: 26

ctgaacatgc acatgaatgt ccagaatggg aagtgggatt cagatccatc agggaccaaa     60

acctgcattg ataccaagga aggcatcctg cagtattgcc aagaagtcta ccctgaactg    120

cagatcacca atgtggtaga agccaaccaa ccagtgacca tccagaactg gtgcaagcgg    180

ggccgcaagc agtgcaagac ccatccccac tttgtgattc cctaccgctg cttaggtgag    240

ccggccggcc gtggggctgg tgttgattgg gggcctggtc ttgagggaag aaaaagagga    300

tgctcctgtt aggtcacata cacagacttg ttcttcagca cattgccact ctgtgttgta    360

ctgtgttttg gactcttgca gttacattct gtgcactgac cctataggag cagtattttt    420

gagttccctg cctcagaatg aatttaccca gggtgtatat tgaaattaca aattcctggg    480

ccagttccag gactcctgaa tgaaaaatgc ctatagtagc ggatccggga attcttattt    540

taccgtatcg catagatgat tctcatgaac aggggccttg tgtgtttctt cacatagact    600

ttctagaaga aagaatctaa tgtgaagctg cagcattttg ttaatttcta aaaaaaaaaa    660

aaaaaaa                                                              667


<210> SEQ ID NO 27
<211> LENGTH: 374
<212> TYPE: DNA
<213> ORGANISM: Artificial sequence
<220> FEATURE:
<223> OTHER INFORMATION: Description of sequence: amyloid precursor
      protein coding sequence

<400> SEQUENCE: 27

ggcgcggcct cttccctggc agctctgggg actctggttt agttcccctg ggggcacagg     60

atgctgggga gggtccgaag ggtctttttt ttagggtgca gataaaagga tcgaattgag    120

tgaagattaa gacggagaag atggcgcctc tgcagtgcag caaagaaaag ctgtgtggag    180
```

-continued

```
gctgcagcct agtgaaatcc acccaccact aggtacccac tgatggtaat gctggcctgc    240

tggctgaacc ccagattgcc atgttctgtg gcagactgaa catgcacatg aatgtccaga    300

atgggaagtg ggattcagat ccatcaggga ccaaaacctg cattgatacc aaggaaggca    360

tcctgcagta ttgc                                                      374
```